(12) United States Patent
Yamauchi et al.

(10) Patent No.: US 10,450,618 B2
(45) Date of Patent: Oct. 22, 2019

(54) METHOD FOR IDENTIFYING VARIETY OF HOP

(71) Applicant: SUNTORY HOLDINGS LIMITED, Osaka-shi, Osaka (JP)

(72) Inventors: Hiromasa Yamauchi, Kanagawa (JP); Susumu Furukubo, Kanagawa (JP)

(73) Assignee: SUNTORY HOLDINGS LIMITED, Osaka-shi, Osaka (JP)

( * ) Notice: Subject to any disclaimer, the term of this patent is extended or adjusted under 35 U.S.C. 154(b) by 176 days.

(21) Appl. No.: 15/727,656

(22) Filed: Oct. 9, 2017

(65) Prior Publication Data

US 2018/0119234 A1    May 3, 2018

Related U.S. Application Data

(62) Division of application No. 14/406,321, filed as application No. PCT/JP2013/065895 on Jun. 7, 2013, now Pat. No. 9,816,146.

(30) Foreign Application Priority Data

Jun. 7, 2012   (JP) ................ 2012-130282

(51) Int. Cl.
   C12P 19/34   (2006.01)
   C12Q 1/68    (2018.01)
   C12Q 1/6895  (2018.01)
   C07H 21/02   (2006.01)

(52) U.S. Cl.
   CPC ..... *C12Q 1/6895* (2013.01); *C12Q 2600/156* (2013.01)

(58) Field of Classification Search
   CPC ................ C12Q 1/6895; C12Q 2600/156
   See application file for complete search history.

(56) References Cited

U.S. PATENT DOCUMENTS 5,948,650 A    9/1999  Araki et al.

FOREIGN PATENT DOCUMENTS

| CN | 1159212 A | 9/1997 |
| EP | 2088194 A1 | 8/2009 |
| JP | H11-103895 A | 4/1999 |
| JP | 2006-034142 A | 2/2006 |
| JP | 2007-330230 A | 12/2007 |
| JP | 2009-100653 A | 5/2009 |
| JP | 2011-188846 A | 9/2011 |
| WO | WO-1997/05281 A1 | 2/1997 |

OTHER PUBLICATIONS

Patzak, J. et al. New STS molecular markers for assessment of genetic diversity and DNA fingerprinting in hop (*Humulus lupulus* L.) Genome, 2007, 50(1): 15-25 (Year: 2007).*

International Search Report dated Sep. 10, 2013 for PCT/JP2013/065895.
CN Application No. 201380029775.0—Office Action dated Nov. 26, 2015 (with English translation).
Shen, et al., "Identification of transcriptome SNPs between Xiphophorus lines and species for assessing allele specific gene expression within F1 interspecies hybrids", Comp Biochem Physiol C Toxicol Pharmacol., Jan. 2012, 155(1), pp. 102-108.
EP Application No. 13800328.0—Partial Supplementary European Search Report dated Feb. 23, 2016.
Appleby, et al., "New Technologies for Ultra-High Through put Genotyping in Plants", Methods in Molecular Biology, Jan. 1, 2009, vol. 513, pp. 19-39.
Castro, et al., "DNA Sequence and Expression Variation of Hop (*Humulus lupulus*) Valeropheone Synthase (VPS), a Key Gene in Bitter Acid Biosynthesis", Annals of Botany, May 12, 2008, vol. 102, pp. 265-273
Henning, et al., "Simple SNP-based minimal marker genotyping for*Humulus lupulus* L. identification and variety validation", BMC Research Notes, Oct. 6, 2015, vol. 8, No. 1, pp. 542.
Koepke, et al., "Rapid gene-based SNP and haplotype marker development in non-model eukaryotes using 3'UTR sequening", BMC Genomics, Jan. 12, 2012, vol. 13, No. 1, pp. 18.
Russell, et al., "Identification, utilization and mapping of novel transcriptome-based markers from blackcurrant (*Ribes nigrum*)", BMS Plant Biology, Oct. 28, 2011, vol. 11, No. 1, pp. 147.
Varshney, et al., "Next -generation sequencing technologies and their implications for crop genetics and breeding" Trends in Biotechnology, Sep. 1, 2009, vol. 27 No. 9, pp. 522-530.
Yamauchi, et al., "Newly Developed SNP-Based Identification Method of Hop Varieties", Journal of the American Society of Brewing Chemists, Jan. 1, 2014, vol. 72, No. 4, pp. 239-245.
EP Application 13800328.0—Extended European Search Report dated Jul. 8, 2016.
Nagel, et al., "EST Analysis of Hop Glandular Trichomes Identifies an O-Methyltransferase That Catalyzes the Biosynthesis of Xanthohumol", The Plant Cell, Jan. 1, 2008, vol. 20, No. 1, pp. 186-200.
Database EMBL [Online], Sep. 18, 2008, Database Accession No. GD250033, HLUTR3CH_T3_016_F03_28MAR2006_0021 HLUTR3CH Humulus lupulus cDNA, mRNA sequence, Abstract, XP-002759207.
Database Geneseq [Online], Jul. 29, 2004, Database Accession No. ABD22424, "Human cathepsin C-derived oligo SEQ ID 1436", Abstract, XP002759208.

(Continued)

*Primary Examiner* — Stephen T Kapushoc
(74) *Attorney, Agent, or Firm* — Drinker Biddle & Reath LLP

(57) ABSTRACT

The present invention relates to a method for identifying the variety of a hop by using an identification marker comprising at least one single nucleotide polymorphism that differs among varieties, and a method for preparing said identification marker. The present invention also provides a primer or a probe to be used in the method for identifying the variety of a hop, and a nucleic acid of a region including said identification marker. The present invention further provides a method for detecting the intrusion of different varieties in a hop sample.

6 Claims, 8 Drawing Sheets

Specification includes a Sequence Listing.

(56) References Cited

OTHER PUBLICATIONS

Database Geneseq [Online], Nov. 10, 2011, Database Accession No. AZN03059, "Human CFTR gene exon 6 forward PCR primer CFe6Bf2 SEQ:70.", Abstract, XP002759203.
Database EMBL [Online], Aug. 18, 2010, Database accession No. HD506062, "Sequence 382778 from Patent EP2213738.", Abstract, XP002759204.
Database Geneseq [Online], Nov. 29, 2007, Database accession No. AJH05242, "Human cancer detection sequence SEQ ID No. 1707.", Abstract, XP002759205.
Database Geneseq [online], Oct. 15, 2001, Database accession No. AAH26401, "Arabidopsis RPS18C gene leader sequence mRNA 15 moiety.", Abstract, XP002759206.
Database EMBL [Online], Oct. 11, 2007, Database accession No. EX520192, "HOPS-CTAB-39_2007-0820_1/HOPS-CTAB-39_P08_009_1 *Humulus lupulus* (L. cultivar Phoenix) Trichome isolated from the female flower at mid-developmental stage Humulus lupulus cDNA, mRNA sequence.", Abstract, XP002759209.
Patzak, J., et al., "Gene Specific Molecular Markers for Hop (*Humulus lupulus* L.)", Proc. 2nd Internat. Humulus Symposium, Acta Hort. 848, ISHS 2009, pp. 73-80.
Natsume, S., et al. "The Draft Genome of Hop (*Humulus lupulus*), an Essences for Brewing", Plant Cell Physiol. 56(3): 428-441 (2015).
Martin, T., et al., Plant Biotechnology Journal (2009) 7, pp. 334-346.
EP Application 18201813.5—Extended European Search Report dated Jan. 23, 2019.
Database EMBL [Online], Aug. 18, 2010, "Sequence 3780 from Patent EP2213738.", XP55540709, retrieved from EBI accession No. EM_PAT:HD127064; Database accession No. HD127064, * abstract; sequence *.
Database EMBL [Online], Aug. 18, 2010 "Sequence 615104 from Patent EP2213738.", XP55540711, retrieved from EBI accession No. EM_PAT:HD738388, Database accession No. HD738388 * abstract; sequence *.

* cited by examiner

SNP analysis results in region A 1

| SNP position / Variety to be identified | 74 | 77 | 87 | 103 | 116 | 118 | 121 | 125 | 134 | 135 | 148 | 192 | 195 | 197 | 199 | 203 | 204 | 226 | 230 | 235 | 306 | 316 | 330 | 532 |
|---|---|---|---|---|---|---|---|---|---|---|---|---|---|---|---|---|---|---|---|---|---|---|---|---|
| Saaz | W | T | K | A | W | Y | W | W | K | R | Y | G | K | W | T | R | S | M | Y | Y | Y | M | T | G |
| Sladeck | A | C | T | G | T | T | T | A | T | G | T | A | G | T | C | G | C | A | C | T | C | C | A | C |
| Premiant | A | C | T | G | T | T | T | A | T | G | T | A | G | T | C | G | C | A | C | T | C | C | A | C |
| Tradition | W | T | K | A | W | Y | W | W | K | R | Y | G | K | W | T | R | S | M | Y | Y | Y | C | W | G |
| Spalter | W | T | K | A | W | Y | W | W | K | R | Y | G | K | W | T | R | S | M | Y | Y | Y | M | W | G |
| Spalter Select | A | C | T | G | T | T | T | A | T | G | T | A | G | T | C | G | C | A | C | T | C | C | A | C |
| Perle | A | C | T | G | T | T | T | A | T | G | T | A | G | T | C | G | C | A | C | T | C | C | A | C |
| Tettnang | W | T | K | A | W | Y | W | W | K | R | T | G | K | W | T | R | S | C | Y | Y | Y | M | W | S |
| Brewer's Gold | A | T | K | A | T | T | W | A | T | R | T | G | G | T | T | R | S | M | Y | T | Y | M | W | C |
| Northern Brewer | A | C | T | G | T | T | T | A | T | G | T | A | G | T | C | G | C | A | C | T | C | C | A | C |
| Magnum | A | C | T | G | T | T | T | A | T | G | T | R | G | T | C | G | C | A | C | T | C | C | A | C |
| Herkules | A | C | T | G | T | T | T | A | T | G | T | A | G | T | Y | G | C | A | C | T | C | C | A | S |
| German Nugget | A | C | T | G | T | T | T | A | T | G | T | A | G | T | C | G | C | A | C | T | C | C | A | S |
| Taurus | A | T | K | A | T | Y | D | W | K | R | T | G | G | T | T | R | S | M | Y | Y | Y | M | W | S |

Nucleotide code table

| | | | |
|---|---|---|---|
| A, C, G, or T | N | A or G (purine) | R | Y |
| C, G, or T (not A) | B | C or T (pyrimidine) | | Y |
| A, G, or T (not C) | D | G or T (keto) | | K |
| A, C, or T (not G) | H | A or C (amine) | | M |
| A, C, or G (not T) | V | G or C (strong) | | S |
| | | A or T (weak) | | W |

SNP analysis results in region B1

| Variety to be identified \ SNP position | 178 | 204 | 227 | 234 | 370 | 426 | 439 | 547 | 562 | 624 | type |
|---|---|---|---|---|---|---|---|---|---|---|---|
| Saaz | R | A | R | A | R | M | R | Y | Y | S | a |
| Sladeck | R | A | G | A | R | M | R | Y | Y | S | b |
| Premiant | A | A | G | A | A | C | A | T | T | C | c |
| Tradition | A | A | G | A | A | C | A | Y | T | C | d |
| Spalter | R | A | G | A | R | M | A | T | Y | S | e |
| Spalter Select | R | A | G | A | R | M | R | T | Y | S | f |
| Perle | A | A | G | A | A | C | A | Y | T | C | d |
| Tettnang | R | M | R | R | R | M | A | T | Y | Y | g |
| Brewer's Gold | A | A | G | A | A | C | A | T | T | C | c |
| Northern Brewer | A | A | G | A | A | C | A | Y | T | C | d |
| Magnum | A | A | G | A | A | C | A | Y | T | C | d |
| Herkules | A | A | G | A | A | C | A | Y | T | C | d |
| German Nugget | A | A | G | A | A | C | A | T | T | C | c |
| Taurus | A | A | G | A | A | C | A | Y | T | C | d |

FIG. 3

SNP analysis results in region C1

| SNP position / Variety to be identified | 3 | 13 | 17 | 87 | 88 | 129 | 130 | 131 | 132 | 133 | 134 | 254 | 331 | 356 | 375 | 380 | 396 | 398 | 399 | 421 | 460 | 474 | 475 | 476 | 477 | 480 | 481 | 530 | 547 | type |
|---|---|---|---|---|---|---|---|---|---|---|---|---|---|---|---|---|---|---|---|---|---|---|---|---|---|---|---|---|---|---|
| Saaz | T | C | G | A | G | - | - | - | - | - | - | T | A | G | C | G | T | C | A | A | T | T | A | C | T | A | A | T | A | − |
| Sladeck | T | C | G | A | G | - | - | - | - | - | - | T | A | G | C | G | T | C | A | A | T | T | A | C | T | A | A | T | A | − |
| Premiant | T | C | G | A | G | - | - | - | - | - | - | T | A | G | C | G | T | C | A | A | T | T | A | C | T | A | A | T | A | − |
| Tradition | C | G | T | T | T | C | A | T | G | A | C | C | A | G | A | T | A | C | T | G | C | T | A | C | T | A | G | T | A | ≡ |
| Spalter | T | C | G | A | G | - | - | - | - | - | - | T | A | G | C | G | T | C | A | A | T | T | A | C | T | A | A | T | A | − |
| Spalter Select | C | G | T | T | T | C | A | T | G | A | C | C | A | G | A | T | A | C | T | G | C | T | A | C | T | A | G | T | A | ≡ |
| Perle | T | C | G | A | G | - | - | - | - | - | - | T | A | G | C | G | T | C | A | A | T | T | A | C | T | A | A | T | A | − |
| Tettnang | T | C | G | A | G | - | - | - | - | - | - | T | A | G | C | G | T | C | A | A | T | T | A | C | T | A | A | T | A | − |
| Brew Gold | T | C | G | A | G | - | - | - | - | - | - | T | A | G | C | G | T | C | A | A | T | T | A | C | T | A | A | T | A | − |
| Northern Brewer | T | C | G | A | G | - | - | - | - | - | - | T | A | G | C | G | T | C | A | A | T | T | A | C | T | A | A | T | A | − |
| Magnum | T | G | T | T | T | C | A | T | G | A | C | C | R | R | C | G | Y | S | R | R | C | W | R | M | Y | M | A | K | R | ≡ |
| Herkules | C | C | T | T | T | - | - | - | - | - | - | C | A | G | A | T | A | C | T | G | C | T | A | C | T | A | G | T | A | ≡ |
| German Nugget | T | C | G | A | G | - | - | - | - | - | - | T | A | G | C | G | T | C | A | A | T | T | A | C | T | A | A | T | A | − |
| Taurus | T | C | G | A | G | - | - | - | - | - | - | T | A | G | C | G | T | C | A | A | T | T | A | C | T | A | A | T | A | − |

FIG. 4

SNP analysis results in region A1-2-L (2 varieties to be identified)

| SNP position / Variety to be identified | 34 | 101 | 118 | 124 | 164 | 168 | 171 | 186 | 187 | 188 | 189 | 190 | 191 | 192 | 193 | 194 | 392 | 398 | 399 | 459 | 502 |
|---|---|---|---|---|---|---|---|---|---|---|---|---|---|---|---|---|---|---|---|---|---|
| Perle | A | T | G | T | T | T | T | - | - | - | - | - | - | - | - | - | C | G | - | T | G |
| Northern Brewer | G | A | A | C | C | C | A | T | T | C | T | T | C | T | T | T | T | T | T | C | C |

SNP analysis results in region A1-2-R (2 varieties to be identified)

| SNP position / Variety to be identified | 1 | 2 | 3 | 5 | 8 | 9 | 10 | 11 | 12 | 13 | 14 | 15 | 16 | 17 | 20 | 21 | 25 | 26 | 27 | 28 | 29 | 30 | 31 | 33 | 35 | 36 | 37 | 38 | 41 | 42 | 43 | 44 | 46 | 47 | 48 |
|---|---|---|---|---|---|---|---|---|---|---|---|---|---|---|---|---|---|---|---|---|---|---|---|---|---|---|---|---|---|---|---|---|---|---|---|
| Perle | A | G | C | A | T | C | C | T | G | T | G | C | C | C | C | T | T | G | T | C | G | A | G | T | G | A | G | A | A | C | C | A | A | G | A |
| Northern Brewer | G | C | A | G | - | - | T | T | C | T | A | G | G | T | C | A | C | T | A | T | A | T | A | C | A | T | A | C | T | G | G | G | G | A | T |

| SNP position / Variety to be identified | 50 | 51 | 56 | 57 | 58 | 59 | 63 | 65 | 68 | 72 | 78 | 79 | 84 | 86 | 88 | 90 | 92 | 118 | 153 | 154 | 191 | 205 | 206 | 226 | 228 | 233 | 254 | 289 | 315 | 350 | 392 | 405 |
|---|---|---|---|---|---|---|---|---|---|---|---|---|---|---|---|---|---|---|---|---|---|---|---|---|---|---|---|---|---|---|---|---|
| Perle | A | G | G | T | A | - | T | T | T | T | T | G | A | C | C | T | T | T | A | A | G | C | A | A | G | A | G | A | T | C | T | G |
| Northern Brewer | T | A | C | - | - | C | C | - | C | C | C | A | C | C | T | T | A | A | T | T | A | T | G | G | C | T | A | T | C | T | A | G |

FIG. 5

Summary of identification markers for 14 varieties to be identified

| Country of origin | Variety to be identified | Diplotype | | | | | Possibility/impossibility of identification |
|---|---|---|---|---|---|---|---|
| | | A1 | B1 | C1 | A1-2 | A1+B1+C1 + (A1-2) | |
| Czech | Saaz | 1 | a | i | | A | ○ |
| | Sladeck | 2 | b | i | | B | ○ |
| | Premiant | 2 | c | i | | C | ○ |
| Germany | Tradition | 3 | d | iii | | D | ○ |
| | Spalter | 4 | e | i | | E | ○ |
| | Spalter Select | 2 | f | ii | | F | ○ |
| | Perle | 2 | d | i | α | G | ○ |
| | Tettnang | 5 | g | i | | H | ○ |
| | Brewer's Gold | 7 | c | i | | I | ○ |
| | Northern Brewer | 2 | d | i | β | N | ○ |
| | Magnum | 2 | d | iii | | J | ○ |
| | Herkules | 6 | d | ii | | K | ○ |
| | German Nugget | 9 | c | i | | L | ○ |
| | Taurus | 8 | d | i | | M | ○ |

FIG. 6

SNP analysis results in region A1-2-L (5 varieties to be identified)

| Variety to be identified \ SNP position | 2 | 12 | 31 | 98 | 115 | 121 | 161 | 165 | 168 | 183 | 184 | 185 | 186 | 187 | 188 | 189 | 190 | 191 | 389 | 395 | 396 | 456 | 499 | type |
|---|---|---|---|---|---|---|---|---|---|---|---|---|---|---|---|---|---|---|---|---|---|---|---|---|
| Sladeck | T | - | A | T | G | T | T | T | T | - | - | - | - | - | - | - | - | - | C | G | - | T | G | (1) |
| Spalter | T | - | G | A | A | C | C | C | C | T | T | C | T | T | C | T | T | C | T | T | T | C | C | (2) |
| Perle | T | A | A | T | G | T | T | T | T | - | - | - | - | - | - | - | - | - | C | G | - | T | G | (3) |
| Tettnang | A | - | G | A | A | C | C | C | C | T | T | C | T | T | C | T | T | C | T | T | T | C | C | (4) |
| Northern Brewer | T | A | G | A | A | C | C | C | A | T | T | C | T | T | C | T | T | C | T | T | T | C | C | (5) |

SNP analysis results in region A1-2-R (5 varieties to be identified)

| Variety to be identified \ SNP position | 2 | 6 | 12 | 13 | 18 | 20 | 22 | 24 | 26 | 36 | 52 | 87 | 88 | 125 | 139 | 140 | 160 | 162 | 167 | 188 | 223 | 249 | 273 | 284 | 326 | 339 | 421 | 437 | type |
|---|---|---|---|---|---|---|---|---|---|---|---|---|---|---|---|---|---|---|---|---|---|---|---|---|---|---|---|---|---|
| Sladeck | T | C | T | G | T | T | T | T | T | G | T | A | A | A | G | G | C | G | A | A | A | C | A | A | A | G | G | T | (a) |
| Spalter | C | C | C | A | C | C | C | C | C | T | A | T | T | G | A | A | T | A | T | T | T | A | T | T | G | G | G | T | (b) |
| Perle | T | T | T | G | T | T | T | T | T | T | T | A | A | A | G | G | C | G | A | A | A | C | A | T | A | G | T | T | (c) |
| Tettnang | C | C | C | A | C | C | C | C | C | T | A | T | A | A | A | A | T | A | T | T | T | A | T | G | G | G | G | T | (b) |
| Northern Brewer | C | C | C | A | C | C | C | C | C | T | A | T | T | A | A | A | T | A | T | T | T | A | T | G | G | G | G | T | (d) |

Summary of identification markers for 5 varieties to be identified

| Country of origin | Variety to be identified | Diplotype A1-2-L | Possibility/ impossibility |
|---|---|---|---|
| Czech | Sladeck | (1) | ○ |
| Germany | Spalter | (2) | ○ |
| | Perle | (3) | ○ |
| | Tettnang | (4) | ○ |
| | Northern Brewer | (5) | ○ |

FIG. 7

SEQUENCE LISTING

```
<160> NUMBER OF SEQ ID NOS: 110

<210> SEQ ID NO 1
<211> LENGTH: 20
<212> TYPE: DNA
<213> ORGANISM: Artificial sequence
<220> FEATURE:
<223> OTHER INFORMATION: Primer A1-3L

<400> SEQUENCE: 1
taaggtgttg ggagggttga                                              20

<210> SEQ ID NO 2
<211> LENGTH: 20
<212> TYPE: DNA
<213> ORGANISM: Artificial sequence
<220> FEATURE:
<223> OTHER INFORMATION: Primer A1-3R

<400> SEQUENCE: 2
ccaccaataa caggctccac                                              20

<210> SEQ ID NO 3
<211> LENGTH: 21
<212> TYPE: DNA
<213> ORGANISM: Artificial sequence
<220> FEATURE:
<223> OTHER INFORMATION: Primer B1-1L

<400> SEQUENCE: 3
cagacttgtg gctgtcaaaa a                                            21
```

-continued

<210> SEQ ID NO 4
<211> LENGTH: 20
<212> TYPE: DNA
<213> ORGANISM: Artificial sequence
<220> FEATURE:
<223> OTHER INFORMATION: Primer B1-1R

<400> SEQUENCE: 4
cttctccttc gaacctgtcg                                               20

<210> SEQ ID NO 5
<211> LENGTH: 20
<212> TYPE: DNA
<213> ORGANISM: Artificial sequence
<220> FEATURE:
<223> OTHER INFORMATION: Primer C1-1L

<400> SEQUENCE: 5
cggcgttttt caattttcat                                               20

<210> SEQ ID NO 6
<211> LENGTH: 20
<212> TYPE: DNA
<213> ORGANISM: Artificial sequence
<220> FEATURE:
<223> OTHER INFORMATION: Primer C1-1R

<400> SEQUENCE: 6
gtgatgactc gggcttcagt                                               20

<210> SEQ ID NO 7
<211> LENGTH: 23
<212> TYPE: DNA
<213> ORGANISM: Artificial sequence
<220> FEATURE:
<223> OTHER INFORMATION: Primer A1-2-1L

<400> SEQUENCE: 7
gaaatctgct tkgagaaacc tgg                                           23

<210> SEQ ID NO 8
<211> LENGTH: 23
<212> TYPE: DNA
<213> ORGANISM: Artificial sequence
<220> FEATURE:
<223> OTHER INFORMATION: Primer A1-2-1R

<400> SEQUENCE: 8
gcaggtatct ttgtaggtac atc                                           23

<210> SEQ ID NO 9
<211> LENGTH: 541
<212> TYPE: DNA
<213> ORGANISM: Humulus lupulus
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (103)..(103)

```
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (134)..(135)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (203)..(204)
<223> OTHER INFORMATION: n is a, c, g, or t
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
<222> LOCATION: (230)..(230)
<223> OTHER INFORMATION: n is a, c, g, or t
<220> FEATURE:
<221> NAME/KEY: misc_feature
<222> LOCATION: (235)..(235)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (316)..(316)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t

<400> SEQUENCE: 9
tggtggtgca gaaaagtcag gattttgatg gtggggagtc agagtttagg gccagtgagg      60
aggtagaagt agangangGt aaaattntgg atggtgggaa tgntaaagat aactcngnca    120
```

```
ntttngaaga gaannatgag aagttggncg aagaagatgg ggtgagtctt ggcggagatg    180
agtcagtggt gnaancngng cannttaatg tcccagcttc aagagnagcn gatgntggag    240
tttcagaaga acttgatgaa gctgaaatta gaggtgtaga gcctccagga ggcgggaacc    300
ttggcnctgg ttctgnagaa tttgttggcn caaagttgat gcctacagat tctgaatctg    360
atggaaatgt tgtggggtct gttactggtg gtcctgatga agttgatacc aagcacgtat    420
cagcaggaga agatggtggg ctaaaagcta attctgaagt tcatcagagc ggccccgtgg    480
tcgagaaagg tgctgataat gaaaaagttc tgtcaggtga tggagttggt cnaaagttga    540
t                                                                    541
```

```
<210> SEQ ID NO 10
<211> LENGTH: 645
<212> TYPE: DNA
<213> ORGANISM: Humulus lupulus
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (562)..(562)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t

<400> SEQUENCE: 10
cattcctcag gatctaaagc gaattattaa gaaatacatt caaatgagat tgcaagatgg     60
aaaagatgtg gacatcgacc atattttgca tattcttcct ttgtcacagg gaatgctaat    120
taagaaacac atgtgtttcc ctatgttaaa aaaagtaagt tatcttttat agtatatnta    180
tgtcattatt aagtttgatc tttnatttga gctataacat agtattntta tttnattgat    240
tgattgatta tatgattaat tataggttcc attatttcaa aacacggatg aacatgttta    300
cgaaacaata tgcaaatatc tgaaaccagt cacatattca gagaaaagtt atatcattcg    360
aaaaggagan ccacttgata tgattctctt catcacacaa ggtgttgtgt gggcatttgg    420
```

-continued

```
aaatgntact actcccatna gtcgacttca aaaaggtgat ttctatggaa atgaactcat    480
agaatggcaa ttaaagtcaa catccattga tgagtttcct atttcggttg ctaatcttaa    540
atcccanacc aatgttgaag cncttgctct tatggccaat gacttggaac atgtagtctc    600
caattgctgg ttcaagttct cccncacctg ctcatctatg cctga                   645
```

```
<210> SEQ ID NO 11
<211> LENGTH: 559
<212> TYPE: DNA
<213> ORGANISM: Humulus lupulus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (87)..(88)
<223> OTHER INFORMATION: n is a, c, g, or t
<220> FEATURE:
<221> NAME/KEY: misc_feature
<222> LOCATION: (129)..(134)
<223> OTHER INFORMATION: n is a, c, g, t, or no nucleobase (deletion)
<220> FEATURE:
<221> NAME/KEY: misc_feature
<222> LOCATION: (254)..(254)
<223> OTHER INFORMATION: n is a, c, g, or t
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (380)..(380)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (398)..(399)
<223> OTHER INFORMATION: n is a, c, g, or t
<220> FEATURE:
<221> NAME/KEY: misc_feature
<222> LOCATION: (421)..(421)
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (474)..(477)
<223> OTHER INFORMATION: n is a, c, g, or t
<220> FEATURE:
<221> NAME/KEY: misc_feature
<222> LOCATION: (480)..(481)
<223> OTHER INFORMATION: n is a, c, g, or t
<220> FEATURE:
<221> NAME/KEY: misc_feature
```

<222> LOCATION: (500)..(500)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t

<400> SEQUENCE: 11

```
ttngacgtga tcnagtngag tggtggtata tacgttccat attataaaga ttacattgtt      60
ttaatggata taccagggaa ggagaannta aaactctcca tcgcactgca agccaacccc     120
gatgatacnn nnnntttgta cactgatgcc atcttgaatg gcatcgaaat cttcaaatta     180
agcgactcca acggaaatct cgccggtctg aatcttgacc ttgttccgca tgcgaagcca     240
ccaagccaac catnatggaa gttgaaaaat catcaatcag agattattgg catttccatt     300
ggtgtagttt gcagcgttgt tttgctctgc ntaattggat tcctatttct ccggcnaggt     360
agaaaagtca aaggnacaan gctcatttcc ttgtcnanna ccaggtcaag caagaccgga     420
naatcatcat tgccgttgga tcggtgtcgt tactttcan tggctgagat catnnnngcn      480
ncaaacaact tcgaagatan tttcattatt ggggttggag gattcggaaa cgtgtataaa     540
gggcacntcg acaatggga                                                  559
```

<210> SEQ ID NO 12
<211> LENGTH: 538
<212> TYPE: DNA
<213> ORGANISM: Humulus lupulus
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (186)..(194)
<223> OTHER INFORMATION: n is a, c, g, t, or no nucleobase (deletion)
<220> FEATURE:
<221> NAME/KEY: misc_feature
<222> LOCATION: (392)..(392)
<223> OTHER INFORMATION: n is a, c, g, or t
<220> FEATURE:
<221> NAME/KEY: misc_feature
<222> LOCATION: (398)..(398)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, t, or no nucleobase (deletion)
<220> FEATURE:

-continued

<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (502)..(502)
<223> OTHER INFORMATION: n is a, c, g, or t

<400> SEQUENCE: 12

```
cagctgagct tgaaagttat ggctatcgcc gccnccattt cgggtcctct gacaactccg    60
tctcggcggc gctcagtcac ctccttcagc tcactctcca nttctcattc tcttacgnga   120
caantgagtt ttctcagagc aagtcgcccc tgtattggct tgtnagcnac ngcttcttct   180
tcttcnnnnn nnnncatttc catgagtctc gaagccgccg agaaggcctc gccggtgtcg   240
ttcttggatc gcagggagac cggttttctt cattttgtca agtaccacgg cgtcggcaat   300
gacttcatct tggtaaactc gaaaatggag ctagttttc tctatagagg aaaagaaaga   360
atttttttct tctaaattta ttgagtagtc tntttttnna ttgatgtagg ttgataatag   420
ggattcttca gagcctagga ttactcccga gcaagcgggn aagctctgtg atcggaactt   480
tggaattgga gctgatgggg tnatttttgc tatgcctggc atcaatggca ctgactac    538
```

<210> SEQ ID NO 13
<211> LENGTH: 535
<212> TYPE: DNA
<213> ORGANISM: Humulus lupulus
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, t, or no nucleobase (deletion)
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (183)..(191)
<223> OTHER INFORMATION: n is a, c, g, t, or no nucleobase (deletion)
<220> FEATURE:
<221> NAME/KEY: misc_feature
<222> LOCATION: (389)..(389)
<223> OTHER INFORMATION: n is a, c, g, or t
<220> FEATURE:
<221> NAME/KEY: misc_feature
<222> LOCATION: (395)..(395)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, t, or no nucleobase (deletion)
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (499)..(499)
<223> OTHER INFORMATION: n is a, c, g, or t

<400> SEQUENCE: 13

```
cngagcttga angttatggc tatcgccgcc nccatttcgg gtcctctgac aactccgtct      60
cggcggcgct cagtcacctc cttcagctca ctctccantt ctcattctct tacgngacaa     120
ntgagttttc tcagagcaag tcgcccctgt attggcttgt nagcnacngc ttcttcttct     180
tcnnnnnnnn ncatttccat gagtctcgaa gccgccgaga aggcctcgcc ggtgtcgttc     240
ttggatcgca gggagaccgg ttttcttcat tttgtcaagt accacggcgt cggcaatgac     300
ttcatcttgg taaactcgaa aatggagcta gttttctct atagaggaaa agaaagaatt      360
tttttcttct aaatttattg agtagtctnt ttttnnattg atgtaggttg ataataggga     420
ttcttcagag cctaggatta ctcccgagca agcggngaag ctctgtgatc ggaactttgg     480
aattggagct gatggggtna tttttgctat gcctggcatc aatggcactg actac          535
```

<210> SEQ ID NO 14
<211> LENGTH: 516
<212> TYPE: DNA
<213> ORGANISM: Humulus lupulus
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(17)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (25)..(31)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (35)..(38)
<223> OTHER INFORMATION: n is a, c, g, or t
<220> FEATURE:
<221> NAME/KEY: misc_feature
<222> LOCATION: (41)..(44)
<223> OTHER INFORMATION: n is a, c, g, or t
<220> FEATURE:
<221> NAME/KEY: misc_feature
<222> LOCATION: (46)..(48)
<223> OTHER INFORMATION: n is a, c, g, or t
<220> FEATURE:
<221> NAME/KEY: misc_feature
<222> LOCATION: (50)..(51)

```
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (57)..(59)
<223> OTHER INFORMATION: n is a, c, g, t, or no nucleobase (deletion)
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, t, or no nucleobase (deletion)
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (78)..(79)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (153)..(154)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (205)..(206)
<223> OTHER INFORMATION: n is a, c, g, or t
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
```

<222> LOCATION: (254)..(254)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (392)..(392)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t

<400> SEQUENCE: 14

```
nnnangannn nnnnnnngan ntatnnnnnn ncntnnnnat nnnnannnan ncacannnna    60
canancanac anacacannc acanananan anatatacat ataatgtaaa tgttgatnct   120
ctattgtgat gatttgcttc tgaaacatga tannagaaac aataaaaaga acaaagaagt   180
attggttatt nggaagacct ctttnngatt tctttgacaa tgcctntntg ttntattgat   240
gtagctttac tgtncatact ggtgctggtc taattattcc agaaatacna gatgatggtc   300
aggtataaac ttctntactt gcaaattacc taaatctatt gggttcatan gcttcaaaag   360
caacattcat aaatgattgc attttgctac anttatggca gtttngcttc taatctggat   420
ttgttgaagt tgccaaacta ctggatagcg attttttgagt attcaattta gcagggggtgc  480
tgttttgatt tcaggtcaaa gttgatatgg gtgaaa                             516
```

<210> SEQ ID NO 15
<211> LENGTH: 443
<212> TYPE: DNA
<213> ORGANISM: Humulus lupulus
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (26)..(26)

```
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (87)..(88)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (139)..(140)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (167)..(167)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (223)..(223)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (326)..(326)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (421)..(421)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, t, or no nucleobase (deletion)

<400> SEQUENCE: 15
anacanacac anncacanan anananatat acatanaatg taaatgttga tnctctattg      60
tgatgatttg cttctgaaac atgatannag aaacaataaa aagaacaaag aagtattggt     120
tattnggaag acctctttnn gatttctttg acaatgcctn tntgttntat tgatgtagct     180
ttactgtnca tactggtgct ggtctaatta ttccagaaat acnagatgat ggtcaggtat     240
```

| | |
|---|---|
| aaacttctnt acttgcaaat tacctaaatc tantgggttc atangcttca aaagcaacat | 300 |
| tcataaatga ttgcattttg ctacanttat ggcagtttng cttctaatct ggatttgttg | 360 |
| aagttgccaa actactggat agcgattttt gagtattcaa tttagcaggg gtgctgtttt | 420 |
| natttcaggt caaagtngat atg | 443 |

<210> SEQ ID NO 16
<211> LENGTH: 541
<212> TYPE: DNA
<213> ORGANISM: Humulus lupulus

<400> SEQUENCE: 16

| | |
|---|---|
| tggtggtgca gaaaagtcag gattttgatg gtggggagtc agagtttagg gccagtgagg | 60 |
| aggtagaagt agawgatggt aaaattktgg atggtgggaa tgataaagat aactcwgyca | 120 |
| wtttwgaaga gaakratgag aagttggycg aagaagatgg ggtgagtctt ggcggagatg | 180 |
| agtcagtggt ggaakcwgtg carsttaatg tcccagcttc aagagmagcy gatgytggag | 240 |
| tttcagaaga acttgatgaa gctgaaatta gaggtgtaga gcctccagga ggcgggaacc | 300 |
| ttggcyctgg ttctgmagaa tttgttggct caaagttgat gcctacagat tctgaatctg | 360 |
| atggaaatgt tgtggggtct gttactggtg gtcctgatga agttgatacc aagcacgtat | 420 |
| cagcaggaga agatggtggg ctaaaagcta attctgaagt tcatcagagc ggccccgtgg | 480 |
| tcgagaaagg tgctgataat gaaaaagttc tgtcaggtga tgggagttggt cgaaagttga | 540 |
| t | 541 |

<210> SEQ ID NO 17
<211> LENGTH: 541
<212> TYPE: DNA
<213> ORGANISM: Humulus lupulus

<400> SEQUENCE: 17

| | |
|---|---|
| tggtggtgca gaaaagtcag gattttgatg gtggggagtc agagtttagg gccagtgagg | 60 |
| aggtagaagt agaagacggt aaaattttgg atggtgggaa tggtaaagat aactctgtca | 120 |
| ttttagaaga gaatgatgag aagttggtcg aagaagatgg ggtgagtctt ggcggagatg | 180 |
| agtcagtggt gaaagctgcg cagcttaatg tcccagcttc aagagaagcc gatgttggag | 240 |
| tttcagaaga acttgatgaa gctgaaatta gaggtgtaga gcctccagga ggcgggaacc | 300 |
| ttggccctgg ttctgcagaa tttgttggca caaagttgat gcctacagat tctgaatctg | 360 |
| atggaaatgt tgtggggtct gttactggtg gtcctgatga agttgatacc aagcacgtat | 420 |
| cagcaggaga agatggtggg ctaaaagcta attctgaagt tcatcagagc ggccccgtgg | 480 |
| tcgagaaagg tgctgataat gaaaaagttc tgtcaggtga tgggagttggt ccaaagttga | 540 |
| t | 541 |

<210> SEQ ID NO 18
<211> LENGTH: 541
<212> TYPE: DNA
<213> ORGANISM: Humulus lupulus

<400> SEQUENCE: 18

| | |
|---|---|
| tggtggtgca gaaaagtcag gattttgatg gtggggagtc agagtttagg gccagtgagg | 60 |
| aggtagaagt agaagacggt aaaattttgg atggtgggaa tggtaaagat aactctgtca | 120 |
| ttttagaaga gaatgatgag aagttggtcg aagaagatgg ggtgagtctt ggcggagatg | 180 |

```
agtcagtggt gaaagctgcg cagcttaatg tcccagcttc aagagaagcc gatgttggag      240
tttcagaaga acttgatgaa gctgaaatta gaggtgtaga gcctccagga ggcgggaacc      300
ttggccctgg ttctgcagaa tttgttggca caaagttgat gcctacagat tctgaatctg      360
atggaaatgt tgtggggtct gttactggtg gtcctgatga agttgatacc aagcacgtat      420
cagcaggaga agatggtggg ctaaaagcta attctgaagt tcatcagagc ggccccgtgg      480
tcgagaaagg tgctgataat gaaaaagttc tgtcaggtga tggagttggt ccaaagttga      540
t                                                                    541
```

<210> SEQ ID NO 19
<211> LENGTH: 541
<212> TYPE: DNA
<213> ORGANISM: Humulus lupulus

<400> SEQUENCE: 19

```
tggtggtgca gaaaagtcag gattttgatg gtggggagtc agagtttagg gccagtgagg      60
aggtagaagt agawgatggt aaaattktgg atggtgggaa tgataaagat aactcwgyca      120
wtttwgaaga gaakratgag aagttggycg aagaagatgg ggtgagtctt ggcggagatg      180
agtcagtggt ggaakcwgtg carsttaatg tcccagcttc aagagmagcy gatgytggag      240
tttcagaaga acttgatgaa gctgaaatta gaggtgtaga gcctccagga ggcgggaacc      300
ttggcyctgg ttctgcagaa tttgttggcw caaagttgat gcctacagat tctgaatctg      360
atggaaatgt tgtggggtct gttactggtg gtcctgatga agttgatacc aagcacgtat      420
cagcaggaga agatggtggg ctaaaagcta attctgaagt tcatcagagc ggccccgtgg      480
tcgagaaagg tgctgataat gaaaaagttc tgtcaggtga tggagttggt cgaaagttga      540
t                                                                    541
```

<210> SEQ ID NO 20
<211> LENGTH: 541
<212> TYPE: DNA
<213> ORGANISM: Humulus lupulus

<400> SEQUENCE: 20

```
tggtggtgca gaaaagtcag gattttgatg gtggggagtc agagtttagg gccagtgagg      60
aggtagaagt agawgatggt aaaattktgg atggtgggaa tgataaagat aactcwgyca      120
wtttwgaaga gaakratgag aagttggycg aagaagatgg ggtgagtctt ggcggagatg      180
agtcagtggt ggaakcwgtg carsttaatg tcccagcttc aagagmagcy gatgytggag      240
tttcagaaga acttgatgaa gctgaaatta gaggtgtaga gcctccagga ggcgggaacc      300
ttggcyctgg ttctgmagaa tttgttggcw caaagttgat gcctacagat tctgaatctg      360
atggaaatgt tgtggggtct gttactggtg gtcctgatga agttgatacc aagcacgtat      420
cagcaggaga agatggtggg ctaaaagcta attctgaagt tcatcagagc ggccccgtgg      480
tcgagaaagg tgctgataat gaaaaagttc tgtcaggtga tggagttggt cgaaagttga      540
t                                                                    541
```

<210> SEQ ID NO 21
<211> LENGTH: 541
<212> TYPE: DNA
<213> ORGANISM: Humulus lupulus

<400> SEQUENCE: 21

```
tggtggtgca gaaaagtcag gattttgatg gtggggagtc agagtttagg gccagtgagg      60
```

```
aggtagaagt agaagacggt aaaattttgg atggtgggaa tggtaaagat aactctgtca      120
ttttagaaga gaatgatgag aagttggtcg aagaagatgg ggtgagtctt ggcggagatg      180
agtcagtggt gaaagctgcg cagcttaatg tcccagcttc aagagaagcc gatgttggag      240
tttcagaaga acttgatgaa gctgaaatta gaggtgtaga gcctccagga ggcgggaacc      300
ttggccctgg ttctgcagaa tttgttggca caaagttgat gcctacagat tctgaatctg      360
atggaaatgt tgtggggtct gttactggtg gtcctgatga agttgatacc aagcacgtat      420
cagcaggaga agatggtggg ctaaaagcta attctgaagt tcatcagagc ggccccgtgg      480
tcgagaaagg tgctgataat gaaaaagttc tgtcaggtga tggagttggt ccaaagttga      540
t                                                                     541

<210> SEQ ID NO 22
<211> LENGTH: 541
<212> TYPE: DNA
<213> ORGANISM: Humulus lupulus

<400> SEQUENCE: 22
tggtggtgca gaaaagtcag gattttgatg gtggggagtc agagtttagg gccagtgagg       60
aggtagaagt agaagacggt aaaattttgg atggtgggaa tggtaaagat aactctgtca      120
ttttagaaga gaatgatgag aagttggtcg aagaagatgg ggtgagtctt ggcggagatg      180
agtcagtggt gaaagctgcg cagcttaatg tcccagcttc aagagaagcc gatgttggag      240
tttcagaaga acttgatgaa gctgaaatta gaggtgtaga gcctccagga ggcgggaacc      300
ttggccctgg ttctgcagaa tttgttggca caaagttgat gcctacagat tctgaatctg      360
atggaaatgt tgtggggtct gttactggtg gtcctgatga agttgatacc aagcacgtat      420
cagcaggaga agatggtggg ctaaaagcta attctgaagt tcatcagagc ggccccgtgg      480
tcgagaaagg tgctgataat gaaaaagttc tgtcaggtga tggagttggt ccaaagttga      540
t                                                                     541

<210> SEQ ID NO 23
<211> LENGTH: 541
<212> TYPE: DNA
<213> ORGANISM: Humulus lupulus

<400> SEQUENCE: 23
tggtggtgca gaaaagtcag gattttgatg gtggggagtc agagtttagg gccagtgagg       60
aggtagaagt agawgatggt aaaattktgg atggtgggaa tgataaagat aactcwgyca      120
wtttwgaaga gaakratgag aagttggtcg aagaagatgg ggtgagtctt ggcggagatg      180
agtcagtggt ggaakcwgtg carsttaatg tcccagcttc aagagcagcy gatgytggag      240
tttcagaaga acttgatgaa gctgaaatta gaggtgtaga gcctccagga ggcgggaacc      300
ttggcyctgg ttctgmagaa tttgttggcw caaagttgat gcctacagat tctgaatctg      360
atggaaatgt tgtggggtct gttactggtg gtcctgatga agttgatacc aagcacgtat      420
cagcaggaga agatggtggg ctaaaagcta attctgaagt tcatcagagc ggccccgtgg      480
tcgagaaagg tgctgataat gaaaaagttc tgtcaggtga tggagttggt cgaaagttga      540
t                                                                     541

<210> SEQ ID NO 24
<211> LENGTH: 541
<212> TYPE: DNA
```

<213> ORGANISM: Humulus lupulus

<400> SEQUENCE: 24

| | |
|---|---|
| tggtggtgca gaaaagtcag gattttgatg gtggggagtc agagtttagg gccagtgagg | 60 |
| aggtagaagt agaagatggt aaaattktgg atggtgggaa tgataaagat aactctgtca | 120 |
| wtttwgaaga gaakratgag aagttggtcg aagaagatgg ggtgagtctt ggcggagatg | 180 |
| agtcagtggt ggaagctgtg carsttaatg tcccagcttc aagagmagcy gatgttggag | 240 |
| tttcagaaga acttgatgaa gctgaaatta gaggtgtaga gcctccagga ggcgggaacc | 300 |
| ttggcyctgg ttctgmagaa tttgttggcw caaagttgat gcctacagat tctgaatctg | 360 |
| atggaaatgt tgtggggtct gttactggtg gtcctgatga agttgatacc aagcacgtat | 420 |
| cagcaggaga agatggtggg ctaaaagcta attctgaagt tcatcagagc ggccccgtgg | 480 |
| tcgagaaagg tgctgataat gaaaaagttc tgtcaggtga tggagttggt csaaagttga | 540 |
| t | 541 |

<210> SEQ ID NO 25
<211> LENGTH: 541
<212> TYPE: DNA
<213> ORGANISM: Humulus lupulus

<400> SEQUENCE: 25

| | |
|---|---|
| tggtggtgca gaaaagtcag gattttgatg gtggggagtc agagtttagg gccagtgagg | 60 |
| aggtagaagt agaagacggt aaaattttgg atggtgggaa tggtaaagat aactctgtca | 120 |
| ttttagaaga gaatgatgag aagttggtcg aagaagatgg ggtgagtctt ggcggagatg | 180 |
| agtcagtggt gaaagctgcg cagcttaatg tcccagcttc aagagaagcc gatgttggag | 240 |
| tttcagaaga acttgatgaa gctgaaatta gaggtgtaga gcctccagga ggcgggaacc | 300 |
| ttggccctgg ttctgcagaa tttgttggca caaagttgat gcctacagat tctgaatctg | 360 |
| atggaaatgt tgtggggtct gttactggtg gtcctgatga agttgatacc aagcacgtat | 420 |
| cagcaggaga agatggtggg ctaaaagcta attctgaagt tcatcagagc ggccccgtgg | 480 |
| tcgagaaagg tgctgataat gaaaaagttc tgtcaggtga tggagttggt ccaaagttga | 540 |
| t | 541 |

<210> SEQ ID NO 26
<211> LENGTH: 541
<212> TYPE: DNA
<213> ORGANISM: Humulus lupulus

<400> SEQUENCE: 26

| | |
|---|---|
| tggtggtgca gaaaagtcag gattttgatg gtggggagtc agagtttagg gccagtgagg | 60 |
| aggtagaagt agaagacggt aaaattttgg atggtgggaa tggtaaagat aactctgtca | 120 |
| ttttagaaga gaatgatgag aagttggtcg aagaagatgg ggtgagtctt ggcggagatg | 180 |
| agtcagtggt gaaagctgcg cagcttaatg tcccagcttc aagagaagcc gatgttggag | 240 |
| tttcagaaga acttgatgaa gctgaaatta gaggtgtaga gcctccagga ggcgggaacc | 300 |
| ttggccctgg ttctgcagaa tttgttggca caaagttgat gcctacagat tctgaatctg | 360 |
| atggaaatgt tgtggggtct gttactggtg gtcctgatga agttgatacc aagcacgtat | 420 |
| cagcaggaga agatggtggg ctaaaagcta attctgaagt tcatcagagc ggccccgtgg | 480 |
| tcgagaaagg tgctgataat gaaaaagttc tgtcaggtga tggagttggt ccaaagttga | 540 |
| t | 541 |

<210> SEQ ID NO 27
<211> LENGTH: 541
<212> TYPE: DNA
<213> ORGANISM: Humulus lupulus

<400> SEQUENCE: 27

```
tggtggtgca gaaaagtcag gattttgatg gtggggagtc agagtttagg gccagtgagg      60
aggtagaagt agaagacggt aaaattttgg atggtgggaa tggtaaagat aactctgtca     120
ttttagaaga gaatgatgag aagttggtcg aagaagatgg ggtgagtctt ggcggagatg     180
agtcagtggt graagctgyg cagcttaatg tcccagcttc aagagaagcc gatgttggag     240
tttcagaaga acttgatgaa gctgaaatta gaggtgtaga gcctccagga ggcgggaacc     300
ttggccctgg ttctgcagaa tttgttggca caaagttgat gcctacagat tctgaatctg     360
atggaaatgt tgtggggtct gttactggtg gtcctgatga agttgatacc aagcacgtat     420
cagcaggaga agatggtggg ctaaaagcta attctgaagt tcatcagagc ggccccgtgg     480
tcgagaaagg tgctgataat gaaaaagttc tgtcaggtga tggagttggt csaaagttga     540
t                                                                     541
```

<210> SEQ ID NO 28
<211> LENGTH: 541
<212> TYPE: DNA
<213> ORGANISM: Humulus lupulus

<400> SEQUENCE: 28

```
tggtggtgca gaaaagtcag gattttgatg gtggggagtc agagtttagg gccagtgagg      60
aggtagaagt agaagacggt aaaattttgg atggtgggaa tggtaaagat aactctgtca     120
ttttagaaga gaatgatgag aagttggtcg aagaagatgg ggtgagtctt ggcggagatg     180
agtcagtggt gaaagctgcg cagcttaatg tcccagcttc aagagaagcc gatgttggag     240
tttcagaaga acttgatgaa gctgaaatta gaggtgtaga gcctccagga ggcgggaacc     300
ttggccctgg ttctgcagaa tttgttggca caaagttgat gcctacagat tctgaatctg     360
atggaaatgt tgtggggtct gttactggtg gtcctgatga agttgatacc aagcacgtat     420
cagcaggaga agatggtggg ctaaaagcta attctgaagt tcatcagagc ggccccgtgg     480
tcgagaaagg tgctgataat gaaaaagttc tgtcaggtga tggagttggt csaaagttga     540
t                                                                     541
```

<210> SEQ ID NO 29
<211> LENGTH: 541
<212> TYPE: DNA
<213> ORGANISM: Humulus lupulus

<400> SEQUENCE: 29

```
tggtggtgca gaaaagtcag gattttgatg gtggggagtc agagtttagg gccagtgagg      60
aggtagaagt agaagatggt aaaattktgg atggtgggaa tgataaagat aactctgyca     120
dtttwgaaga gaakratgag aagttggtcg aagaagatgg ggtgagtctt ggcggagatg     180
agtcagtggt ggaagctgtg carsttaatg tcccagcttc aagagmagcy gatgytggag     240
tttcagaaga acttgatgaa gctgaaatta gaggtgtaga gcctccagga ggcgggaacc     300
ttggcyctgg ttctgmagaa tttgttggcw caaagttgat gcctacagat tctgaatctg     360
atggaaatgt tgtggggtct gttactggtg gtcctgatga agttgatacc aagcacgtat     420
```

```
cagcaggaga agatggtggg ctaaaagcta attctgaagt tcatcagagc ggccccgtgg     480
tcgagaaagg tgctgataat gaaaaagttc tgtcaggtga tggagttggt csaaagttga     540
t                                                                    541
```

<210> SEQ ID NO 30
<211> LENGTH: 645
<212> TYPE: DNA
<213> ORGANISM: Humulus lupulus

<400> SEQUENCE: 30

```
cattcctcag gatctaaagc gaattattaa gaaatacatt caaatgagat tgcaagatgg      60
aaaagatgtg gacatcgacc atattttgca tattcttcct ttgtcacagg gaatgctaat     120
taagaaacac atgtgtttcc ctatgttaaa aaaagtaagt tatctttttat agtatatrta    180 tgtcattatt aagtttgatc tttaatttga gctataacat agtattrtta tttaattgat    240
tgattgatta tatgattaat tataggttcc attatttcaa aacacggatg aacatgttta    300
cgaaacaata tgcaaatatc tgaaaccagt cacatattca gagaaaagtt atatcattcg    360
aaaaggagar ccacttgata tgattctctt catcacacaa ggtgttgtgt gggcatttgg    420
aaatgmtact actcccatra gtcgacttca aaaaggtgat ttctatggaa atgaactcat    480
agaatggcaa ttaaagtcaa catccattga tgagtttcct atttcggttg ctaatcttaa    540
atcccayacc aatgttgaag cycttgctct tatggccaat gacttggaac atgtagtctc    600
caattgctgg ttcaagttct cccscacctg ctcatctatg cctga                    645
```

<210> SEQ ID NO 31
<211> LENGTH: 645
<212> TYPE: DNA
<213> ORGANISM: Humulus lupulus

<400> SEQUENCE: 31

```
cattcctcag gatctaaagc gaattattaa gaaatacatt caaatgagat tgcaagatgg      60
aaaagatgtg gacatcgacc atattttgca tattcttcct ttgtcacagg gaatgctaat     120
taagaaacac atgtgtttcc ctatgttaaa aaaagtaagt tatctttttat agtatatrta    180 tgtcattatt aagtttgatc tttaatttga gctataacat agtattgtta tttaattgat    240
tgattgatta tatgattaat tataggttcc attatttcaa aacacggatg aacatgttta    300
cgaaacaata tgcaaatatc tgaaaccagt cacatattca gagaaaagtt atatcattcg    360
aaaaggagar ccacttgata tgattctctt catcacacaa ggtgttgtgt gggcatttgg    420
aaatgmtact actcccatra gtcgacttca aaaaggtgat ttctatggaa atgaactcat    480
agaatggcaa ttaaagtcaa catccattga tgagtttcct atttcggttg ctaatcttaa    540
atcccayacc aatgttgaag cycttgctct tatggccaat gacttggaac atgtagtctc    600
caattgctgg ttcaagttct cccscacctg ctcatctatg cctga                    645
```

<210> SEQ ID NO 32
<211> LENGTH: 645
<212> TYPE: DNA
<213> ORGANISM: Humulus lupulus

<400> SEQUENCE: 32

```
cattcctcag gatctaaagc gaattattaa gaaatacatt caaatgagat tgcaagatgg      60
aaaagatgtg gacatcgacc atattttgca tattcttcct ttgtcacagg gaatgctaat     120
taagaaacac atgtgtttcc ctatgttaaa aaaagtaagt tatctttttat agtatatata    180
```

```
tgtcattatt aagtttgatc tttaatttga gctataacat agtattgtta tttaattgat      240
tgattgatta tatgattaat tataggttcc attatttcaa aacacggatg aacatgttta      300
cgaaacaata tgcaaatatc tgaaaccagt cacatattca gagaaaagtt atatcattcg      360
aaaaggagaa ccacttgata tgattctctt catcacacaa ggtgttgtgt gggcatttgg      420
aaatgctact actcccataa gtcgacttca aaaaggtgat ttctatggaa atgaactcat      480
agaatggcaa ttaaagtcaa catccattga tgagtttcct atttcggttg ctaatcttaa      540
atcccatacc aatgttgaag ctcttgctct tatggccaat gacttggaac atgtagtctc      600
caattgctgg ttcaagttct cccccacctg ctcatctatg cctga                     645

<210> SEQ ID NO 33
<211> LENGTH: 645
<212> TYPE: DNA
<213> ORGANISM: Humulus lupulus

<400> SEQUENCE: 33
cattcctcag gatctaaagc gaattattaa gaaatacatt caaatgagat tgcaagatgg      60
aaaagatgtg gacatcgacc atattttgca tattcttcct ttgtcacagg gaatgctaat      120
taagaaacac atgtgtttcc ctatgttaaa aaaagtaagt tatcttttat agtatatata      180
tgtcattatt aagtttgatc tttaatttga gctataacat agtattgtta tttaattgat      240
tgattgatta tatgattaat tataggttcc attatttcaa aacacggatg aacatgttta      300
cgaaacaata tgcaaatatc tgaaaccagt cacatattca gagaaaagtt atatcattcg      360
aaaaggagaa ccacttgata tgattctctt catcacacaa ggtgttgtgt gggcatttgg      420
aaatgctact actcccataa gtcgacttca aaaaggtgat ttctatggaa atgaactcat      480
agaatggcaa ttaaagtcaa catccattga tgagtttcct atttcggttg ctaatcttaa      540
atcccayacc aatgttgaag ctcttgctct tatggccaat gacttggaac atgtagtctc      600
caattgctgg ttcaagttct cccccacctg ctcatctatg cctga                     645

<210> SEQ ID NO 34
<211> LENGTH: 645
<212> TYPE: DNA
<213> ORGANISM: Humulus lupulus

<400> SEQUENCE: 34
cattcctcag gatctaaagc gaattattaa gaaatacatt caaatgagat tgcaagatgg      60
aaaagatgtg gacatcgacc atattttgca tattcttcct ttgtcacagg gaatgctaat      120
taagaaacac atgtgtttcc ctatgttaaa aaaagtaagt tatcttttat agtatatrta      180
tgtcattatt aagtttgatc tttaatttga gctataacat agtattgtta tttaattgat      240
tgattgatta tatgattaat tataggttcc attatttcaa aacacggatg aacatgttta      300
cgaaacaata tgcaaatatc tgaaaccagt cacatattca gagaaaagtt atatcattcg      360
aaaaggagar ccacttgata tgattctctt catcacacaa ggtgttgtgt gggcatttgg      420
aaatgmtact actcccataa gtcgacttca aaaaggtgat ttctatggaa atgaactcat      480
agaatggcaa ttaaagtcaa catccattga tgagtttcct atttcggttg ctaatcttaa      540
atcccatacc aatgttgaag cycttgctct tatggccaat gacttggaac atgtagtctc      600
caattgctgg ttcaagttct cccscacctg ctcatctatg cctga                     645

<210> SEQ ID NO 35
```

-continued

```
<211> LENGTH: 645
<212> TYPE: DNA
<213> ORGANISM: Humulus lupulus

<400> SEQUENCE: 35
cattcctcag gatctaaagc gaattattaa gaaatacatt caaatgagat tgcaagatgg      60
aaaagatgtg gacatcgacc atattttgca tattcttcct ttgtcacagg gaatgctaat     120
taagaaacac atgtgtttcc ctatgttaaa aaagtaagt tatcttttat agtatatrta      180
tgtcattatt aagtttgatc tttaatttga gctataacat agtattgtta tttaattgat     240
tgattgatta tatgattaat tataggttcc attatttcaa aacacggatg aacatgttta     300
cgaaacaata tgcaaatatc tgaaaccagt cacatattca gagaaaagtt atatcattcg     360
aaaaggagar ccacttgata tgattctctt catcacacaa ggtgttgtgt gggcatttgg     420
aaatgmtact actcccatra gtcgacttca aaaaggtgat ttctatggaa atgaactcat     480
agaatggcaa ttaaagtcaa catccattga tgagtttcct atttcggttg ctaatcttaa     540
atcccatacc aatgttgaag cycttgctct tatggccaat gacttggaac atgtagtctc     600
caattgctgg ttcaagttct cccscacctg ctcatctatg cctga                    645

<210> SEQ ID NO 36
<211> LENGTH: 645
<212> TYPE: DNA
<213> ORGANISM: Humulus lupulus

<400> SEQUENCE: 36
cattcctcag gatctaaagc gaattattaa gaaatacatt caaatgagat tgcaagatgg      60
aaaagatgtg gacatcgacc atattttgca tattcttcct ttgtcacagg gaatgctaat     120
taagaaacac atgtgtttcc ctatgttaaa aaagtaagt tatcttttat agtatatata      180
tgtcattatt aagtttgatc tttaatttga gctataacat agtattgtta tttaattgat     240
tgattgatta tatgattaat tataggttcc attatttcaa aacacggatg aacatgttta     300
cgaaacaata tgcaaatatc tgaaaccagt cacatattca gagaaaagtt atatcattcg     360
aaaaggagaa ccacttgata tgattctctt catcacacaa ggtgttgtgt gggcatttgg     420
aaatgctact actcccataa gtcgacttca aaaaggtgat ttctatggaa atgaactcat     480
agaatggcaa ttaaagtcaa catccattga tgagtttcct atttcggttg ctaatcttaa     540
atcccayacc aatgttgaag ctcttgctct tatggccaat gacttggaac atgtagtctc     600
caattgctgg ttcaagttct cccccacctg ctcatctatg cctga                    645

<210> SEQ ID NO 37
<211> LENGTH: 645
<212> TYPE: DNA
<213> ORGANISM: Humulus lupulus

<400> SEQUENCE: 37
cattcctcag gatctaaagc gaattattaa gaaatacatt caaatgagat tgcaagatgg      60
aaaagatgtg gacatcgacc atattttgca tattcttcct ttgtcacagg gaatgctaat     120
taagaaacac atgtgtttcc ctatgttaaa aaagtaagt tatcttttat agtatatrta      180
tgtcattatt aagtttgatc tttmatttga gctataacat agtattrtta tttrattgat     240
tgattgatta tatgattaat tataggttcc attatttcaa aacacggatg aacatgttta     300
cgaaacaata tgcaaatatc tgaaaccagt cacatattca gagaaaagtt atatcattcg     360
aaaaggagar ccacttgata tgattctctt catcacacaa ggtgttgtgt gggcatttgg     420
```

```
aaatgmtact actcccataa gtcgacttca aaaaggtgat ttctatggaa atgaactcat    480
agaatggcaa ttaaagtcaa catccattga tgagtttcct atttcggttg ctaatcttaa    540
atcccatacc aatgttgaag cycttgctct tatggccaat gacttggaac atgtagtctc    600
caattgctgg ttcaagttct cccycacctg ctcatctatg cctga                   645

<210> SEQ ID NO 38
<211> LENGTH: 645
<212> TYPE: DNA
<213> ORGANISM: Humulus lupulus

<400> SEQUENCE: 38
cattcctcag gatctaaagc gaattattaa gaaatacatt caaatgagat tgcaagatgg    60
aaaagatgtg gacatcgacc atattttgca tattcttcct ttgtcacagg gaatgctaat    120
taagaaacac atgtgtttcc ctatgttaaa aaaagtaagt tatcttttat agtatatata    180
tgtcattatt aagtttgatc tttaatttga gctataacat agtattgtta tttaattgat    240
tgattgatta tatgattaat tataggttcc attatttcaa aacacggatg aacatgttta    300
cgaaacaata tgcaaatatc tgaaaccagt cacatattca gagaaaagtt atatcattcg    360
aaaaggagaa ccacttgata tgattctctt catcacacaa ggtgttgtgt gggcatttgg    420
aaatgctact actcccataa gtcgacttca aaaaggtgat ttctatggaa atgaactcat    480
agaatggcaa ttaaagtcaa catccattga tgagtttcct atttcggttg ctaatcttaa    540
atcccatacc aatgttgaag ctcttgctct tatggccaat gacttggaac atgtagtctc    600
caattgctgg ttcaagttct cccccacctg ctcatctatg cctga                   645

<210> SEQ ID NO 39
<211> LENGTH: 645
<212> TYPE: DNA
<213> ORGANISM: Humulus lupulus

<400> SEQUENCE: 39
cattcctcag gatctaaagc gaattattaa gaaatacatt caaatgagat tgcaagatgg    60
aaaagatgtg gacatcgacc atattttgca tattcttcct ttgtcacagg gaatgctaat    120
taagaaacac atgtgtttcc ctatgttaaa aaaagtaagt tatcttttat agtatatata    180
tgtcattatt aagtttgatc tttaatttga gctataacat agtattgtta tttaattgat    240
tgattgatta tatgattaat tataggttcc attatttcaa aacacggatg aacatgttta    300
cgaaacaata tgcaaatatc tgaaaccagt cacatattca gagaaaagtt atatcattcg    360
aaaaggagaa ccacttgata tgattctctt catcacacaa ggtgttgtgt gggcatttgg    420
aaatgctact actcccataa gtcgacttca aaaaggtgat ttctatggaa atgaactcat    480
agaatggcaa ttaaagtcaa catccattga tgagtttcct atttcggttg ctaatcttaa    540
atcccayacc aatgttgaag ctcttgctct tatggccaat gacttggaac atgtagtctc    600
caattgctgg ttcaagttct cccccacctg ctcatctatg cctga                   645

<210> SEQ ID NO 40
<211> LENGTH: 645
<212> TYPE: DNA
<213> ORGANISM: Humulus lupulus

<400> SEQUENCE: 40
cattcctcag gatctaaagc gaattattaa gaaatacatt caaatgagat tgcaagatgg    60
```

```
aaaagatgtg gacatcgacc atattttgca tattcttcct ttgtcacagg gaatgctaat    120
taagaaacac atgtgtttcc ctatgttaaa aaaagtaagt tatcttttat agtatatata    180
tgtcattatt aagtttgatc tttaatttga gctataacat agtattgtta tttaattgat    240
tgattgatta tatgattaat tataggttcc attatttcaa aacacggatg aacatgttta    300
cgaaacaata tgcaaatatc tgaaaccagt cacatattca gagaaaagtt atatcattcg    360
aaaaggagaa ccacttgata tgattctctt catcacacaa ggtgttgtgt gggcatttgg    420
aaatgctact actcccataa gtcgacttca aaaggtgat ttctatggaa atgaactcat     480
agaatggcaa ttaaagtcaa catccattga tgagtttcct atttcggttg ctaatcttaa    540
atcccayacc aatgttgaag ctcttgctct tatggccaat gacttggaac atgtagtctc    600
caattgctgg ttcaagttct cccccacctg ctcatctatg cctga                   645
```

<210> SEQ ID NO 41
<211> LENGTH: 645
<212> TYPE: DNA
<213> ORGANISM: Humulus lupulus

<400> SEQUENCE: 41

```
cattcctcag gatctaaagc gaattattaa gaaatacatt caaatgagat tgcaagatgg     60
aaaagatgtg gacatcgacc atattttgca tattcttcct ttgtcacagg gaatgctaat    120
taagaaacac atgtgtttcc ctatgttaaa aaaagtaagt tatcttttat agtatatata    180
tgtcattatt aagtttgatc tttaatttga gctataacat agtattgtta tttaattgat    240
tgattgatta tatgattaat tataggttcc attatttcaa aacacggatg aacatgttta    300
cgaaacaata tgcaaatatc tgaaaccagt cacatattca gagaaaagtt atatcattcg    360
aaaaggagaa ccacttgata tgattctctt catcacacaa ggtgttgtgt gggcatttgg    420
aaatgctact actcccataa gtcgacttca aaaggtgat ttctatggaa atgaactcat     480
agaatggcaa ttaaagtcaa catccattga tgagtttcct atttcggttg ctaatcttaa    540
atcccayacc aatgttgaag ctcttgctct tatggccaat gacttggaac atgtagtctc    600
caattgctgg ttcaagttct cccccacctg ctcatctatg cctga                   645
```

<210> SEQ ID NO 42
<211> LENGTH: 645
<212> TYPE: DNA
<213> ORGANISM: Humulus lupulus

<400> SEQUENCE: 42

```
cattcctcag gatctaaagc gaattattaa gaaatacatt caaatgagat tgcaagatgg     60
aaaagatgtg gacatcgacc atattttgca tattcttcct ttgtcacagg gaatgctaat    120
taagaaacac atgtgtttcc ctatgttaaa aaaagtaagt tatcttttat agtatatata    180
tgtcattatt aagtttgatc tttaatttga gctataacat agtattgtta tttaattgat    240
tgattgatta tatgattaat tataggttcc attatttcaa aacacggatg aacatgttta    300
cgaaacaata tgcaaatatc tgaaaccagt cacatattca gagaaaagtt atatcattcg    360
aaaaggagaa ccacttgata tgattctctt catcacacaa ggtgttgtgt gggcatttgg    420
aaatgctact actcccataa gtcgacttca aaaggtgat ttctatggaa atgaactcat     480
agaatggcaa ttaaagtcaa catccattga tgagtttcct atttcggttg ctaatcttaa    540
atcccatacc aatgttgaag ctcttgctct tatggccaat gacttggaac atgtagtctc    600
caattgctgg ttcaagttct cccccacctg ctcatctatg cctga                   645
```

<210> SEQ ID NO 43
<211> LENGTH: 645
<212> TYPE: DNA
<213> ORGANISM: Humulus lupulus

<400> SEQUENCE: 43

| | | | | | |
|---|---|---|---|---|---|
| cattcctcag | gatctaaagc | gaattattaa | gaaatacatt | caaatgagat tgcaagatgg | 60 |
| aaaagatgtg | gacatcgacc | atattttgca | tattcttcct | ttgtcacagg gaatgctaat | 120 |
| taagaaacac | atgtgtttcc | ctatgttaaa | aaaagtaagt | tatcttttat agtatatata | 180 |
| tgtcattatt | aagtttgatc | tttaatttga | gctataacat | agtattgtta tttaattgat | 240 |
| tgattgatta | tatgattaat | tataggttcc | attatttcaa | aacacggatg aacatgttta | 300 |
| cgaaacaata | tgcaaatatc | tgaaaccagt | cacatattca | gagaaaagtt atatcattcg | 360 |
| aaaaggagaa | ccacttgata | tgattctctt | catcacacaa | ggtgttgtgt gggcatttgg | 420 |
| aaatgctact | actcccataa | gtcgacttca | aaaaggtgat | ttctatggaa atgaactcat | 480 |
| agaatggcaa | ttaaagtcaa | catccattga | tgagtttcct | atttcggttg ctaatcttaa | 540 |
| atcccayacc | aatgttgaag | ctcttgctct | tatggccaat | gacttggaac atgtagtctc | 600 |
| caattgctgg | ttcaagttct | cccccacctg | ctcatctatg | cctga | 645 |

<210> SEQ ID NO 44
<211> LENGTH: 559
<212> TYPE: DNA
<213> ORGANISM: Humulus lupulus
<220> FEATURE:
<221> NAME/KEY: misc_feature
<222> LOCATION: (129)..(134)
<223> OTHER INFORMATION: n is no nucleobase (deletion)

<400> SEQUENCE: 44

| | | | | | |
|---|---|---|---|---|---|
| tttgacgtga | tccagtggag | tggtggtata | tacgttccat | attataaaga ttacattgtt | 60 |
| ttaatggata | taccagggaa | ggagaaagta | aaactctcca | tcgcactgca agccaacccc | 120 |
| gatgatacnn | nnnntttgta | cactgatgcc | atcttgaatg | gcatcgaaat cttcaaatta | 180 |
| agcgactcca | acggaaatct | cgccggtctg | aatcttgacc | ttgttccgca tgcgaagcca | 240 |
| ccaagccaac | cattatggaa | gttgaaaaat | catcaatcag | agattattgg catttccatt | 300 |
| ggtgtagttt | gcagcgttgt | tttgctctgc | ataattggat | tcctatttct ccggcgaggt | 360 |
| agaaaagtca | aaggcacaag | gctcatttcc | ttgtctacaa | ccaggtcaag caagaccgga | 420 |
| aaatcatcat | tgccgttgga | tcggtgtcgt | tactttcat | tggctgagat cattactgca | 480 |
| acaaacaact | tcgaagatat | tttcattatt | ggggttggag | gattcggaaa cgtgtataaa | 540 |
| gggcacatcg | acaatggga | | | | 559 |

<210> SEQ ID NO 45
<211> LENGTH: 559
<212> TYPE: DNA
<213> ORGANISM: Humulus lupulus
<220> FEATURE:
<221> NAME/KEY: misc_feature
<222> LOCATION: (129)..(134)
<223> OTHER INFORMATION: n is no nucleobase (deletion)

<400> SEQUENCE: 45

| | | | | | |
|---|---|---|---|---|---|
| tttgacgtga | tccagtggag | tggtggtata | tacgttccat | attataaaga ttacattgtt | 60 |
| ttaatggata | taccagggaa | ggagaaagta | aaactctcca | tcgcactgca agccaacccc | 120 |

```
gatgatacnn nnnntttgta cactgatgcc atcttgaatg gcatcgaaat cttcaaatta    180
agcgactcca acggaaatct cgccggtctg aatcttgacc ttgttccgca tgcgaagcca    240
ccaagccaac cattatggaa gttgaaaaat catcaatcag agattattgg catttccatt    300
ggtgtagttt gcagcgttgt tttgctctgc ataattggat tcctatttct ccggcgaggt    360
agaaaagtca aaggcacaag gctcatttcc ttgtctacaa ccaggtcaag caagaccgga    420
aaatcatcat tgccgttgga tcggtgtcgt tactttttcat tggctgagat cattactgca    480
acaaacaact tcgaagatat tttcattatt ggggttggag gattcggaaa cgtgtataaa    540
gggcacatcg acaatggga                                                 559
```

<210> SEQ ID NO 46
<211> LENGTH: 559
<212> TYPE: DNA
<213> ORGANISM: Humulus lupulus
<220> FEATURE:
<221> NAME/KEY: misc_feature
<222> LOCATION: (129)..(134)
<223> OTHER INFORMATION: n is no nucleobase (deletion)

<400> SEQUENCE: 46

```
tttgacgtga tccagtggag tggtggtata tacgttccat attataaaga ttacattgtt     60
ttaatggata taccagggaa ggagaaagta aaactctcca tcgcactgca agccaacccc    120
gatgatacnn nnnntttgta cactgatgcc atcttgaatg gcatcgaaat cttcaaatta    180
agcgactcca acggaaatct cgccggtctg aatcttgacc ttgttccgca tgcgaagcca    240
ccaagccaac cattatggaa gttgaaaaat catcaatcag agattattgg catttccatt    300
ggtgtagttt gcagcgttgt tttgctctgc ataattggat tcctatttct ccggcgaggt    360
agaaaagtca aaggcacaag gctcatttcc ttgtctacaa ccaggtcaag caagaccgga    420
aaatcatcat tgccgttgga tcggtgtcgt tactttttcat tggctgagat cattactgca    480
acaaacaact tcgaagatat tttcattatt ggggttggag gattcggaaa cgtgtataaa    540
gggcacatcg acaatggga                                                 559
```

<210> SEQ ID NO 47
<211> LENGTH: 559
<212> TYPE: DNA
<213> ORGANISM: Humulus lupulus
<400> SEQUENCE: 47

```
ttcgacgtga tcgagttgag tggtggtata tacgttccat attataaaga ttacattgtt     60
ttaatggata taccagggaa ggagaattta aaactctcca tcgcactgca agccaacccc    120
gatgatacca tgactttgta cactgatgcc atcttgaatg gcatcgaaat cttcaaatta    180
agcgactcca acggaaatct cgccggtctg aatcttgacc ttgttccgca tgcgaagcca    240
ccaagccaac catcatggaa gttgaaaaat catcaatcag agattattgg catttccatt    300
ggtgtagttt gcagcgttgt tttgctctgc ataattggat tcctatttct ccggcgaggt    360
agaaaagtca aaggaacaat gctcatttcc ttgtcaacta ccaggtcaag caagaccgga    420
gaatcatcat tgccgttgga tcggtgtcgt tactttttcac tggctgagat cattactgca    480
gcaaacaact tcgaagatat tttcattatt ggggttggag gattcggaaa cgtgtataaa    540
gggcacatcg acaatggga                                                 559
```

<210> SEQ ID NO 48
<211> LENGTH: 559

```
<212> TYPE: DNA
<213> ORGANISM: Humulus lupulus
<220> FEATURE:
<221> NAME/KEY: misc_feature
<222> LOCATION: (129)..(134)
<223> OTHER INFORMATION: n is no nucleobase (deletion)

<400> SEQUENCE: 48
tttgacgtga tccagtggag tggtggtata tacgttccat attataaaga ttacattgtt      60
ttaatggata taccagggaa ggagaaagta aaactctcca tcgcactgca agccaacccc     120
gatgatacnn nnnntttgta cactgatgcc atcttgaatg gcatcgaaat cttcaaatta     180
agcgactcca acggaaatct cgccggtctg aatcttgacc ttgttccgca tgcgaagcca     240
ccaagccaac cattatggaa gttgaaaaat catcaatcag agattattgg catttccatt     300
ggtgtagttt gcagcgttgt tttgctctgc ataattggat tcctatttct ccggcgaggt     360
agaaaagtca aaggcacaag gctcatttcc ttgtctacaa ccaggtcaag caagaccgga     420
aaatcatcat tgccgttgga tcggtgtcgt tactttcat tggctgagat cattactgca      480
acaaacaact tcgaagatat tttcattatt ggggttggag gattcggaaa cgtgtataaa     540
gggcacatcg acaatggga                                                   559

<210> SEQ ID NO 49
<211> LENGTH: 559
<212> TYPE: DNA
<213> ORGANISM: Humulus lupulus

<400> SEQUENCE: 49
ttcgacgtga tcgagttgag tggtggtata tacgttccat attataaaga ttacattgtt      60
ttaatggata taccagggaa ggagaattta aaactctcca tcgcactgca agccaacccc     120
gatgatacca tgactttgta cactgatgcc atcttgaatg gcatcgaaat cttcaaatta     180
agcgactcca acggaaatct cgccggtctg aatcttgacc ttgttccgca tgcgaagcca     240
ccaagccaac catcatggaa gttgaaaaat catcaatcag agattattgg catttccatt     300
ggtgtagttt gcagcgttgt tttgctctgc ataattggat tcctatttct ccggcgaggt     360
agaaaagtca aaggaacaat gctcatttcc ttgtcaacta ccaggtcaag caagaccgga     420
gaatcatcat tgccgttgga tcggtgtcgt tactttcac tggctgagat cattactgca      480
gcaaacaact tcgaagatat tttcattatt ggggttggag gattcggaaa cgtgtataaa     540
gggcacatcg acaatggga                                                   559

<210> SEQ ID NO 50
<211> LENGTH: 559
<212> TYPE: DNA
<213> ORGANISM: Humulus lupulus
<220> FEATURE:
<221> NAME/KEY: misc_feature
<222> LOCATION: (129)..(134)
<223> OTHER INFORMATION: n is no nucleobase (deletion)

<400> SEQUENCE: 50
tttgacgtga tccagtggag tggtggtata tacgttccat attataaaga ttacattgtt      60
ttaatggata taccagggaa ggagaaagta aaactctcca tcgcactgca agccaacccc     120
gatgatacnn nnnntttgta cactgatgcc atcttgaatg gcatcgaaat cttcaaatta     180
agcgactcca acggaaatct cgccggtctg aatcttgacc ttgttccgca tgcgaagcca     240
ccaagccaac cattatggaa gttgaaaaat catcaatcag agattattgg catttccatt     300
```

```
ggtgtagttt gcagcgttgt tttgctctgc ataattggat tcctatttct ccggcgaggt   360
agaaaagtca aaggcacaag gctcatttcc ttgtctacaa ccaggtcaag caagaccgga   420
aaatcatcat tgccgttgga tcggtgtcgt tacttttcat tggctgagat cattactgca   480
acaaacaact tcgaagatat tttcattatt ggggttggag gattcggaaa cgtgtataaa   540
gggcacatcg acaatggga                                                559

<210> SEQ ID NO 51
<211> LENGTH: 559
<212> TYPE: DNA
<213> ORGANISM: Humulus lupulus
<220> FEATURE:
<221> NAME/KEY: misc_feature
<222> LOCATION: (129)..(134)
<223> OTHER INFORMATION: n is no nucleobase (deletion)

<400> SEQUENCE: 51
tttgacgtga tccagtggag tggtggtata tacgttccat attataaaga ttacattgtt    60
ttaatggata taccagggaa ggagaaagta aaactctcca tcgcactgca agccaacccc   120
gatgatacnn nnnntttgta cactgatgcc atcttgaatg gcatcgaaat cttcaaatta   180
agcgactcca acggaaatct cgccggtctg aatcttgacc ttgttccgca tgcgaagcca   240
ccaagccaac cattatggaa gttgaaaaat catcaatcag agattattgg catttccatt   300
ggtgtagttt gcagcgttgt tttgctctgc ataattggat tcctatttct ccggcgaggt   360
agaaaagtca aaggcacaag gctcatttcc ttgtctacaa ccaggtcaag caagaccgga   420
aaatcatcat tgccgttgga tcggtgtcgt tacttttcat tggctgagat cattactgca   480
acaaacaact tcgaagatat tttcattatt ggggttggag gattcggaaa cgtgtataaa   540
gggcacatcg acaatggga                                                559

<210> SEQ ID NO 52
<211> LENGTH: 559
<212> TYPE: DNA
<213> ORGANISM: Humulus lupulus
<220> FEATURE:
<221> NAME/KEY: misc_feature
<222> LOCATION: (129)..(134)
<223> OTHER INFORMATION: n is no nucleobase (deletion)

<400> SEQUENCE: 52
tttgacgtga tccagtggag tggtggtata tacgttccat attataaaga ttacattgtt    60
ttaatggata taccagggaa ggagaaagta aaactctcca tcgcactgca agccaacccc   120
gatgatacnn nnnntttgta cactgatgcc atcttgaatg gcatcgaaat cttcaaatta   180
agcgactcca acggaaatct cgccggtctg aatcttgacc ttgttccgca tgcgaagcca   240
ccaagccaac cattatggaa gttgaaaaat catcaatcag agattattgg catttccatt   300
ggtgtagttt gcagcgttgt tttgctctgc ataattggat tcctatttct ccggcgaggt   360
agaaaagtca aaggcacaag gctcatttcc ttgtctacaa ccaggtcaag caagaccgga   420
aaatcatcat tgccgttgga tcggtgtcgt tacttttcat tggctgagat cattactgca   480
acaaacaact tcgaagatat tttcattatt ggggttggag gattcggaaa cgtgtataaa   540
gggcacatcg acaatggga                                                559

<210> SEQ ID NO 53
<211> LENGTH: 559
<212> TYPE: DNA
<213> ORGANISM: Humulus lupulus
```

<220> FEATURE:
<221> NAME/KEY: misc_feature
<222> LOCATION: (129)..(134)
<223> OTHER INFORMATION: n is no nucleobase (deletion)

<400> SEQUENCE: 53

| | |
|---|---|
| tttgacgtga tccagtggag tggtggtata tacgttccat attataaaga ttacattgtt | 60 |
| ttaatggata taccagggaa ggagaaagta aaactctcca tcgcactgca agccaacccc | 120 |
| gatgatacnn nnnntttgta cactgatgcc atcttgaatg gcatcgaaat cttcaaatta | 180 |
| agcgactcca acggaaatct cgccggtctg aatcttgacc ttgttccgca tgcgaagcca | 240 |
| ccaagccaac cattatggaa gttgaaaaat catcaatcag agattattgg catttccatt | 300 |
| ggtgtagttt gcagcgttgt tttgctctgc ataattggat tcctatttct ccggcgaggt | 360 |
| agaaaagtca aaggcacaag gctcatttcc ttgtctacaa ccaggtcaag caagaccgga | 420 |
| aaatcatcat tgccgttgga tcggtgtcgt tacttttcat tggctgagat cattactgca | 480 |
| acaaacaact tcgaagatat tttcattatt ggggttggag gattcggaaa cgtgtataaa | 540 |
| gggcacatcg acaatggga | 559 |

<210> SEQ ID NO 54
<211> LENGTH: 559
<212> TYPE: DNA
<213> ORGANISM: Humulus lupulus
<220> FEATURE:
<221> NAME/KEY: misc_feature
<222> LOCATION: (129)..(134)
<223> OTHER INFORMATION: n is no nucleobase (deletion)

<400> SEQUENCE: 54

| | |
|---|---|
| tttgacgtga tccagtggag tggtggtata tacgttccat attataaaga ttacattgtt | 60 |
| ttaatggata taccagggaa ggagaaagta aaactctcca tcgcactgca agccaacccc | 120 |
| gatgatacnn nnnntttgta cactgatgcc atcttgaatg gcatcgaaat cttcaaatta | 180 |
| agcgactcca acggaaatct cgccggtctg aatcttgacc ttgttccgca tgcgaagcca | 240 |
| ccaagccaac cattatggaa gttgaaaaat catcaatcag agattattgg catttccatt | 300 |
| ggtgtagttt gcagcgttgt tttgctctgc rtaattggat tcctatttct ccggcraggt | 360 |
| agaaaagtca aaggcacaag gctcatttcc ttgtcyasaa ccaggtcaag caagaccgga | 420 |
| raatcatcat tgccgttgga tcggtgtcgt tacttttcat tggctgagat catwrmygcm | 480 |
| acaaacaact tcgaagatak tttcattatt ggggttggag gattcggaaa cgtgtataaa | 540 |
| gggcacrtcg acaatggga | 559 |

<210> SEQ ID NO 55
<211> LENGTH: 559
<212> TYPE: DNA
<213> ORGANISM: Humulus lupulus

<400> SEQUENCE: 55

| | |
|---|---|
| ttcgacgtga tcgagttgag tggtggtata tacgttccat attataaaga ttacattgtt | 60 |
| ttaatggata taccagggaa ggagaattta aaactctcca tcgcactgca agccaacccc | 120 |
| gatgatacca tgactttgta cactgatgcc atcttgaatg gcatcgaaat cttcaaatta | 180 |
| agcgactcca acggaaatct cgccggtctg aatcttgacc ttgttccgca tgcgaagcca | 240 |
| ccaagccaac catcatggaa gttgaaaaat catcaatcag agattattgg catttccatt | 300 |
| ggtgtagttt gcagcgttgt tttgctctgc ataattggat tcctatttct ccggcgaggt | 360 |

```
agaaaagtca aaggaacaat gctcatttcc ttgtcaacta ccaggtcaag caagaccgga    420
gaatcatcat tgccgttgga tcggtgtcgt tacttttcac tggctgagat cattactgca    480
gcaaacaact tcgaagatat tttcattatt ggggttggag gattcggaaa cgtgtataaa    540
gggcacatcg acaatggga                                                 559
```

<210> SEQ ID NO 56
<211> LENGTH: 559
<212> TYPE: DNA
<213> ORGANISM: Humulus lupulus
<220> FEATURE:
<221> NAME/KEY: misc_feature
<222> LOCATION: (129)..(134)
<223> OTHER INFORMATION: n is no nucleobase (deletion)

<400> SEQUENCE: 56

```
tttgacgtga tccagtggag tggtggtata tacgttccat attataaaga ttacattgtt     60
ttaatggata taccagggaa ggagaaagta aaactctcca tcgcactgca agccaacccc    120
gatgatacnn nnnntttgta cactgatgcc atcttgaatg gcatcgaaat cttcaaatta    180
agcgactcca acggaaatct cgccggtctg aatcttgacc ttgttccgca tgcgaagcca    240
ccaagccaac cattatggaa gttgaaaaat catcaatcag agattattgg catttccatt    300
ggtgtagttt gcagcgttgt tttgctctgc ataattggat tcctatttct ccggcgaggt    360
agaaaagtca aaggcacaag gctcatttcc ttgtctacaa ccaggtcaag caagaccgga    420
aaatcatcat tgccgttgga tcggtgtcgt tacttttcat tggctgagat cattactgca    480
acaaacaact tcgaagatat tttcattatt ggggttggag gattcggaaa cgtgtataaa    540
gggcacatcg acaatggga                                                 559
```

<210> SEQ ID NO 57
<211> LENGTH: 559
<212> TYPE: DNA
<213> ORGANISM: Humulus lupulus
<220> FEATURE:
<221> NAME/KEY: misc_feature
<222> LOCATION: (129)..(134)
<223> OTHER INFORMATION: n is no nucleobase (deletion)

<400> SEQUENCE: 57

```
tttgacgtga tccagtggag tggtggtata tacgttccat attataaaga ttacattgtt     60
ttaatggata taccagggaa ggagaaagta aaactctcca tcgcactgca agccaacccc    120
gatgatacnn nnnntttgta cactgatgcc atcttgaatg gcatcgaaat cttcaaatta    180
agcgactcca acggaaatct cgccggtctg aatcttgacc ttgttccgca tgcgaagcca    240
ccaagccaac cattatggaa gttgaaaaat catcaatcag agattattgg catttccatt    300
ggtgtagttt gcagcgttgt tttgctctgc ataattggat tcctatttct ccggcgaggt    360
agaaaagtca aaggcacaag gctcatttcc ttgtctacaa ccaggtcaag caagaccgga    420
aaatcatcat tgccgttgga tcggtgtcgt tacttttcat tggctgagat cattactgca    480
acaaacaact tcgaagatat tttcattatt ggggttggag gattcggaaa cgtgtataaa    540
gggcacatcg acaatggga                                                 559
```

<210> SEQ ID NO 58
<211> LENGTH: 538
<212> TYPE: DNA
<213> ORGANISM: Humulus lupulus
<220> FEATURE:
<221> NAME/KEY: misc_feature

```
<222> LOCATION: (186)..(194)
<223> OTHER INFORMATION: n is no nucleobase (deletion)
<220> FEATURE:
<221> NAME/KEY: misc_feature
<222> LOCATION: (399)..(399)
<223> OTHER INFORMATION: n is no nucleobase (deletion)

<400> SEQUENCE: 58
cagctgagct tgaaagttat ggctatcgcc gccaccattt cgggtcctct gacaactccg      60
tctcggcggc gctcagtcac ctccttcagc tcactctcca tttctcattc tcttacggga     120
caattgagtt ttctcagagc aagtcgcccc tgtattggct tgttagctac tgcttcttct     180
tcttcnnnnn nnnncatttc catgagtctc gaagccgccg agaaggcctc gccggtgtcg     240
ttcttggatc gcagggagac cggttttctt cattttgtca agtaccacgg cgtcggcaat     300
gacttcatct tggtaaactc gaaaatggag ctagttttttc tctatagagg aaaagaaaga     360
atttttttct tctaaattta ttgagtagtc tcttttttgna ttgatgtagg ttgataatag     420
ggattcttca gagcctagga ttactcccga gcaagcggtg aagctctgtg atcggaactt     480
tggaattgga gctgatgggg tgattttttgc tatgcctggc atcaatggca ctgactac      538

<210> SEQ ID NO 59
<211> LENGTH: 538
<212> TYPE: DNA
<213> ORGANISM: Humulus lupulus

<400> SEQUENCE: 59
cagctgagct tgaaagttat ggctatcgcc gccgccattt cgggtcctct gacaactccg      60
tctcggcggc gctcagtcac ctccttcagc tcactctcca attctcattc tcttacgaga     120
caactgagtt ttctcagagc aagtcgcccc tgtattggct tgtcagccac agcttcttct     180
tcttcttctt cttccatttc catgagtctc gaagccgccg agaaggcctc gccggtgtcg     240
ttcttggatc gcagggagac cggttttctt cattttgtca agtaccacgg cgtcggcaat     300
gacttcatct tggtaaactc gaaaatggag ctagttttttc tctatagagg aaaagaaaga     360
atttttttct tctaaattta ttgagtagtc ttttttttta ttgatgtagg ttgataatag     420
ggattcttca gagcctagga ttactcccga gcaagcggcg aagctctgtg atcggaactt     480
tggaattgga gctgatgggg tcattttttgc tatgcctggc atcaatggca ctgactac      538

<210> SEQ ID NO 60
<211> LENGTH: 516
<212> TYPE: DNA
<213> ORGANISM: Humulus lupulus

<400> SEQUENCE: 60
agtacgatgc tttgcccgat ttattgtcga gcttgagaat tgcaaggaaa gcacaggtaa      60
catatcatac atacacatgc acatatatat atatatacat ataatgtaaa tgttgattct     120
ctattgtgat gatttgcttc tgaaacatga taaaagaaac aataaaaaga acaaagaagt     180
attggttatt gggaagacct ctttcggatt tctttgacaa tgcctgtatg ttttattgat     240
gtagctttac tgtacatact ggtgctggtc taattattcc agaaatacta gatgatggtc     300
aggtataaac ttctctactt gcaaattacc taaatctatt gggttcatat gcttcaaaag     360
caacattcat aaatgattgc attttgctac aattatggca gttttgcttc taatctggat     420
ttgttgaagt tgccaaacta ctggatacg atttttgagt attcaattta gcagggtgc     480 tgttttgatt tcaggtcaaa gttgatatgg gtgaaa                               516
```

<210> SEQ ID NO 61
<211> LENGTH: 516
<212> TYPE: DNA
<213> ORGANISM: Humulus lupulus
<220> FEATURE:
<221> NAME/KEY: misc_feature
<222> LOCATION: (57)..(59)
<223> OTHER INFORMATION: n is no nucleotide (deletion)
<220> FEATURE:
<221> NAME/KEY: misc_feature
<222> LOCATION: (65)..(65)
<223> OTHER INFORMATION: n is no nucleotide (deletion)

<400> SEQUENCE: 61

```
gcaaggaaag cccaggtgac atatctatat acctatacat gcgtatatat acacacnnna      60
cacancacac acacacacac acacacacac acatatacat ataatgtaaa tgttgatact     120
ctattgtgat gatttgcttc tgaaacatga tattagaaac aataaaaaga acaagaagt      180 attggttatt aggaagacct cttttagatt tctttgacaa tgcctatgtg ttctattgat     240
gtagctttac tgtgcatact ggtgctggtc taattattcc agaaatacaa gatgatggtc     300
aggtataaac ttctatactt gcaaattacc taaatctatt gggttcatag gcttcaaaag     360
caacattcat aaatgattgc attttgctac agttatggca gtttggcttc taatctggat     420
ttgttgaagt tgccaaacta ctggatagcg attttttgagt attcaattta gcaggggtgc    480
tgttttgatt tcaggtcaaa gttgatatgg gtgaaa                               516
```

<210> SEQ ID NO 62
<211> LENGTH: 535
<212> TYPE: DNA
<213> ORGANISM: Humulus lupulus
<220> FEATURE:
<221> NAME/KEY: misc_feature
<222> LOCATION: (12)..(12)
<223> OTHER INFORMATION: n is no nucleobase (deletion)
<220> FEATURE:
<221> NAME/KEY: misc_feature
<222> LOCATION: (183)..(191)
<223> OTHER INFORMATION: n is no nucleobase (deletion)
<220> FEATURE:
<221> NAME/KEY: misc_feature
<222> LOCATION: (396)..(396)
<223> OTHER INFORMATION: n is no nucleobase (deletion)

<400> SEQUENCE: 62

```
ctgagcttga angttatggc tatcgccgcc accatttcgg gtcctctgac aactccgtct      60
cggcggcgct cagtcacctc cttcagctca ctctccattt ctcattctct tacgggacaa     120
ttgagttttc tcagagcaag tcgcccctgt attggcttgt tagctactgc ttcttcttct     180
tcnnnnnnnn ncatttccat gagtctcgaa gccgccgaga aggcctcgcc ggtgtcgttc     240
ttggatcgca gggagaccgg ttttcttcat tttgtcaagt accacggcgt cggcaatgac     300
ttcatcttgg taaactcgaa aatggagcta gttttttctct atagaggaaa agaaagaatt    360 ttttcttct aaatttattg agtagtctct ttttgnattg atgtaggttg ataataggga      420
ttcttcagag cctaggatta ctcccgagca agcggtgaag ctctgtgatc ggaactttgg     480
aattggagct gatggggtga ttttttgctat gcctggcatc aatggcactg actac         535
```

<210> SEQ ID NO 63
<211> LENGTH: 535
<212> TYPE: DNA
<213> ORGANISM: Humulus lupulus
<220> FEATURE:
<221> NAME/KEY: misc_feature -continued

```
<222> LOCATION: (12)..(12)
<223> OTHER INFORMATION: n is no nucleobase (deletion)

<400> SEQUENCE: 63
ctgagcttga angttatggc tatcgccgcc gccatttcgg gtcctctgac aactccgtct      60
cggcggcgct cagtcacctc cttcagctca ctctccaatt ctcattctct tacgagacaa     120
ctgagttttc tcagagcaag tcgcccctgt attggcttgt cagccacagc ttcttcttct     180
tcttcttctt ccatttccat gagtctcgaa gccgccgaga aggcctcgcc ggtgtcgttc     240
ttggatcgca gggagaccgg ttttcttcat tttgtcaagt accacggcgt cggcaatgac     300
ttcatcttgg taaactcgaa aatggagcta gttttttctct atagaggaaa agaaagaatt     360
tttttcttct aaatttattg agtagtcttt tttttttattg atgtaggttg ataataggga     420
ttcttcagag cctaggatta ctcccgagca agcggcgaag ctctgtgatc ggaactttgg     480
aattggagct gatggggtca tttttgctat gcctggcatc aatggcactg actac          535

<210> SEQ ID NO 64
<211> LENGTH: 535
<212> TYPE: DNA
<213> ORGANISM: Humulus lupulus
<220> FEATURE:
<221> NAME/KEY: misc_feature
<222> LOCATION: (183)..(191)
<223> OTHER INFORMATION: n is no nucleobase (deletion)
<220> FEATURE:
<221> NAME/KEY: misc_feature
<222> LOCATION: (396)..(396)
<223> OTHER INFORMATION: n is no nucleobase (deletion)

<400> SEQUENCE: 64
ctgagcttga aagttatggc tatcgccgcc accatttcgg gtcctctgac aactccgtct      60
cggcggcgct cagtcacctc cttcagctca ctctccattt ctcattctct tacgggacaa     120
ttgagttttc tcagagcaag tcgcccctgt attggcttgt tagctactgc ttcttcttct     180
tcnnnnnnnn ncatttccat gagtctcgaa gccgccgaga aggcctcgcc ggtgtcgttc     240
ttggatcgca gggagaccgg ttttcttcat tttgtcaagt accacggcgt cggcaatgac     300
ttcatcttgg taaactcgaa aatggagcta gttttttctct atagaggaaa agaaagaatt     360
tttttcttct aaatttattg agtagtcttt ttttgnattg atgtaggttg ataataggga     420
ttcttcagag cctaggatta ctcccgagca agcggtgaag ctctgtgatc ggaactttgg     480
aattggagct gatggggtga tttttgctat gcctggcatc aatggcactg actac          535

<210> SEQ ID NO 65
<211> LENGTH: 535
<212> TYPE: DNA
<213> ORGANISM: Humulus lupulus
<220> FEATURE:
<221> NAME/KEY: misc_feature
<222> LOCATION: (12)..(12)
<223> OTHER INFORMATION: n is no nucleobase (deletion)

<400> SEQUENCE: 65
cagagcttga angttatggc tatcgccgcc gccatttcgg gtcctctgac aactccgtct      60
cggcggcgct cagtcacctc cttcagctca ctctccaatt ctcattctct tacgagacaa     120
ctgagttttc tcagagcaag tcgcccctgt attggcttgt cagccacagc ttcttcttct     180
tcttcttctt ccatttccat gagtctcgaa gccgccgaga aggcctcgcc ggtgtcgttc     240
ttggatcgca gggagaccgg ttttcttcat tttgtcaagt accacggcgt cggcaatgac     300
```

```
ttcatcttgg taaactcgaa aatggagcta gttttttctct atagaggaaa agaaagaatt    360
tttttcttct aaatttattg agtagtctttt tttttttattg atgtaggttg ataataggga    420
ttcttcagag cctaggatta ctcccgagca agcggcgaag ctctgtgatc ggaactttgg    480
aattggagct gatggggtca ttttttgctat gcctggcatc aatggcactg actac         535
```

<210> SEQ ID NO 66
<211> LENGTH: 535
<212> TYPE: DNA
<213> ORGANISM: Humulus lupulus

<400> SEQUENCE: 66

```
ctgagcttga aagttatggc tatcgccgcc gccatttcgg gtcctctgac aactccgtct      60
cggcggcgct cagtcacctc cttcagctca ctctccaatt ctcattctct tacgagacaa    120
ctgagttttc tcagagcaag tcgcccctgt attggcttgt cagccacagc ttcttcttct    180
tcttcttctt ccatttccat gagtctcgaa gccgccgaga aggcctcgcc ggtgtcgttc    240
ttggatcgca gggagaccgg ttttcttcat tttgtcaagt accacggcgt cggcaatgac    300
ttcatcttgg taaactcgaa aatggagcta gttttttctct atagaggaaa agaaagaatt    360
tttttcttct aaatttattg agtagtctttt tttttttattg atgtaggttg ataataggga    420
ttcttcagag cctaggatta ctcccgagca agcggcgaag ctctgtgatc ggaactttgg    480
aattggagct gatggggtca ttttttgctat gcctggcatc aatggcactg actac         535
```

<210> SEQ ID NO 67
<211> LENGTH: 443
<212> TYPE: DNA
<213> ORGANISM: Humulus lupulus
<220> FEATURE:
<221> NAME/KEY: misc_feature
<222> LOCATION: (437)..(437)
<223> OTHER INFORMATION: n is no nucleotide (deletion)

<400> SEQUENCE: 67

```
atacatacac atgcacatat atatatatat acatagaatg taaatgttga ttctctattg     60
tgatgatttg cttctgaaac atgataaaag aaacaataaa aagaacaaag aagtattggt    120
tattgggaag acctctttcg gatttctttg acaatgcctg tatgttttat tgatgtagct    180
ttactgtaca tactggtgct ggtctaatta ttccagaaat actagatgat ggtcaggtat    240
aaacttctct acttgcaaat tacctaaatc taatgggttc atatgcttca aaagcaacat    300
tcataaatga ttgcattttg ctacaattat ggcagttttgg cttctaatct ggatttgttg    360
aagttgccaa actactggat agcgattttt gagtattcaa tttagcaggg gtgctgtttt    420
tatttcaggt caaagtngat atg                                              443
```

<210> SEQ ID NO 68
<211> LENGTH: 443
<212> TYPE: DNA
<213> ORGANISM: Humulus lupulus
<220> FEATURE:
<221> NAME/KEY: misc_feature
<222> LOCATION: (437)..(437)
<223> OTHER INFORMATION: n is no nucleobase (deletion)

<400> SEQUENCE: 68

```
acacacacac acacacacac acacacatat acatataatg taaatgttga tactctattg     60
tgatgatttg cttctgaaac atgatattag aaacaataaa aagaacaaag aagtattggt    120
tattaggaag acctctttta gatttctttg acaatgccta tgtgttctat tgatgtagct    180
```

```
ttactgtgca tactggtgct ggtctaatta ttccagaaat acaagatgat ggtcaggtat      240
aaacttctat acttgcaaat tacctaaatc tattgggttc ataggcttca aaagcaacat      300
tcataaatga ttgcattttg ctacagttat ggcagtttgg cttctaatct ggatttgttg      360
aagttgccaa actactggat agcgattttt gagtattcaa tttagcaggg gtgctgtttt      420
gatttcaggt caaagtngat atg                                              443
```

<210> SEQ ID NO 69
<211> LENGTH: 443
<212> TYPE: DNA
<213> ORGANISM: Humulus lupulus

<400> SEQUENCE: 69

```
atacatacac atgcacatat atatatatat acatataatg taaatgttga ttctctattg       60
tgatgatttg cttctgaaac atgataaaag aaacaataaa agaacaaag aagtattggt       120 tattgggaag acctctttcg gatttctttg acaatgcctg tatgttttat tgatgtagct      180
ttactgtaca tactggtgct ggtctaatta ttccagaaat actagatgat ggtcaggtat      240
aaacttctct acttgcaaat tacctaaatc tattgggttc atatgcttca aaagcaacat      300
tcataaatga ttgcattttg ctacaattat ggcagttttg cttctaatct ggatttgttg      360
aagttgccaa actactggat agcgattttt gagtattcaa tttagcaggg gtgctgtttt      420
gatttcaggt caaagttgat atg                                              443
```

<210> SEQ ID NO 70
<211> LENGTH: 443
<212> TYPE: DNA
<213> ORGANISM: Humulus lupulus
<220> FEATURE:
<221> NAME/KEY: misc_feature
<222> LOCATION: (437)..(437)
<223> OTHER INFORMATION: n is no nucleobase (deletion)

<400> SEQUENCE: 70

```
acacacacac acacacacac acacacatat acatataatg taaatgttga tactctattg       60
tgatgatttg cttctgaaac atgatattag aaacaataaa agaacaaag aagtattggt       120 tattaggaag acctcttta gatttctttg acaatgccta tgtgttctat tgatgtagct      180
ttactgtgca tactggtgct ggtctaatta ttccagaaat acaagatgat ggtcaggtat      240
aaacttctat acttgcaaat tacctaaatc tattgggttc ataggcttca aaagcaacat      300
tcataaatga ttgcattttg ctacagttat ggcagtttgg cttctaatct ggatttgttg      360
aagttgccaa actactggat agcgattttt gagtattcaa tttagcaggg gtgctgtttt      420
gatttcaggt caaagtngat atg                                              443
```

<210> SEQ ID NO 71
<211> LENGTH: 443
<212> TYPE: DNA
<213> ORGANISM: Humulus lupulus

<400> SEQUENCE: 71

```
acacacacac acacacacac acacacatat acatataatg taaatgttga tactctattg       60
tgatgatttg cttctgaaac atgatattag aaacaataaa agaacaaag aagtattggt       120 tattaggaag acctctttta gatttctttg acaatgccta tgtgttctat tgatgtagct      180
ttactgtgca tactggtgct ggtctaatta ttccagaaat acaagatgat ggtcaggtat      240
```

```
aaacttctat acttgcaaat tacctaaatc tattgggttc ataggcttca aaagcaacat    300
tcataaatga ttgcattttg ctacagttat ggcagtttgg cttctaatct ggatttgttg    360
aagttgccaa actactggat agcgattttt gagtattcaa tttagcaggg gtgctgtttt    420
gatttcaggt caaagttgat atg                                           443

<210> SEQ ID NO 72
<211> LENGTH: 24
<212> TYPE: DNA
<213> ORGANISM: Humulus lupulus

<400> SEQUENCE: 72
ccccgatgat actttgtaca ctga                                           24

<210> SEQ ID NO 73
<211> LENGTH: 30
<212> TYPE: DNA
<213> ORGANISM: Humulus lupulus

<400> SEQUENCE: 73
ccccgatgat accatgactt tgtacactga                                     30

<210> SEQ ID NO 74
<211> LENGTH: 30
<212> TYPE: DNA
<213> ORGANISM: Humulus lupulus

<400> SEQUENCE: 74
caaccccgat gatactttgt acactgatgc                                     30

<210> SEQ ID NO 75
<211> LENGTH: 15
<212> TYPE: DNA
<213> ORGANISM: Humulus lupulus

<400> SEQUENCE: 75
catgactttg tacac                                                     15

<210> SEQ ID NO 76
<211> LENGTH: 27
<212> TYPE: DNA
<213> ORGANISM: Humulus lupulus

<400> SEQUENCE: 76
aaccccgatg atactttgta cactgat                                        27

<210> SEQ ID NO 77
<211> LENGTH: 14
<212> TYPE: DNA
<213> ORGANISM: Humulus lupulus

<400> SEQUENCE: 77
gatgatacca tgac                                                      14

<210> SEQ ID NO 78
<211> LENGTH: 541
<212> TYPE: DNA
<213> ORGANISM: Humulus lupulus

<400> SEQUENCE: 78
tggtggtgca gaaaagtcag gattttgatg gtggggagtc agagtttagg gccagtgagg    60
aggtagaagt agaagacggt aaaatttgg atggtgggaa tggtaaagat aactctgtca    120
```

```
ttttagaaga gaatgatgag aagttggtcg aagaagatgg ggtgagtctt ggcggagatg        180
agtcagtggt gaaagctgcg cagcttaatg tcccagcttc aagagaagcc gatgttggag        240
tttcagaaga acttgatgaa gctgaaatta gaggtgtaga gcctccagga ggcgggaacc        300
ttggccctgg ttctgcagaa tttgttggca caaagttgat gcctacagat tctgaatctg        360
atggaaatgt tgtggggtct gttactggtg gtcctgatga agttgatacc aagcacgtat        420
cagcaggaga agatggtggg ctaaaagcta attctgaagt tcatcagagc ggccccgtgg        480
tcgagaaagg tgctgataat gaaaaagttc tgtcaggtga tggagttggt ccaaagttga        540
t                                                                       541
```

<210> SEQ ID NO 79
<211> LENGTH: 541
<212> TYPE: DNA
<213> ORGANISM: Humulus lupulus

<400> SEQUENCE: 79

```
tggtggtgca gaaaagtcag gattttgatg gtggggagtc agagtttagg gccagtgagg        60
aggtagaagt agaagacggt aaaattttgg atggtgggaa tggtaaagat aactctgtca        120
ttttagaaga gaatgatgag aagttggtcg aagaagatgg ggtgagtctt ggcggagatg        180
agtcagtggt gaaagctgcg cagcttaatg tcccagcttc aagagaagcc gatgttggag        240
tttcagaaga acttgatgaa gctgaaatta gaggtgtaga gcctccagga ggcgggaacc        300
ttggccctgg ttctgcagaa tttgttggca caaagttgat gcctacagat tctgaatctg        360
atggaaatgt tgtggggtct gttactggtg gtcctgatga agttgatacc aagcacgtat        420
cagcaggaga agatggtggg ctaaaagcta attctgaagt tcatcagagc ggccccgtgg        480
tcgagaaagg tgctgataat gaaaaagttc tgtcaggtga tggagttggt ccaaagttga        540
t                                                                       541
```

<210> SEQ ID NO 80
<211> LENGTH: 541
<212> TYPE: DNA
<213> ORGANISM: Humulus lupulus

<400> SEQUENCE: 80

```
tggtggtgca gaaaagtcag gattttgatg gtggggagtc agagtttagg gccagtgagg        60
aggtagaagt agaagacggt aaaattttgg atggtgggaa tggtaaagat aactctgtca        120
ttttagaaga gaatgatgag aagttggtcg aagaagatgg ggtgagtctt ggcggagatg        180
agtcagtggt gaaagctgcg cagcttaatg tcccagcttc aagagaagcc gatgttggag        240
tttcagaaga acttgatgaa gctgaaatta gaggtgtaga gcctccagga ggcgggaacc        300
ttggccctgg ttctgcagaa tttgttggca caaagttgat gcctacagat tctgaatctg        360
atggaaatgt tgtggggtct gttactggtg gtcctgatga agttgatacc aagcacgtat        420
cagcaggaga agatggtggg ctaaaagcta attctgaagt tcatcagagc ggccccgtgg        480
tcgagaaagg tgctgataat gaaaaagttc tgtcaggtga tggagttggt ccaaagttga        540
t                                                                       541
```

<210> SEQ ID NO 81
<211> LENGTH: 541
<212> TYPE: DNA
<213> ORGANISM: Humulus lupulus

<400> SEQUENCE: 81

```
tggtggtgca gaaaagtcag gattttgatg gtggggagtc agagtttagg gccagtgagg      60
aggtagaagt agaagacggt aaaattttgg atggtgggaa tggtaaagat aactctgtca     120
ttttagaaga gaatgatgag aagttggtcg aagaagatgg ggtgagtctt ggcggagatg     180
agtcagtggt gaaagctgcg cagcttaatg tcccagcttc aagagaagcc gatgttggag     240
tttcagaaga acttgatgaa gctgaaatta gaggtgtaga gcctccagga ggcgggaacc     300
ttggccctgg ttctgcagaa tttgttggca caaagttgat gcctacagat tctgaatctg     360
atggaaatgt tgtggggtct gttactggtg gtcctgatga agttgatacc aagcacgtat     420
cagcaggaga agatggtggg ctaaaagcta attctgaagt tcatcagagc ggccccgtgg     480
tcgagaaagg tgctgataat gaaaaagttc tgtcaggtga tggagttggt ccaaagttga     540
t                                                                     541
```

<210> SEQ ID NO 82
<211> LENGTH: 541
<212> TYPE: DNA
<213> ORGANISM: Humulus lupulus

<400> SEQUENCE: 82

```
tggtggtgca gaaaagtcag gattttgatg gtggggagtc agagtttagg gccagtgagg      60
aggtagaagt agaagatggt aaaattktgg atggtgggaa tgataaagat aactcwgtca     120
wtttwgaaga gaakratgag aagttggtcg aagaagatgg ggtgagtctt ggcggagatg     180
agtcagtggt ggaagctgtg carsttaatg tcccagcttc aagagmagcy gatgytggag     240
tttcagaaga acttgatgaa gctgaaatta gaggtgtaga gcctccagga ggcgggaacc     300
ttggcyctgg ttctgmagaa tttgttggcw caaagttgat gcctacagat tctgaatctg     360
atggaaatgt tgtggggtct gttactggtg gtcctgatga agttgatacc aagcacgtat     420
cagcaggaga agatggtggg ctaaaagcta attctgaagt tcatcagagc ggccccgtgg     480
tcgagaaagg tgctgataat gaaaaagttc tgtcaggtga tggagttggt csaaagttga     540
t                                                                     541
```

<210> SEQ ID NO 83
<211> LENGTH: 541
<212> TYPE: DNA
<213> ORGANISM: Humulus lupulus

<400> SEQUENCE: 83

```
tggtggtgca gaaaagtcag gattttgatg gtggggagtc agagtttagg gccagtgagg      60
aggtagaagt agaagayggt aaaattktgg atggtgggaa tgrtaaagat aactctgtca     120
ttttagaaga gaakratgag aagttggtcg aagaagatgg ggtgagtctt ggcggagatg     180
agtcagtggt graagctgyg cagcttaatg tcccagcttc aagagaagcc gatgttggag     240
tttcagaaga acttgatgaa gctgaaatta gaggtgtaga gcctccagga ggcgggaacc     300
ttggccctgg ttctgcagaa tttgttggca caaagttgat gcctacagat tctgaatctg     360
atggaaatgt tgtggggtct gttactggtg gtcctgatga agttgatacc aagcacgtat     420
cagcaggaga agatggtggg ctaaaagcta attctgaagt tcatcagagc ggccccgtgg     480
tcgagaaagg tgctgataat gaaaaagttc tgtcaggtga tggagttggt ccaaagttga     540
t                                                                     541
```

<210> SEQ ID NO 84
<211> LENGTH: 541
<212> TYPE: DNA
<213> ORGANISM: Humulus lupulus

<400> SEQUENCE: 84

| | | | | | | |
|---|---|---|---|---|---|---|
| tggtggtgca | gaaaagtcag | gattttgatg | gtggggagtc | agagtttagg | gccagtgagg | 60 |
| aggtagaagt | agaagayggt | aaaattttgg | atggtgggaa | tgrtaaagat | aactctgtca | 120 |
| ttttagaaga | gaatgatgag | aagttggtcg | aagaagatgg | ggtgagtctt | ggcggagatg | 180 |
| agtcagtggt | graagctgyg | cagcttaatg | tcccagcttc | aagagaagcc | gatgttggag | 240 |
| tttcagaaga | acttgatgaa | gctgaaatta | gaggtgtaga | gcctccagga | ggcgggaacc | 300 |
| ttggccctgg | ttctgcagaa | tttgttggca | caaagttgat | gcctacagat | tctgaatctg | 360 |
| atggaaatgt | tgtggggtct | gttactggtg | gtcctgatga | agttgatacc | aagcacgtat | 420 |
| cagcaggaga | agatggtggg | ctaaaagcta | attctgaagt | tcatcagagc | ggccccgtgg | 480 |
| tcgagaaagg | tgctgataat | gaaaaagttc | tgtcaggtga | tggagttggt | ccaaagttga | 540 |
| t | | | | | | 541 |

<210> SEQ ID NO 85
<211> LENGTH: 541
<212> TYPE: DNA
<213> ORGANISM: Humulus lupulus

<400> SEQUENCE: 85

| | | | | | | |
|---|---|---|---|---|---|---|
| tggtggtgca | gaaaagtcag | gattttgatg | gtggggagtc | agagtttagg | gccagtgagg | 60 |
| aggtagaagt | agaagayggt | aaaattttgg | atggtgggaa | tgrtaaagat | aactctgtca | 120 |
| ttttagaaga | gaatgatgag | aagttggtcg | aagaagatgg | ggtgagtctt | ggcggagatg | 180 |
| agtcagtggt | graagctgyg | cagcttaatg | tcccagcttc | aagagaagcc | gatgttggag | 240 |
| tttcagaaga | acttgatgaa | gctgaaatta | gaggtgtaga | gcctccagga | ggcgggaacc | 300 |
| ttggccctgg | ttctgcagaa | tttgttggca | caaagttgat | gcctacagat | tctgaatctg | 360 |
| atggaaatgt | tgtggggtct | gttactggtg | gtcctgatga | agttgatacc | aagcacgtat | 420 |
| cagcaggaga | agatggtggg | ctaaaagcta | attctgaagt | tcatcagagc | ggccccgtgg | 480 |
| tcgagaaagg | tgctgataat | gaaaaagttc | tgtcaggtga | tggagttggt | ccaaagttga | 540 |
| t | | | | | | 541 |

<210> SEQ ID NO 86
<211> LENGTH: 645
<212> TYPE: DNA
<213> ORGANISM: Humulus lupulus

<400> SEQUENCE: 86

| | | | | | | |
|---|---|---|---|---|---|---|
| cattcctcag | gatctaaagc | gaattattaa | gaaatacatt | caaatgagat | tgcaagatgg | 60 |
| aaaagatgtg | gacatcgacc | atattttgca | tattcttcct | ttgtcacagg | gaatgctaat | 120 |
| taagaaacac | atgtgtttcc | ctatgttaaa | aaaagtaagt | tatcttttat | agtatatata | 180 |
| tgtcattatt | aagtttgatc | tttaatttga | gctataacat | agtattgtta | tttaattgat | 240 |
| tgattgatta | tatgattaat | tataggttcc | attatttcaa | aacacggatg | aacatgttta | 300 |
| cgaaacaata | tgcaaatatc | tgaaaccagt | cacatattca | gagaaaagtt | atatcattcg | 360 |
| aaaaggagaa | ccacttgata | tgattctctt | catcacacaa | ggtgttgtgt | gggcatttgg | 420 |
| aaatgmtact | actcccataa | gtcgacttca | aaaaggtgat | ttctatggaa | atgaactcat | 480 | agaatggcaa ttaaagtcaa catccattga tgagtttcct atttcggttg ctaatcttaa    540 atcccayacc aatgttgaag ctcttgctct tatggccaat gacttggaac atgtagtctc    600 caattgctgg ttcaagttct cccccacctg ctcatctatg cctga    645

<210> SEQ ID NO 87
<211> LENGTH: 645
<212> TYPE: DNA
<213> ORGANISM: Humulus lupulus

<400> SEQUENCE: 87
cattcctcag gatctaaagc gaattattaa gaaatacatt caaatgagat tgcaagatgg    60
aaaagatgtg gacatcgacc atattttgca tattcttcct ttgtcacagg gaatgctaat    120
taagaaacac atgtgtttcc ctatgttaaa aaaagtaagt tatcttttat agtatatata    180
tgtcattatt aagtttgatc tttaatttga gctataacat agtattgtta tttaattgat    240
tgattgatta tatgattaat tataggttcc attatttcaa aacacggatg aacatgttta    300
cgaaacaata tgcaaatatc tgaaaccagt cacatattca gagaaaagtt atatcattcg    360
aaaaggagaa ccacttgata tgattctctt catcacacaa ggtgttgtgt gggcatttgg    420
aaatgmtact actcccataa gtcgacttca aaaaggtgat ttctatggaa atgaactcat    480
agaatggcaa ttaaagtcaa catccattga tgagtttcct atttcggttg ctaatcttaa    540
atcccatacc aatgttgaag ctcttgctct tatggccaat gacttggaac atgtagtctc    600
caattgctgg ttcaagttct cccccacctg ctcatctatg cctga    645

<210> SEQ ID NO 88
<211> LENGTH: 645
<212> TYPE: DNA
<213> ORGANISM: Humulus lupulus

<400> SEQUENCE: 88
cattcctcag gatctaaagc gaattattaa gaaatacatt caaatgagat tgcaagatgg    60
aaaagatgtg gacatcgacc atattttgca tattcttcct ttgtcacagg gaatgctaat    120
taagaaacac atgtgtttcc ctatgttaaa aaaagtaagt tatcttttat agtatatata    180
tgtcattatt aagtttgatc tttaatttga gctataacat agtattgtta tttaattgat    240
tgattgatta tatgattaat tataggttcc attatttcaa aacacggatg aacatgttta    300
cgaaacaata tgcaaatatc tgaaaccagt cacatattca gagaaaagtt atatcattcg    360
aaaaggagaa ccacttgata tgattctctt catcacacaa ggtgttgtgt gggcatttgg    420
aaatgmtact actcccataa gtcgacttca aaaaggtgat ttctatggaa atgaactcat    480
agaatggcaa ttaaagtcaa catccattga tgagtttcct atttcggttg ctaatcttaa    540
atcccatacc aatgttgaag ctcttgctct tatggccaat gacttggaac atgtagtctc    600
caattgctgg ttcaagttct cccccacctg ctcatctatg cctga    645

<210> SEQ ID NO 89
<211> LENGTH: 645
<212> TYPE: DNA
<213> ORGANISM: Humulus lupulus

<400> SEQUENCE: 89
cattcctcag gatctaaagc gaattattaa gaaatacatt caaatgagat tgcaagatgg    60
aaaagatgtg gacatcgacc atattttgca tattcttcct ttgtcacagg gaatgctaat    120
taagaaacac atgtgtttcc ctatgttaaa aaaagtaagt tatcttttat agtatatrta    180

```
tgtcattatt aagtttgatc tttmatttga gctataacat agtattrtta tttrattgat    240
tgattgatta tatgattaat tataggttcc attatttcaa aacacggatg aacatgttta    300
cgaaacaata tgcaaatatc tgaaccagt cacatattca gagaaaagtt atatcattcg     360
aaaaggagaa ccacttgata tgattctctt catcacacaa ggtgttgtgt gggcatttgg    420
aaatgctact actcccatga gtcgacttca aaaaggtgat ttctatggaa atgaactcat    480
agaatggcaa ttaaagtcaa catccattga tgagtttcct atttcggttg ctaatcttaa    540
atcccatacc aatgttgaag ctcttgctct tatggccaat gacttggaac atgtagtctc    600
caattgctgg ttcaagttct cccscacctg ctcatctatg cctga                   645
```

<210> SEQ ID NO 90
<211> LENGTH: 641
<212> TYPE: DNA
<213> ORGANISM: Humulus lupulus

<400> SEQUENCE: 90

```
cattcctcag gatctaaagc gaattattaa gaaatacatt caaatgagat tgcaagatgg    60
aaaagatgtg gacatcgacc atattttgca tattcttcct ttgtcacagg gaatgctaat   120
taagaaacac atgtgtttcc ctatgttaaa aaaagtaagt tatcttttat agtatatrta   180
tgtcattatt aagtttgatc tttmatttga gctataacat agtattrtta tttrattgat   240
tgattatatg attaattata ggttccatta tttcaaaaca cggatgaaca tgtttacgaa   300
acaatatgca aatatctgaa accagtcaca tattcagaga aaagttatat cattcgaaaa   360
ggagaaccac ttgatatgat tctcttcatc acacaaggtg ttgtgtgggc atttggaaat   420
gatactactc ccatgagtcg acttcaaaaa ggtgatttct atggaaatga actcatagaa   480
tggcaattaa agtcaacatc cattgatgag tttcctattt cggttgctaa tcttaaatcc   540
cataccaatg ttgaagccct tgctcttatg gccaatgact tggaacatgt agtctccaat   600
tgctggttca agttctcccs cacctgctca tctatgcctg a                       641
```

<210> SEQ ID NO 91
<211> LENGTH: 645
<212> TYPE: DNA
<213> ORGANISM: Humulus lupulus

<400> SEQUENCE: 91

```
cattcctcag gatctaaagc gaattattaa gaaatacatt caaatgagat tgcaagatgg    60
aaaagatgtg gacatcgacc atattttgca tattcttcct ttgtcacagg gaatgctaat   120
taagaaacac atgtgtttcc ctatgttaaa aaaagtaagt tatcttttat agtatatata   180
tgtcattatt aagtttgatc tttaatttga gctataacat agtattgtta tttaattgat   240
tgattgatta tatgattaat tataggttcc attatttcaa aacacggatg aacatgttta   300
cgaaacaata tgcaaatatc tgaaccagt cacatattca gagaaaagtt atatcattcg    360
aaaaggagaa ccacttgata tgattctctt catcacacaa ggtgttgtgt gggcatttgg   420
aaatgctact actcccataa gtcgacttca aaaaggtgat ttctatggaa atgaactcat   480
agaatggcaa ttaaagtcaa catccattga tgagtttcct atttcggttg ctaatcttaa   540
atcccatacc aatgttgaag ctcttgctct tatggccaat gacttggaac atgtagtctc   600
caattgctgg ttcaagttct cccccacctg ctcatctatg cctga                   645
```

<210> SEQ ID NO 92

<211> LENGTH: 645
<212> TYPE: DNA
<213> ORGANISM: Humulus lupulus

<400> SEQUENCE: 92

```
cattcctcag gatctaaagc gaattattaa gaaatacatt caaatgagat tgcaagatgg    60
aaaagatgtg gacatcgacc atattttgca tattcttcct ttgtcacagg gaatgctaat   120
taagaaacac atgtgtttcc ctatgttaaa aaaagtaagt tatcttttat agtatatata   180
tgtcattatt aagtttgatc tttaatttga gctataacat agtattgtta tttaattgat   240
tgattgatta tatgattaat tataggttcc attatttcaa aacacggatg aacatgttta   300
cgaaacaata tgcaaatatc tgaaaccagt cacatattca gagaaaagtt atatcattcg   360
aaaaggagaa ccacttgata tgattctctt catcacacaa ggtgttgtgt gggcatttgg   420
aaatgctact actcccataa gtcgacttca aaaaggtgat ttctatggaa atgaactcat   480
agaatggcaa ttaaagtcaa catccattga tgagtttcct atttcggttg ctaatcttaa   540
atcccatacc aatgttgaag ctcttgctct tatggccaat gacttggaac atgtagtctc   600
caattgctgg ttcaagttct cccccacctg ctcatctatg cctga                  645
```

<210> SEQ ID NO 93
<211> LENGTH: 645
<212> TYPE: DNA
<213> ORGANISM: Humulus lupulus

<400> SEQUENCE: 93

```
cattcctcag gatctaaagc gaattattaa gaaatacatt caaatgagat tgcaagatgg    60
aaaagatgtg gacatcgacc atattttgca tattcttcct ttgtcacagg gaatgctaat   120
taagaaacac atgtgtttcc ctatgttaaa aaaagtaagt tatcttttat agtatatata   180
tgtcattatt aagtttgatc tttaatttga gctataacat agtattgtta tttaattgat   240
tgattgatta tatgattaat tataggttcc attatttcaa aacacggatg aacatgttta   300
cgaaacaata tgcaaatatc tgaaaccagt cacatattca gagaaaagtt atatcattcg   360
aaaaggagaa ccacttgata tgattctctt catcacacaa ggtgttgtgt gggcatttgg   420
aaatgctact actcccataa gtcgacttca aaaaggtgat ttctatggaa atgaactcat   480
agaatggcaa ttaaagtcaa catccattga tgagtttcct atttcggttg ctaatcttaa   540
atcccatacc aatgttgaag ctcttgctct tatggccaat gacttggaac atgtagtctc   600
caattgctgg ttcaagttct cccccacctg ctcatctatg cctga                  645
```

<210> SEQ ID NO 94
<211> LENGTH: 645
<212> TYPE: DNA
<213> ORGANISM: Humulus lupulus

<400> SEQUENCE: 94

```
cattcctcag gatctaaagc gaattattaa gaaatacatt caaatgagat tgcaagatgg    60
aaaagatgtg gacatcgacc atattttgca tattcttcct ttgtcacagg gaatgctaat   120
taagaaacac atgtgtttcc ctatgttaaa aaaagtaagt tatcttttat agtatatata   180
tgtcattatt aagtttgatc tttaatttga gctataacat agtattgtta tttaattgat   240
tgattgatta tatgattaat tataggttcc attatttcaa aacacggatg aacatgttta   300
cgaaacaata tgcaaatatc tgaaaccagt cacatattca gagaaaagtt atatcattcg   360
aaaaggagaa ccacttgata tgattctctt catcacacaa ggtgttgtgt gggcatttgg   420
```

```
aaatgctact actcccataa gtcgacttca aaaaggtgat ttctatggaa atgaactcat    480
agaatggcaa ttaaagtcaa catccattga tgagtttcct atttcggttg ctaatcttaa    540
atcccatacc aatgttgaag ctcttgctct tatggccaat gacttggaac atgtagtctc    600
caattgctgg ttcaagttct cccccacctg ctcatctatg cctga                   645
```

```
<210> SEQ ID NO 95
<211> LENGTH: 559
<212> TYPE: DNA
<213> ORGANISM: Humulus lupulus

<400> SEQUENCE: 95
tttgacgtga tcgagtggag tggtggtata tacgttccat attataaaga ttacattgtt     60
ttaatggata taccagggaa ggagaattta aaactctcca tcgcactgca agccaacccc    120
gatgatacca tgactttgta cactgatgcc atcttgaatg gcatcgaaat cttcaaatta    180
agcgactcca acggaaatct cgccggtctg aatcttgacc ttgttccgca tgcgaagcca    240
ccaagccaac catcatggaa gttgaaaaat catcaatcag agattattgg catttccatt    300
ggtgtagttt gcagcgttgt tttgctctgc ataattggat tcctatttct ccggcgaggt    360
agaaaagtca aggaacaat gctcatttcc ttgtcaacta ccaggtcaag caagaccgga    420
gaatcatcat tgccgttgga tcggtgtcgt tactttcac tggctgagat cattactgca    480
gcaaacaact tcgaagatat tttcattatt ggggttggag gattcggaaa cgtgtataaa    540
gggcacatcg acaatggga                                                 559
```

```
<210> SEQ ID NO 96
<211> LENGTH: 553
<212> TYPE: DNA
<213> ORGANISM: Humulus lupulus

<400> SEQUENCE: 96
tttgacgtga tcgagtggag tggtggtata tacgttccat attataaaga ttacattgtt     60
ttaatggata taccagggaa ggagaaagta aaactctcca tcgcactgca agccaacccc    120
gatgatactt tgtacactga tgccatcttg aatggcatcg aaatcttcaa attaagcgac    180
tccaacggaa atctcgccgg tctgaatctt gaccttgttc cgcatgcgaa gccaccaagc    240
caaccatcat ggaagttgaa aaatcatcaa tcagagatta ttggcatttc cattggtgta    300
gtttgcagcg ttgttttgct ctgcataatt ggattcctat ttctccggcg aggtagaaaa    360
gtcaaaggca aaggctcat ttccttgtca actaccaggt caagcaagac cggagaatca    420
tcattgccgt tggatcggtg tcgttacttt tcactggctg agatcattac tgcagcaaac    480
aacttcgaag atatttttcat tattggggtt ggaggattcg gaaacgtgta aagggcac    540 atcgacaatg gga                                                       553
```

```
<210> SEQ ID NO 97
<211> LENGTH: 553
<212> TYPE: DNA
<213> ORGANISM: Humulus lupulus

<400> SEQUENCE: 97
tttgacgtga tccagtggag tggtggtata tacgttccat attataaaga ttacattgtt     60
ttaatggata taccagggaa ggagaaagta aaactctcca tcgcactgca agccaacccc    120
gatgatactt tgtacactga tgccatcttg aatggcatcg aaatcttcaa attaagcgac    180
```

```
tccaacggaa atctcgccgg tctgaatctt gaccttgttc cgcatgcgaa gccaccaagc    240
caaccattat ggaagttgaa aaatcatcaa tcagagatta ttggcatttc cattggtgta    300
gtttgcagcg ttgttttgct ctgcataatt ggattcctat ttctccggcg aggtagaaaa    360
gtcaaaggca caaggctcat ttccttgtct acaaccaggt caagcaagac cggaaaatca    420
tcattgccgt tggatcggtg tcgttacttt tcattggctg agatcattac tgcaacaaac    480
aacttcgaag atattttcat tattggggtt ggaggattcg gaaacgtgta taagggcac     540 atcgacaatg gga                                                       553
```

```
<210> SEQ ID NO 98
<211> LENGTH: 553
<212> TYPE: DNA
<213> ORGANISM: Humulus lupulus

<400> SEQUENCE: 98
tttgacgtga tccagtggag tggtggtata tacgttccat attataaaga ttacattgtt    60
ttaatggata taccagggaa ggagaaagta aaactctcca tcgcactgca agccaacccc    120
gatgatactt tgtacactga tgccatcttg aatggcatcg aaatcttcaa attaagcgac    180
tccaacggaa atctcgccgg tctgaatctt gaccttgttc cgcatgcgaa gccaccaagc    240
caaccattat ggaagttgaa aaatcatcaa tcagagatta ttggcatttc cattggtgta    300
gtttgcagcg ttgttttgct ctgcataatt ggattcctat ttctccggcg aggtagaaaa    360
gtcaaaggca caaggctcat ttccttgtct acaaccaggt caagcaagac cggaaaatca    420
tcattgccgt tggatcggtg tcgttacttt tcattggctg agatcattac tgcaacaaac    480
aacttcgaag atattttcat tattggggtt ggaggattcg gaaacgtgta taagggcac     540 atcgacaatg gga                                                       553
```

```
<210> SEQ ID NO 99
<211> LENGTH: 553
<212> TYPE: DNA
<213> ORGANISM: Humulus lupulus

<400> SEQUENCE: 99
tttgacgtga tccagtggag tggtggtata tacgttccat attataaaga ttacattgtt    60
ttaatggata taccagggaa ggagaaagta aaactctcca tcgcactgca agccaacccc    120
gatgatactt tgtacactga tgccatcttg aatggcatcg aaatcttcaa attaagcgac    180
tccaacggaa atctcgccgg tctgaatctt gaccttgttc cgcatgcgaa gccaccaagc    240
caaccattat ggaagttgaa aaatcatcaa tcagagatta ttggcatttc cattggtgta    300
gtttgcagcg ttgttttgct ctgcataatt ggattcctat ttctccggcg aggtagaaaa    360
gtcaaaggca caaggctcat ttccttgtct acaaccaggt caagcaagac cggaaaatca    420
tcattgccgt tggatcggtg tcgttacttt tcattggctg agatcattac tgcaacaaac    480
aacttcgaag atattttcat tattggggtt ggaggattcg gaaacgtgta taagggcac     540 atcgacaatg gga                                                       553
```

```
<210> SEQ ID NO 100
<211> LENGTH: 553
<212> TYPE: DNA
<213> ORGANISM: Humulus lupulus

<400> SEQUENCE: 100
tttgacgtga tccagtggag tggtggtata tacgttccat attataaaga ttacattgtt    60
```

```
ttaatggata taccagggaa ggagaaagta aaactctcca tcgcactgca agccaacccc      120
gatgatactt tgtacactga tgccatcttg aatggcatcg aaatcttcaa attaagcgac      180
tccaacggaa atctcgccgg tctgaatctt gaccttgttc cgcatgcgaa gccaccaagc      240
caaccattat ggaagttgaa aaatcatcaa tcagagatta ttggcatttc cattggtgta      300
gtttgcagcg ttgttttgct ctgcataatt ggattcctat ttctccggcg aggtagaaaa      360
gtcaaaggca caaggctcat ttccttgtct acaaccaggt caagcaagac cggaaaatca      420
tcattgccgt tggatcggtg tcgttacttt tcattggctg agatcattac tgcaacaaac      480
aacttcgaag atattttcat tattggggtt ggaggattcg gaaacgtgta taagggcac       540 atcgacaatg gga                                                        553

<210> SEQ ID NO 101
<211> LENGTH: 559
<212> TYPE: DNA
<213> ORGANISM: Humulus lupulus

<400> SEQUENCE: 101
tttgacgtga tccagtggag tggtggtata tacgttccat attataaaga ttacattgtt       60
ttaatggata taccaaagaa ggagaaagta aacctctcca tcgcactgca agccaacccc      120
gatgatacga tgactctcta cactgatgcc atcttgaatg gcgtggaaat cttcaaatta      180
agcgactcca acggaaatct cgccggtctg aatcttgacc ttgttccgca tgcgaagcca      240
ccaaaccaac cattatggaa gttgaaaaat catcaatcag agattattgg catttccatt      300
ggtgtagttt gctgcgttgt cttgctctgc ataattggat tcctatttct ccggcgaggt      360
agaaaagtca aaagctcaag gctcatttcc ttgtccacaa ccaggtcaag caagaccgga      420
aaatcatcat tgccatttga tcggtgtcgt tacttttcat tggctgagat cataaccgcc      480
acaaacaact tcgaagatat tttcattatt ggggttggag gattcggaaa cgtgtataaa      540
gggcacatcg acaatggga                                                  559

<210> SEQ ID NO 102
<211> LENGTH: 553
<212> TYPE: DNA
<213> ORGANISM: Humulus lupulus

<400> SEQUENCE: 102
tttgacgtga tccagtggag tggtggtata tacgttccat attataaaga ttacattgtt       60
ttaatggata taccagggaa ggagaaagta aaactctcca tcgcactgca agccaacccc      120
gatgatactt tgtacactga tgccatcttg aatggcatcg aaatcttcaa attaagcgac      180
tccaacggaa atctcgccgg tctgaatctt gaccttgttc cgcatgcgaa gccaccaagc      240
caaccattat ggaagttgaa aaatcatcaa tcagagatta ttggcatttc cattggtgta      300
gtttgcagcg ttgttttgct ctgcataatt ggattcctat ttctccggcg aggtagaaaa      360
gtcaaaggca caaggctcat ttccttgtct acaaccaggt caagcaagac cggaaaatca      420
tcattgccgt tggatcggtg tcgttacttt tcattggctg agatcattac tgcaacaaac      480
aacttcgaag atattttcat tattggggtt ggaggattcg gaaacgtgta taagggcac       540 atcgacaatg gga                                                        553

<210> SEQ ID NO 103
<211> LENGTH: 553
<212> TYPE: DNA
```

<213> ORGANISM: Humulus lupulus

<400> SEQUENCE: 103

```
tttgacgtga tccagtggag tggtggtata tacgttccat attataaaga ttacattgtt    60
ttaatggata taccagggaa ggagaaagta aaactctcca tcgcactgca agccaacccc   120
gatgatactt tgtacactga tgccatcttg aatggcatcg aaatcttcaa attaagcgac   180
tccaacggaa atctcgccgg tctgaatctt gaccttgttc cgcatgcgaa gccaccaagc   240
caaccattat ggaagttgaa aaatcatcaa tcagagatta ttggcatttc cattggtgta   300
gtttgcagcg ttgttttgct ctgcataatt ggattcctat ttctccggcg aggtagaaaa   360
gtcaaaggca caaggctcat ttccttgtct acaaccaggt caagcaagac cggaaaatca   420
tcattgccgt tggatcggtg tcgttacttt tcattggctg agatcattac tgcaacaaac   480
aacttcgaag atattttcat tattggggtt ggaggattcg gaaacgtgta taagggcac    540
atcgacaatg gga                                                      553
```

<210> SEQ ID NO 104
<211> LENGTH: 553
<212> TYPE: DNA
<213> ORGANISM: Humulus lupulus

<400> SEQUENCE: 104

```
tttgacgtga tccagtggag tggtggtata tacgttccat attataaaga ttacattgtt    60
ttaatggata taccagggaa ggagaaagta aaactctcca tcgcactgca agccaacccc   120
gatgatactt tgtacactga tgccatcttg aatggcatcg aaatcttcaa attaagcgac   180
tccaacggaa atctcgccgg tctgaatctt gaccttgttc cgcatgcgaa gccaccaagc   240
caaccattat ggaagttgaa aaatcatcaa tcagagatta ttggcatttc cattggtgta   300
gtttgcagcg ttgttttgct ctgcataatt ggattcctat ttctccggcg aggtagaaaa   360
gtcaaaggca caaggctcat ttccttgtct acaaccaggt caagcaagac cggaaaatca   420
tcattgccgt tggatcggtg tcgttacttt tcattggctg agatcattac tgcaacaaac   480
aacttcgaag atattttcat tattggggtt ggaggattcg gaaacgtgta taagggcac    540
atcgacaatg gga                                                      553
```

<210> SEQ ID NO 105
<211> LENGTH: 645
<212> TYPE: DNA
<213> ORGANISM: Humulus lupulus
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (227)..(227)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (245)..(248)
<223> OTHER INFORMATION: n is a, c, g, or t
<220> FEATURE:
<221> NAME/KEY: misc_feature
<222> LOCATION: (245)..(248)
<223> OTHER INFORMATION: n is a, c, g, t, or no nucleobase (deletion)
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (562)..(562)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t

<400> SEQUENCE: 105

```
cattcctcag gatctaaagc gaattattaa gaaatacatt caaatgagat tgcaagatgg      60
aaaagatgtg gacatcgacc atattttgca tattcttcct ttgtcacagg gaatgctaat     120
taagaaacac atgtgtttcc ctatgttaaa aaaagtaagt tatcttttat agtatatnta     180
tgtcattatt aagtttgatc tttnatttga gctataacat agtattntta tttnattgat     240
tgatnnnnta tatgattaat tataggttcc attatttcaa aacacggatg aacatgttta     300
cgaaacaata tgcaaatatc tgaaaccagt cacatattca gagaaaagtt atatcattcg     360
aaaaggagan ccacttgata tgattctctt catcacacaa ggtgttgtgt gggcatttgg     420
aaatgntact actcccatna gtcgacttca aaaaggtgat ttctatggaa atgaactcat     480
agaatggcaa ttaaagtcaa catccattga tgagtttcct atttcggttg ctaatcttaa     540
atcccanacc aatgttgaag cncttgctct tatggccaat gacttggaac atgtagtctc     600
caattgctgg ttcaagttct cccncacctg ctcatctatg cctga                    645
```

<210> SEQ ID NO 106
<211> LENGTH: 559
<212> TYPE: DNA
<213> ORGANISM: Humulus lupulus
<220> FEATURE:
<221> NAME/KEY: misc_feature
<222> LOCATION: (3)..(3)
<223> OTHER INFORMATION: n is a, c, g, t
<220> FEATURE:
<221> NAME/KEY: misc_feature
<222> LOCATION: (13)..(13)
<223> OTHER INFORMATION: n is a, c, g, t
<220> FEATURE:
<221> NAME/KEY: misc_feature
<222> LOCATION: (17)..(17)
<223> OTHER INFORMATION: n is a, c, g, t
<220> FEATURE:
<221> NAME/KEY: misc_feature
<222> LOCATION: (76)..(77)
<223> OTHER INFORMATION: n is a, c, g, t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (87)..(88)

```
<223> OTHER INFORMATION: n is a, c, g, t
<220> FEATURE:
<221> NAME/KEY: misc_feature
<222> LOCATION: (93)..(93)
<223> OTHER INFORMATION: n is a, c, g, t
<220> FEATURE:
<221> NAME/KEY: misc_feature
<222> LOCATION: (129)..(134)
<223> OTHER INFORMATION: n is a, c, g, t, or no nucleobase (deletion)
<220> FEATURE:
<221> NAME/KEY: misc_feature
<222> LOCATION: (136)..(136)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (163)..(163)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (254)..(254)
<223> OTHER INFORMATION: n is a, c, g, or t
<220> FEATURE:
<221> NAME/KEY: misc_feature
<222> LOCATION: (313)..(313)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (375)..(376)
<223> OTHER INFORMATION: n is a, c, g, or t
<220> FEATURE:
<221> NAME/KEY: misc_feature
<222> LOCATION: (380)..(380)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (398)..(399)
<223> OTHER INFORMATION: n is a, c, g, or t
<220> FEATURE:
<221> NAME/KEY: misc_feature
<222> LOCATION: (421)..(421)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
```

```
<222> LOCATION: (438)..(438)
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (474)..(477)
<223> OTHER INFORMATION: n is a, c, g, or t
<220> FEATURE:
<221> NAME/KEY: misc_feature
<222> LOCATION: (480)..(481)
<223> OTHER INFORMATION: n is a, c, g, or t
<220> FEATURE:
<221> NAME/KEY: misc_feature
<222> LOCATION: (500)..(500)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t

<400> SEQUENCE: 106
ttngacgtga tcnagtngag tggtggtata tacgttccat attataaaga ttacattgtt    60
ttaatggata taccanngan ggagaannta aanctctcca tcgcactgca agccaacccc   120
gatgatacnn nnnntntnta cactgatgcc atcttgaatg gcntngaaat cttcaaatta   180
agcgactcca acggaaatct cgccggtctg aatcttgacc ttgttccgca tgcgaagcca   240
ccaanccaac catnatggaa gttgaaaaat catcaatcag agattattgg catttccatt   300
ggtgtagttt gcngcgttgt nttgctctgc ntaattggat tcctatttct ccggcnaggt   360
agaaaagtca aangnncaan gctcatttcc ttgtcnanna ccaggtcaag caagaccgga   420
naatcatcat tgccnttnga tcggtgtcgt tacttttcan tggctgagat catnnnngcn   480
ncaaacaact tcgaagatan tttcattatt ggggttggag gattcggaaa cgtgtataaa   540
gggcacntcg acaatggga                                                559

<210> SEQ ID NO 107
<211> LENGTH: 542
<212> TYPE: DNA
<213> ORGANISM: Humulus lupulus
<220> FEATURE:
<221> NAME/KEY: misc_feature
<222> LOCATION: (3)..(3)
<223> OTHER INFORMATION: n is a,c, g, or t
<220> FEATURE:
<221> NAME/KEY: misc_feature
<222> LOCATION: (8)..(3)
<223> OTHER INFORMATION: n is a,c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (19)..(20)
<223> OTHER INFORMATION: n is a,c, g, or t
<220> FEATURE:
<221> NAME/KEY: misc_feature
<222> LOCATION: (27)..(28)
<223> OTHER INFORMATION: n is a,c, g, or t
<220> FEATURE:
<221> NAME/KEY: misc_feature
<222> LOCATION: (40)..(41)
<223> OTHER INFORMATION: n is a,c, g, or t
<220> FEATURE:
<221> NAME/KEY: misc_feature
<222> LOCATION: (46)..(47)
<223> OTHER INFORMATION: n is a,c, g, or t
<220> FEATURE:
```

```
<221> NAME/KEY: misc_feature
<222> LOCATION: (57)..(57)
<223> OTHER INFORMATION: n is a,c, g, or t
<220> FEATURE:
<221> NAME/KEY: misc_feature
<222> LOCATION: (64)..(85)
<223> OTHER INFORMATION: n is a,c, g, t, or no nucleobase (deletion)
<220> FEATURE:
<221> NAME/KEY: misc_feature
<222> LOCATION: (90)..(90)
<223> OTHER INFORMATION: n is a,c, g, or t
<220> FEATURE:
<221> NAME/KEY: misc_feature
<222> LOCATION: (112)..(112)
<223> OTHER INFORMATION: n is a,c, g, or t
<220> FEATURE:
<221> NAME/KEY: misc_feature
<222> LOCATION: (116)..(116)
<223> OTHER INFORMATION: n is a,c, g, or t
<220> FEATURE:
<221> NAME/KEY: misc_feature
<222> LOCATION: (118)..(118)
<223> OTHER INFORMATION: n is a,c, g, or t
<220> FEATURE:
<221> NAME/KEY: misc_feature
<222> LOCATION: (120)..(131)
<223> OTHER INFORMATION: n is a,c, g, t or no nucleobase (deletion)
<220> FEATURE:
<221> NAME/KEY: misc_feature
<222> LOCATION: (140)..(140)
<223> OTHER INFORMATION: n is a,c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (166)..(166)
<223> OTHER INFORMATION: n is a,c, g, or t
<220> FEATURE:
<221> NAME/KEY: misc_feature
<222> LOCATION: (178)..(178)
<223> OTHER INFORMATION: n is a,c, g, or t
<220> FEATURE:
<221> NAME/KEY: misc_feature
<222> LOCATION: (191)..(192)
<223> OTHER INFORMATION: n is a,c, g, or t
<220> FEATURE:
<221> NAME/KEY: misc_feature
<222> LOCATION: (244)..(244)
<223> OTHER INFORMATION: n is a, c, g, or t
<220> FEATURE:
<221> NAME/KEY: misc_feature
<222> LOCATION: (266)..(266)
<223> OTHER INFORMATION: n is a,c, g, or t
<220> FEATURE:
<221> NAME/KEY: misc_feature
<222> LOCATION: (271)..(271)
<223> OTHER INFORMATION: n is a,c, g, or t
<220> FEATURE:
<221> NAME/KEY: misc_feature
<222> LOCATION: (377)..(377)
<223> OTHER INFORMATION: n is a,c, g, or t
<220> FEATURE:
<221> NAME/KEY: misc_feature
<222> LOCATION: (430)..(430)
<223> OTHER INFORMATION: n is a,c, g, or t

<400> SEQUENCE: 107
agnacgangc tttgcccgnn ttattgnnga gcttgagaan ntgcanngaa agcacangta      60
acannnnnnn nnnnnnnnnn nnnnntatan acacacacac acacacacac anacananan     120
nnnnnnnnnn ntatacatan aatgtaaatg ttgatnctct attgtgatga tttgcttntg     180
aaacatgata nnagaaacaa taaaaagaac aagaagtat tggttattag gaagacctct      240
tttngatttc tttgacaatg cctatntgtt ntattgatgt agctttactg tgcatactgg     300
```

```
tgctggtcta attattccag aaatacaaga tgatggtcag gtataaactt ctatacttgc    360
aaattaccta aatctantgg gttcataggc ttcaaaagca acattcataa atgattgcat    420
tttgctacan ttatggcagt ttggcttcta atctggattt gttgaagttg ccaaactact    480
ggatagcgat ttttgagtat tcaatttagc aggggtgctg ttttgatttc aggtcaaagt    540
ga                                                                   542

<210> SEQ ID NO 108
<211> LENGTH: 168
<212> TYPE: DNA
<213> ORGANISM: Humulus lupulus

<400> SEQUENCE: 108
agcacgatgc tttgcccgat ttattgctga gcttgagaat ttgcaaggaa agcacaggta     60
acatatctat agacctatac atgcatatat acacacacac acacacacac acacacacat    120
atacatataa tgtaaatgtt gatactctat tgtgatgatt tgcttctg                 168

<210> SEQ ID NO 109
<211> LENGTH: 146
<212> TYPE: DNA
<213> ORGANISM: Humulus lupulus

<400> SEQUENCE: 109
agtacgatgc tttgcccgat ttattgtcga gcttgagaat ttgcaaagaa agcacaggta     60
acatatacac acacacacac acacacacat acatatatat acatagaatg taaatgttga    120
ttctctattg tgatgatttg cttttg                                         146

<210> SEQ ID NO 110
<211> LENGTH: 180
<212> TYPE: DNA
<213> ORGANISM: Humulus lupulus

<400> SEQUENCE: 110
agcacgaggc tttgcccgcg ttattgctga gcttgagaaa atgcacggaa agcacacgta     60
acacatatat agacatatac atgcatatat acacacacac acacacacac acacacac     120 acacacacac atatacatat aatgtaaatg ttgatactct attgtgatga tttgcttctg    180
```

METHOD FOR IDENTIFYING VARIETY OF HOP

TECHNICAL FIELD

The present invention relates to a method for identifying the varieties of hops using an identification marker composed of at least one single nucleotide polymorphism that differs among varieties, and a method for preparing said identification marker.

BACKGROUND ART

Hop (scientific name: *Humulus lupulus*) is a dioecious climbing plant belonging to the Cannabaceae family. The female plant of hop produces flower-like cones, called strobilus, like those of a pine tree, and these cones are used as an ingredient of beer. Unfertilized cones contain yellow grains called lupulin, which give the unique flavor and refreshing bitterness of beer. Hop is one of the essential ingredients for brewing beer in that it has various functions, such as imparting bittersweet and refreshing flavor, improving froth retention, improving the luster of beer, and reducing the growth of saprophytic bacteria.

Hops are cultivated mainly in various countries, including Germany, the U.S., and other countries such as Czech, the U.K., France, China, Slovenia, South Africa, Australia, New Zealand, and Japan, and the varieties of hops cultivated are wide-ranging. The varieties of hops are broadly divided into two categories: aromatic hops and bittering hops. Aromatic hops impart luxurious flavor and mild bitterness, and bittering hops give crisp bitterness. As such, hops produce different flavors and tastes depending on the variety, so in order to brew high-quality beer, it is important to select a hop variety suited to the purpose. Further, in order to maintain the quality of beer in a stable manner, it is important to strictly check to see if hops as a raw material are delivered correctly as ordered. Hitherto, checking has been made on the basis of quality assurance certificates provided by suppliers, the differences in the contents of various components including α-acid in lupulin, or the difference in the appearance of cones. However, the hop cones commonly purchased and used for brewing beers in Japan are those which have been dried, crushed, and compressed into pellets in advance. Thus, it is very difficult to identify hop varieties from the appearance characteristics of their cones. In addition, chemical components obtained from cones, such as bittering components and essential oil components, are susceptible to environmental factors, and those components from some varieties show similar values; so there has been a limit to using those components as indicators for identification.

Meanwhile, there have in recent years been developed several variety identification methods to which genetic engineering is applied. These methods identify varieties by detecting a difference in nucleotide sequence among the varieties, in other words polymorphism. In the field of hops, International Patent Publication No. WO 1997/005281 discloses a hop variety identification method in which a DNA region that differs among varieties is detected by the RAPD method, primers capable of amplifying the region are designed, the polymorphic region is amplified by PCR using the primers, and the presence or absence of amplified fragments, or the difference in size among them, is analyzed, whereby the hop varieties are identified. Japanese Patent Application Publication No. JP H11-103895 also discloses a hop variety discrimination method in which a genomic DNA suitable for PCR is efficiently extracted and purified from a hop by using a high concentration of lithium chloride, the genomic DNA is subjected to PCR using primers such as random primers and STS primers, to thereby amplify a DNA that enables identification of the variety of the hop, and the hop variety is discriminated according to the presence or absence of an amplified DNA. Japanese Patent Application Publication No. JP 2006-34142 further discloses a variety identification method in which a microsatellite DNA region containing a polymorphism among varieties is amplified by performing PCR using primers designed to be capable of amplifying the region, and a difference in length among amplified DNA fragments is analyzed to identify the varieties.

The above-mentioned methods, in which hop varieties are identified using a polymorphism(s) on hop genomes, are effective in that they allow exact identification of hop varieties without being affected by the cultivation environment, harvest timing, or storage method of hops. However, since these methods all make identification based on the presence or absence of amplification by PCR, or on a difference in amplification product size, these are susceptible to variations in conditions for enzymatic reaction, electrophoresis, gel staining, or the like, and are problematic in reproducibility. In other words, it is difficult to distinguish whether no band appears due to any failure of PCR or staining, or no amplification occurs originally, so there is a risk of misinterpreting the results. Further, the above-mentioned methods detect DNA fragments by capillary electrophoresis and laser irradiation, by staining of samples for gel electrophoresis, or by other similar means; thus, though they can at least identify the varieties of hops to be tested or deduce the presence or absence of mixing of a different variety of hop, they cannot go so far as to deduce or identify the variety of the hop mixed or to analyze the proportion of the hop variety mixed. Furthermore, in a case where a DNA is fragmented due to, for example, deterioration of or damage to a test substance, there occurs a decrease in accuracy of analysis, thereby posing a risk of misinterpreting the results.

Single nucleotide polymorphism (hereinafter also referred to as "SNP") is attracting attention as a very useful and easy-to-use polymorphic marker. SNP is a polymorphism in nucleotide sequence caused by a difference at a single nucleotide. SNP is insusceptible to variations in reaction conditions, and hence produces no false results and is easy to determine. Further, SNP data can be converted to a digital signal consisting of 0 and 1 and be information-processed, so that sample processing and data analysis can be automated easily and also various analyses can be made using an enormous amount of SNP data. Furthermore, it is possible to make many SNP analyses at one time, for example, through designing primers with non-specific tails of different lengths.

However, hop has 20 diploid chromosomes (10 pairs of double strands) and a huge genome size of about 2.7 to 3 billion base pairs (2.7-3 GB), and also has not been made clear as to its relationship with its structural genes. Therefore, from the results of genomic analysis, there has not been found such a sufficient number of SNPs among hop varieties that allow identification of many varieties, and there has not yet been known a method for identifying hop varieties using a SNP as a polymorphic marker.

PRIOR ART DOCUMENTS

Patent Documents

Patent Document 1: International Patent Publication No. WO 1997/005281
Patent Document 2: Japanese Patent Application Publication No. JP H11-103895
Patent Document 3: Japanese Patent Application Publication No. JP 2006-34142

SUMMARY OF THE INVENTION

Problems to be Solved by the Invention

The present invention provides a method for identifying the varieties of hops using an identification marker composed of a single nucleotide polymorphism among varieties, as well as a method for preparing said identification marker.

In other words, there has been a strong demand to develop such a hop variety identification method that, when it is determined whether a hop delivered as a raw material is of the same variety as the ordered one or whether a different variety of hop is mixed, the variety of the hop delivered can be identified accurately without being affected by variations in conditions for enzymatic reaction, electrophoresis, gel staining, or the like, or the presence or absence of mixing of a different variety can be detected, and in addition, if a different variety of hop is mixed, the variety of the hop mixed can be deduced or identified, or the proportion of the hop variety mixed can be analyzed.

Means for Solving the Problems

In order to solve the above-mentioned problems, the present inventors have made intensive studies on a method for identifying the varieties of hops on the basis of DNA analysis. Speaking of DNA analysis, there have hitherto been reported various DNA analysis methods based on a difference in size, or the presence or absence, of PCR amplification products or restriction enzyme fragments thereof, as exemplified by SSR, RAPD, RFLP, and AFLP. However, many of these methods are complicated in procedure and susceptible to variations in conditions for enzymatic reaction, electrophoresis, gel staining, or the like, and are of concern in terms of reproducibility. In addition, if a different variety is mixed, these methods may often encounter difficulty in detection. The inventors have obtained a large amount of data using an ultrafast DNA nucleotide sequence analysis technique that has progressed in recent years, searched for SNPs more extensively and efficiently, and developed a method for accurately and easily identifying the varieties of hops using these SNPs as an identification marker.

More specifically, in one mode, the present invention can be as follows.
(1) A method for identifying the varieties of hops, the method comprising the steps of:
(i) amplifying fragments of DNAs derived from hops to be tested, the fragments which each comprise a variety identification region, wherein the variety identification region comprises an identification marker composed of at least one single nucleotide polymorphism (SNP) that differs among hop varieties;
(ii) identifying the genotype of the single nucleotide polymorphism in each of the DNA fragments amplified at step (i);
(iii) comparing the genotype of the single nucleotide polymorphism in the variety identification region in each of the DNAs from the hops to be tested, as identified at step (ii), with the genotype of a single nucleotide polymorphism in a corresponding region in a DNA from a known hop variety, to thereby analyze whether the hop varieties to be tested and the known hop variety are concordant or discordant for the genotype of the single nucleotide polymorphism in the region in question; and
(iv) identifying the varieties of the hops to be tested, on the basis of the analysis results obtained at step (iii).
(2) The method as set forth in (1), wherein step (ii) is performed by identifying the nucleotide sequence of the variety identification region in each of the DNA fragments amplified at step (i); and
wherein step (iii) is performed by comparing the nucleotide sequence of the variety identification region in each of the DNAs from the hops to be tested, as identified at step (ii), with the nucleotide sequence of a corresponding region in a DNA from a known hop variety, to thereby analyze whether the hop varieties to be tested and the known hop variety are concordant or discordant for an identification marker in the region in question.
(3) The method as set forth in (1), wherein step (ii) is a step at which the genotype of the single nucleotide polymorphism in each of the DNA fragments amplified at step (i) is identified by contacting each of said DNA fragments with probes and/or primers for use in detecting the single nucleotide polymorphism that differs among hop varieties.
(4) The method as set forth in any one of (1) to (3), wherein the variety identification region comprises an identification marker prepared by a method comprising the steps of:
(a) performing transcriptome analysis using two or more different varieties of hops;
(b) performing assembling for each of the varieties on the basis of the nucleotide sequences of DNA fragments obtained as the result of step (a);
(c) searching for a single nucleotide polymorphism (SNP) that differs among the varieties by making comparison among the varieties in terms of the contigs and/or singlets obtained as the result of step (b);
(d) selecting a region comprising the SNP detected as the result of the SNP search at step (c) and designing primers for use in amplifying said region;
(e) determining an identification region and primers capable of amplifying the identification region by confirming that the region selected at step (d) can be amplified using the primers designed at step (d), with each of DNAs extracted from hops being used as a template, and by determining the nucleotide sequence of said region;
(f) determining the nucleotide sequence of the identification region by amplifying the identification region using the primers determined at step (e), with each of the DNAs extracted from the hops of the varieties to be identified being used as a template; and
(g) determining an identification marker composed of a combination of SNPs, which is required for identification of the varieties to be identified, by making comparison among the varieties in terms of the nucleotide sequence of the identification region determined at step (f).
(5) The method as set forth in any one of (1) to (3), wherein the variety identification region is a region that is composed of part or all of at least one nucleotide sequence selected from the group consisting of SEQ ID NOs: 9, 10, 11, 12, 13, 14 and 15 and which comprises at least one of the single nucleotide polymorphisms or insertion-deletion portions identified in FIGS. 1, 2, 3, 4 and 6.

(6) The method as set forth in any one of (1) to (3), wherein the variety identification region is at least one region selected from the group consisting of a region comprising the nucleotide sequence of SEQ ID NO: 9, a region comprising the nucleotide sequence of SEQ ID NO: 10, a region comprising the nucleotide sequence of SEQ ID NO: 11, a region comprising the nucleotide sequence of SEQ ID NO: 12, a region comprising the nucleotide sequence of SEQ ID NO: 13, a region comprising the nucleotide sequence of SEQ ID NO: 14, and a region comprising the nucleotide sequence of SEQ ID NO: 15.

(7) The method as set forth in any one of (1) to (3), wherein the variety identification region is composed of not only three regions consisting of a region comprising the nucleotide sequence of SEQ ID NO: 9, a region comprising the nucleotide sequence of SEQ ID NO: 10, and a region comprising the nucleotide sequence of SEQ ID NO: 11, but also a region that is composed of part or all of the nucleotide sequence(s) of SEQ ID NO: 12 and/or SEQ ID NO: 14 and which comprises at least one of the single nucleotide sequences or insertion-deletion portions identified in FIG. 4.

(8) The method as set forth in any one of (1) to (3), wherein step (i) is performed by PCR using a primer set selected from the group consisting of a combination of SEQ ID NOs: 1 and 2, a combination of SEQ ID NOs: 3 and 4, a combination of SEQ ID NOs: 5 and 6, and a combination of SEQ ID NOs: 7 and 8.

(9) The method as set forth in any one of (1) to (3), wherein step (i) is performed by PCR using not only three primer sets consisting of a combination of SEQ ID NOs: 1 and 2, a combination of SEQ ID NOs: 3 and 4, and a combination of SEQ ID NOs: 5 and 6, but also a primer set consisting of a combination of SEQ ID NOs: 7 and 8.

(10) A method for preparing an identification marker composed of a combination of single nucleotide polymorphisms that differ among hop varieties, the method comprising the steps of:
(a) performing transcriptome analysis using two or more different varieties of hops;
(b) performing assembling for each of the varieties on the basis of the nucleotide sequences of DNA fragments obtained as the result of step (a);
(c) searching for a single nucleotide polymorphism (SNP) that differs among the varieties by making comparison among the varieties in terms of the contigs and/or singlets obtained as the result of step (b);
(d) selecting a region comprising the SNP detected as the result of the SNP search at step (c) and designing primers for use in amplifying the region;
(e) determining an identification region and primers capable of amplifying the identification region by confirming that the region selected at step (d) can be amplified using the primers designed at step (d), with each of DNAs extracted from hops being used as a template, and by determining the nucleotide sequence of said region;
(f) determining the nucleotide sequence of the identification region by amplifying the identification region using the primers determined at step (e), with each of the DNAs extracted from the hops of the varieties to be identified being used as a template; and
(g) determining an identification marker composed of a combination of SNPs, which is required for identification of the varieties to be identified, by making comparison among the varieties in terms of the nucleotide sequence of the identification region determined at step (f).

(11) A nucleic acid comprising at least part of an identification marker prepared by the method as set forth in (10).

(12) A nucleic acid comprising a hop variety identification region and further comprising a region that is composed of part or all of at least one nucleotide sequence selected from the group consisting of SEQ ID NOs: 9, 10, 11, 12, 13, 14 and 15 and which comprises at least one of the single nucleotide polymorphisms or insertion-deletion portions identified in FIGS. 1, 2, 3, 4 and 6.

(13) Primers designed to be capable of amplifying the nucleic acid as set forth in (11) or (12).

(14) Primers composed of the nucleotide sequences of any of SEQ ID NOs: 1-8, wherein the primers are intended for use in identification of hop varieties.

(15) Probes for use in detecting a single nucleotide polymorphism that differs among hop varieties, in a variety identification region identified by the method as set forth in (10).

(16) Probes which are capable of detecting at least one of the single nucleotide polymorphisms or insertion-deletion portions located at the positions identified in FIG. 1, 2, 3, 4 or 6, in at least one nucleotide sequence selected from the group consisting of SEQ ID NOs: 9, 10, 11, 12, 13, 14 and 15, thereby enabling detection of a single nucleotide polymorphism that differs among hop varieties.

(17) A method for detecting mixing of a different hop variety in a hop sample, the method comprising the steps of:
(i) amplifying a fragment of a DNA extracted from a hop sample to be tested, the fragment which comprises a variety identification region, wherein the variety identification region comprises an identification marker composed of at least one single nucleotide polymorphism (SNP) that differs among hop varieties;
(ii) analyzing the nucleotide sequence of the variety identification region in the DNA fragment amplified at step (i) to obtain sequence data;
(iii) comparing the information on a single nucleotide polymorphic site constituting the identification marker, which is contained in the sequence data obtained at step (ii), with the information on a corresponding single nucleotide polymorphic site in a normal hop; and
(iv) determining the presence or absence of mixing of a different hop variety in the hop sample, wherein, in the case where the information on the single nucleotide polymorphic site in the sequence data obtained at step (ii) is concordant with the information on the corresponding single nucleotide polymorphic site in the normal hop, it is determined that no different hop variety is mixed, or in the case where the information on the single nucleotide polymorphic site in the sequence data obtained at step (ii) is discordant with the information on the corresponding single nucleotide polymorphic site in the normal hop, it is determined that a different hop variety is mixed.

(18) The method as set forth in (17), further comprising, subsequently to step (iv), the steps of:
(v) identifying a nucleotide different from that of the normal hop on the basis of an information derived from a hop other than the normal one, which appears in the single nucleotide polymorphic site in the sequence data obtained at step (ii), in the case where it is determined at step (iv) that the information on the single nucleotide polymorphic site in the sequence data obtained at step (ii) is discordant with the information on the corresponding single nucleotide polymorphic site in the normal hop; and (vi) checking the nucleotide different from that of the normal hop, which is identified in the single nucleotide polymorphic site at step (v), against the identification marker to deduce or identify the variety of the hop mixed.

(19) The method as set forth in (17), further comprising, subsequently to step (iv), the steps of:

(v) identifying a nucleotide different from that of the normal hop, and determining the mixing proportion thereof, on the basis of an information derived from a hop other than the normal one, which appears in the single nucleotide polymorphic site in the sequence data obtained at step (ii), in the case where it is determined at step (iv) that the information on the single nucleotide polymorphic site in the sequence data obtained at step (ii) is discordant with the information on the corresponding single nucleotide polymorphic site in the normal hop; and (vi) checking the nucleotide different from that of the normal hop, which is identified in the single nucleotide polymorphic site at step (v), against the identification marker to deduce or identify the variety of the hop mixed and the proportion of the hop variety mixed.

(20) The method as set forth in any one of (1) to (9), wherein step (iii) comprises analyzing the presence or absence of an insertion sequence of 19-25 nucleotides.

Advantageous Effects of the Invention

By virtue of the fact that it has become possible to identify the varieties of hops using an identification marker composed of a single nucleotide polymorphism among varieties, when it is determined whether a hop delivered as a raw material is of the same variety as the ordered one or whether a different variety of hop is mixed, the varieties of hops to be tested can be identified accurately, and the presence or absence of mixing of a different variety can be detected. Further, if a different variety of hop is mixed, not only the presence or absence of the mixing but also the variety of the hop mixed can be deduced or identified, and the proportion of the hop variety mixed can be analyzed.

Also, primers and/or probes for use in identifying varieties of interest can be designed using the information on a nucleotide constituting an identification marker prepared by the method of the present invention, and it can be expected that analysis by realtime PCR and a next-generation sequencer through the use of said primers and/or probes will make it possible to quantitatively analyze the mixing proportion of a different variety.

Thus, a high-quality beer of interest can be supplied stably. Also, even if hops to be tested are deteriorated or damaged, the varieties of the hops can be identified.

BRIEF DESCRIPTIONS OF DRAWINGS

FIG. 1 depicts a drawing showing the results of analysis of 14 varieties of hops for SNPs in region A1, as well as a nucleotide code table. The SNP positions represent the positions of SNPs as counted from the 5' end of the consensus sequence in region A1 (SEQ ID NO: 9). The number of the SNPs analyzed totaled 24. The 14 varieties of hops subjected to the analysis were classified into 9 diplotypes.

FIG. 2 depicts a drawing showing the results of analysis of 14 varieties of hops for SNPs in region B1. The SNP positions represent the positions of SNPs as counted from the 5' end of the consensus sequence in region B1 (SEQ ID NO: 10). The number of the SNPs analyzed totaled 10. The 14 varieties of hops subjected to the analysis were classified into 7 diplotypes. As for the notations for the nucleotides other than A, G, C and T, reference should be made to the code table given in FIG. 1.

FIG. 3 depicts a drawing showing the results of analysis of 14 varieties of hops for SNPs in region C1. The SNP positions represent the positions of SNPs as counted from the 5' end of the consensus sequence in region C1 (SEQ ID NO: 11). The number of the SNPs analyzed totaled 29, and among these SNPs, positions 129-134 in SEQ ID NO: 11 constitute an insertion-deletion (indel) portion. The 14 varieties of hops subjected to the analysis were classified into 3 diplotypes. As for the notations for the nucleotides other than A, G, C and T, reference should be made to the code table given in FIG. 1.

FIG. 4 depicts a drawing showing the results of the analysis of Perle and Northern Brewer for SNPs in regions A1-2-L and A1-2-R. The SNP positions represent the positions of the SNPs as counted from the 5' end of each of the consensus sequences between the two varieties in regions A1-2-L and A1-2-R (SEQ ID NOs: 12 and 14). The number of the SNPs analyzed in region A1-2-L totaled 21, and among these SNPs, positions 186-194 and position 399 in SEQ ID NO: 12 each constitute an indel portion. The number of the SNPs analyzed in region A1-2-R totaled 67, and among these SNPs, positions 57-59 and position 65 in SEQ ID NO: 14 each constitute an indel portion. Perle and Northern Brewer showed different diplotypes.

FIG. 5 depicts a table summarizing the varieties of the hops subjected to variety identification and the diplotypes of the identification markers used for these hops.

FIG. 6 depicts a drawing showing the results of analysis of Sladeck (Sládek), Spalter, Perle, Tettnang and Northern Brewer for SNPs in regions A1-2-L and A1-2-R. The SNP positions represent the positions of the SNPs as counted from the 5' end of each of the consensus sequences between these five varieties in regions A1-2-L and A1-2-R (SEQ ID NOs: 13 and 15). The number of the SNPs analyzed in region A1-2-L totaled 23, and among these SNPs, position 12, positions 183-191, and position 396 in SEQ ID NO: 13 each constitute an indel portion. The number of the SNPs analyzed in region A1-2-R totaled 28, and among these SNPs, position 437 in SEQ ID NO: 15 constitutes an indel portion. The five varieties of hops subjected to the analysis each showed a different diplotype in region A1-2-L, while they were classified into 4 diplotypes in region A1-2-R.

FIG. 7 depicts a table summarizing the diplotypes of the identification markers in region A1-2-L (SEQ ID NO: 13) which were used for Sladeck (Sládek), Spalter, Perle, Tettnang, and Northern Brewer.

MODES FOR CARRYING OUT THE INVENTION

Figure 8:
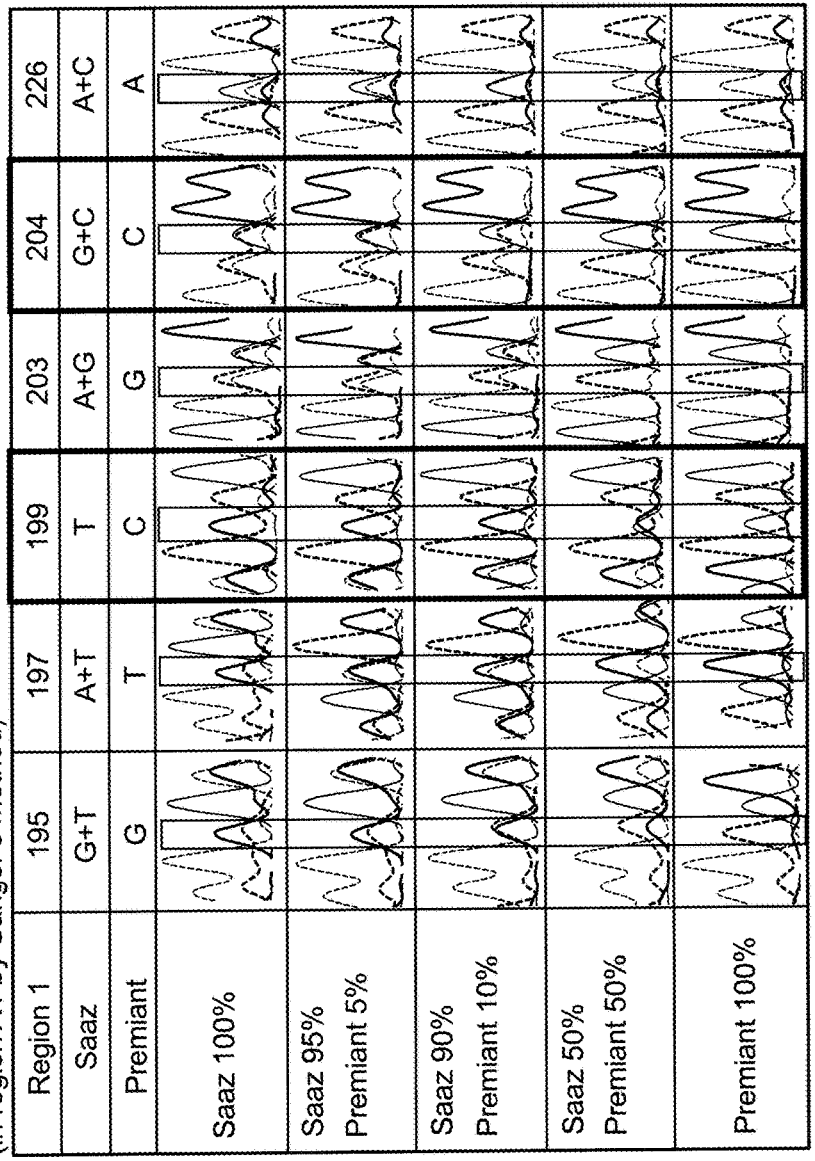
FIG. 8 depicts electropherograms showing the results of analysis of different mixed samples of Saaz and Premiant for the nucleotide sequence of region A1. The nucleotide numbers in region A1 are equivalent to those in SEQ ID NO: 9.

Hereunder, the present invention will be specifically described, but is not limited to the following specific descriptions. This invention relates to a method for identifying the varieties of hops using an identification marker composed of at least one single nucleotide polymorphism (SNP) that differs among varieties; a method for preparing said identification marker; a method for detecting mixing of a different hop variety in a hop sample using said identification marker; said identification marker; variety identification primers designed to be capable of amplifying a region having said identification marker; and variety identification probes for use in detecting said identification marker.

<Summary of the Present Invention>

The present application relates to an invention characterized in that the varieties of hops are identified using an identification marker composed of at least one SNP that differs among varieties. To be specific, DNA is extracted from a hop to be tested, and it is analyzed whether a nucleotide(s) in a site corresponding to an identification marker composed of a SNP, which is contained in a nucleotide sequence corresponding to the nucleotide sequence of a region having the identification marker, is concordant with a nucleotide(s) in the identification marker; then, if this is the case, the variety of the hop to be tested is identified to be the same as the variety of the identification marker.

<Definitions>

Unless otherwise defined herein, the scientific and technical terms used in relation to the present invention shall have the same meanings as generally appreciated by those skilled in the art.

As referred to herein, the "identification marker" refers to an indicator for use in identifying hop varieties, which is composed of at least one single nucleotide polymorphism that differs among varieties. The identification marker of the present invention is determined so as to ensure that no overlap exists among varieties to be identified, and that each of the varieties and the identification marker correspond to each other on a one-to-one basis. However, a single nucleotide polymorphism constituting the identification marker may also be varied depending on the varieties of hops to be identified and the number of the varieties. For example, in a case where two varieties alone are to be identified, it is sufficient to use an identification marker composed of one single nucleotide polymorphism, or in a case where many varieties are to be identified, an identification marker is determined so as to ensure that no overlap is produced when two or more single nucleotide polymorphisms (or, in some cases, two or more single nucleotide polymorphisms in two or more identification regions) are combined. The identification marker is basically determined such that no overlap exists, but depending on the purpose of the identification, two or more varieties that overlap in identification marker (i.e., two or more varieties sharing the same identification marker) may also be regarded as one group and used in correspondence to one identification marker.

As referred to herein, the "identification region" refers to a region of a hop-derived DNA, which comprises an identification marker. The identification region is not limited to one region and may be composed of two or more regions. Also, the identification region of a nucleic acid that amplifies a DNA fragment of a hop to be tested in the process of variety identification may in particular be described as a "variety identification region." The variety identification region may be the same as the identification region, or may be set separately depending on the purpose of the variety identification. The variety identification region is not limited to one region and may be composed of two or more regions.

<Method for Preparing an Identification Marker>

The present application provides a method for preparing an identification marker for use in identifying the varieties of hops.

In one mode, the identification marker of the present invention is prepared by a method as mentioned below. First, transcriptome analysis is performed using two or more different varieties of hops, and a region having a relatively large number of single nucleotide polymorphisms (SNPs) is selected; then, primers are designed, and an identification region as well as primers capable of amplifying said region are determined. Next, DNAs are extracted from varieties to be identified, the identification region is amplified using the primers to determine the nucleotide sequence of said region, and then comparison is made between the varieties, whereby there is determined an identification marker composed of at least one SNP, which is required for identification of the varieties to be identified.

To be specific, the method for preparing an identification marker for use in identifying the varieties of hops may comprise the steps of:

(a) performing transcriptome analysis using two or more different varieties of hops;

(b) performing assembling for each of the varieties on the basis of the nucleotide sequences of DNA fragments obtained as the result of step (a);

(c) searching for a single nucleotide polymorphism (SNP) that differs among the varieties by making comparison among the varieties in terms of the contigs and/or singlets obtained as the result of step (b);

(d) selecting a region comprising the SNP detected as the result of the SNP search at step (c) and designing primers for use in amplifying the region;

(e) determining an identification region and primers capable of amplifying the identification region by confirming that the region selected at step (d) can be amplified using the primers designed at step (d), with each of DNAs extracted from hops being used as a template, and by determining the nucleotide sequence of said region;

(f) determining the nucleotide sequence of the identification region by amplifying the identification region using the primers determined at step (e), with each of the DNAs extracted from the hops of the varieties to be identified being used as a template; and (g) determining an identification marker composed of a combination of SNPs, which is required for identification of the varieties to be identified, by making comparison among the varieties in terms of the nucleotide sequence of the identification region determined at step (f). However, the present invention is not limited to the above-mentioned methods, and any other generally known method, modified as appropriate, may also be used.

Steps (a) to (g) mentioned above are described as below.

(a) Performing Transcriptome Analysis Using Hops

In order to search for a candidate(s) for a SNP(s) to be included in an identification marker, two or more different varieties of hops were first respectively subjected to transcriptome analysis.

The term "transcriptome" refers to the totality of all mRNAs (or primary transcripts) present in a tissue or cell at a particular state.

The following describes an exemplary procedure for performing transcriptome analysis according to the present invention, but this is not the sole particular example. First, from each of the tissues of different varieties of hops, total RNA is crudely extracted. Total mRNA (poly(A)$^+$ RNA) is purified from the total RNA, and cDNAs are synthesized using the purified mRNA as a template. The resulting cDNA library consists of a mixture of cDNAs expressed in a large amount and cDNAs expressed in a small amount, and thus the library is subjected to correction (equalization) for variations in expression amount as well as size-based purification. Next, sequence analysis is performed on the cDNAs using an ultrafast DNA nucleotide sequence analyzer.

As the tissues of hops from which total RNA is extracted, various tissues constituting buds, leaves, stems, and cones of hops are advantageously used, but these are not the sole particular examples. Also, in the case of collecting such tissues from a hop strain, the cultivation method, growth stage and the like of the hop strain are not particularly limited. The hop tissue may be fresh or dried, or may be processed into pellets, for example. However, since RNA is easily degraded, it is preferred to use a fresh tissue collected from a hop strain as soon as possible, or to use young hop leaves as an RNA-rich tissue. Also, in the process of collecting a sample for analysis, it is preferred to take measures for preventing the degradation of RNA as much as possible, or to work toward preventing contamination.

It is sufficient if two or more different varieties of hops are used in transcriptome analysis, and the varieties of hops to be used and the number of the varieties can be selected depending on the purpose. In order to detect a larger amount of SNPs, it is preferred to use three or more different varieties of hops. Also, it is preferred to use hop varieties selected from varieties to be identified.

Each of the substeps for transcriptome analysis, ranging from extraction of total RNA from a hop tissue to sequence analysis of cDNAs, can be performed by employing a generally accepted technique.

(b) Performing Assembling for Each Variety

On the basis of the nucleotide sequences of the DNA fragments (cDNAs), which are thus identified through transcriptome analysis for each of the varieties, sequence assembling is performed for each variety. The sequence assembling refers to reconstruction of an original long nucleotide sequence from short DNA fragments. For example, on the basis of the nucleotide sequences of the DNA fragments obtained as the result of step (a), the DNA fragments are clustered according to whether or not they share a mutually overlapping nucleotide sequence, and a series of clustered DNA fragments are subjected to detection of their overlapping portions and are connected (assembled) with each other into one sequence. Such sequences thus assembled are collectively referred to as "contigs", and single reads which are not involved in contig reconstruction are collectively referred to as "singlets". Reconstruction of contigs by sequence assembling can be achieved by a generally accepted technique.

(c) Detecting a Difference in Nucleotides Corresponding Among Varieties

On the basis of the nucleotide sequences of the DNA fragments, which are thus identified through transcriptome analysis for each of the varieties, the DNA fragments are assembled by their mutually overlapping sequence portions to form contigs. With the use of the thus-obtained contig sequences and/or singlet sequences, a difference in nucleotides corresponding among the varieties (i.e., SNP in this instance) is detected.

In order to detect a difference in nucleotides corresponding among two or more different varieties of hops, one of the varieties is first selected as a reference sequence (reference). Next, the contigs and/or singlets (preferably contigs, more preferably contigs and singlets) of the selected variety are designated as reference sequences, and on the basis of these reference sequences, single reads of each of the other varieties are mapped according to whether or not they share a common portion. Further, contigs constituted by the mapped single reads are identified from the assembling information deployed on an analysis software. The reference sequences as well as the contigs and/or singlets of the other varieties, as thus obtained, are aligned to detect a SNP. Since it is likely that any SNP may get missed in the case of using only one variety as a reference, it is preferred that, with each of the other varieties being selected as a reference, mapping and alignment be done in the same way as described above to detect a SNP, and the results of these detections be summarized to obtain SNP data. Repeating SNP detection with each of different varieties being selected as a reference makes it possible to detect a larger number of SNPs and to thereby select a SNP(s) that is(are) more eligible as an identification marker. In a case where a difference in nucleotides corresponding among three or more varieties is detected according to the present invention, any difference in nucleotides corresponding among at least any two of the varieties is regarded as a SNP. Detection of a difference in nucleotides corresponding among varieties can be made by a generally accepted technique. The above-described procedure is merely an example and is not the sole one. Another possible procedure for detecting such a difference is to perform BLAST searching using the contig sequences of one variety.

(d) Selecting a Region Comprising a SNP and Designing Primers

On the basis of the results thus obtained by SNP detection using contig sequences and/or singlet sequences, a region having a SNP(s) usable for identification is selected. For the purpose of identifying many varieties, it is desirable to select a region having a large number of SNPs. As more specific examples possible, a region having a SNP(s) in a homozygote (which has identical nucleotide sequences between double strands in a diploid chromosome) may be selected with preference for convenience of analysis, or a region having more SNPs per contig may be selected, but these are not the sole particular examples.

Next, primers capable of amplifying such a region are designed. The primers can be designed by a generally accepted technique.

(e) Determining an Identification Region and Primers Capable of Amplifying the Identification Region Since the primers designed in such a way as described above are based on the contig or single sequences formed from a cDNA library, it is uncertain whether they can successfully amplify a genomic DNA containing promoter regions and introns. Hence, it is necessary to confirm amplification using a genomic DNA extracted from a hop. Even if the primers succeed in amplification, confirmation of its nucleotide sequence by the Sanger's method or the like is required to determine the presence or absence of any insertion-deletion (indel) or microsatellite, or to confirm the presence of an intended SNP(s). Therefore, a region comprising a SNP(s) is amplified and sequenced using the primers designed at step (d), with each of genomic DNAs extracted from pellets, dried cones, or the like of hop varieties (preferably the hop varieties used at step (a)) being used as a template. Thereby, it is confirmed that the region can be amplified at an appropriate size, and it is also confirmed, in comparison with the nucleotide sequences determined based on transcriptome analysis as described above, that the region is applicable to variety identification; thereupon, a region usable for identification (identification region) and primers capable of amplifying said region are determined. In a case where the region cannot be amplified due to the presence of introns or any other reason, or where there is any disadvantage or problem in amplification size or nucleotide sequence, the selected region is reviewed or primers are designed again.

The identification region to be determined for making an identification marker is not limited to one region, and two or more regions can also be selected as such. Selecting two or more regions makes it possible to identify a larger number of hop varieties.

The identification region may contain an insertion-deletion (indel) portion. In a broad sense, the term "single nucleotide polymorphism (SNP)" encompasses insertion-deletion (indel); thus, in the present invention, an insertion-deletion (indel) portion can also be used as a SNP constituting an identification marker.

(f) Determining the Nucleotide Sequence of an Identification Region, and (g) Determining an Identification Marker for Varieties to be Identified With the use of the primers capable of amplifying the identification region, which are determined at step (e), the identification region is amplified for each of the varieties to be identified, with each of genomic DNAs extracted from said varieties being used as a template.

As referred to herein, the varieties to be identified refers to the varieties of hops selected as objects to be identified, and are composed of two or more different varieties. The varieties of hops are not particularly limited as long as they are plants classified under the scientific name of Humulus lupulus. Examples include hops native mainly to Germany, the U.S., Czech, the U.K., France, China, Slovenia, South Africa, Australia, New Zealand, and Japan.

Exemplary varieties of hops native to Europe include, but are not limited to, Saaz, Sladeck (Sládek), Premiant, Tradition, Spalter, Spalter Select, Perle, Tettnang, Brewer's Gold, Northern Brewer, Magnum, Herkules, German Nugget, Taurus, Admiral, Aurora, Hersbrucker, Hallertau Merkur, Hallertau Mittelfrueh, and Target.

Exemplary varieties of hops native to the U.S. include, but are not limited to, Amarillo, Cascade, Centennial, Chinook, Cluster, Columbus, Crystal, Fuggle, Galena, Golding, Horizon, Liberty, Mount Hood, Nugget, Santiam, Sterling, Summit, Super Galena, Tettnanger, Tomahawk, Ultra, Willamette, and Zeus.

The varieties of hops to be identified and the number of the varieties can be set freely depending on the purpose of identification. For example, the varieties of hops cultivated in a neighborhood may be selected—the varieties to be identified can be selected depending on the purpose of the occasion.

In one mode, the varieties to be identified are 14 varieties of hops native to Germany and Czech as listed in Table 4 given in Example 1.

For each of the varieties to be identified which are thus selected depending on the purpose, amplified DNA fragments are sequenced and determined for nucleotide sequence.

For each of the varieties to be identified, as determined at step (f), the nucleotide sequence of the identification region is aligned to extract a SNP portion(s). The identification marker is determined by combining extracted SNPs so as to ensure that no overlap exists among the varieties to be identified, and that each of the varieties and the identification marker correspond to each other on a one-to-one basis.

Here, steps (f) and (g) may also be performed by following the steps described below in (1) to (11).

(1) Obtaining Hops

The "DNA" as used in the present invention can be obtained by extraction from a hop tissue. As the hop tissue, various tissues constituting buds, leaves, stems, and cones of hops are advantageously used, but these are not the sole particular examples. Also, in the case of collecting the tissue from a hop strain, the cultivation method, growth stage and the like of the hop strain are not particularly limited. The hop tissue may be fresh or dried, or may be processed into pellets, for example.

(2) Extracting DNAs

DNA extraction can be conducted by using a technique known to those skilled in the art, such as the CTAB (cetyltrimethyl ammonium bromide) method or any other method using a commercially available kit like Qiagen DNeasy Tissue Kit (Qiagen) or ISOPLANT II (Nippon Gene). The CTAB method is preferred from the viewpoints of usability and cost effectiveness.

(3) Amplifying DNA Fragments

The DNAs thus extracted are amplified by a PCR method. The PCR method to be used in the present invention is not particularly limited, and examples include known PCR methods and various modified PCR methods. One exemplary method is disclosed below.

There are provided a set of primers and a template DNA, as well as a PCR reaction solution prepared by mixing various reagents including Tris-HCl, KCl, $MgCl_2$, dNTPs, and a Taq DNA polymerase. One cycle of PCR consists of the following three steps: heat denaturation, annealing, and DNA strand extension (synthesis) reaction catalyzed by a DNA polymerase. These steps require different, or sometimes identical, reaction temperatures and times, and these reaction temperatures and times are selected as appropriate depending on the nucleotide sequences, lengths or the like of DNA regions to be amplified. These steps can be performed using a commercially available thermal cycler.

The primers to be used in the present invention are a pair of primers capable of amplifying the identification region determined at step (e). Examples of the primer set that can be used include those determined by the present inventors, i.e., the primer set A1-3L/A1-3R (SEQ ID NOs: 1 and 2), the primer set B1-1L/B1-1R (SEQ ID NOs: 3 and 4), the primer set C1-1L/C1-1R (SEQ ID NOs: 5 and 6), and/or the primer set A1-2-1L/A1-2-1R (SEQ ID NOs: 7 and 8).

(4) Confirming Amplification by PCR

In order to evaluate the PCR results (PCR products), any given technique that allows identification of a particular DNA fragment is used, such as electrophoresis, gel filtration, and hybridization, whereby it is confirmed that a DNA fragment of an intended size is amplified. For example, in the cases of using the primer sets A1-3L/A1-3R (SEQ ID NOs: 1 and 2), B1-1L/B1-1R (SEQ ID NOs: 3 and 4), C1-1L/C1-1R (SEQ ID NOs: 5 and 6), and A1-2-1L/A1-2-1R (SEQ ID NOs: 7 and 8), the amplifications of the DNA fragments of lengths of 651, 729, 646 and ca. 1500 bases, respectively, are confirmed.

(5) Purifying PCR Products

With a view to using the amplified PCR products as templates for cycle sequencing reaction, the PCR products are separated from various components used in the PCR, including surplus primers. This purification can be performed, for example, using the commercial QIAquick PCR Purification Kit (Qiagen) and following the protocol attached thereto.

(6) Cycle Sequencing Reaction and Purifying Sequencing Products

In order to sequence the thus-purified PCR products, cycle sequencing reaction is performed using said products as templates. The procedure for this reaction is similar to that of the PCR method, and involves repetition of three steps (heat denaturation, annealing, and DNA strand extension reaction catalyzed by a DNA polymerase) using a thermal cycler, but is characterized in that different lengths of single-stranded DNAs are synthesized using either one of the primers in the presence of terminators labeled with four different fluorescent dyes varied for each base. The cycle sequencing procedure may be performed, for example, using the commercial BigDye Terminator v1.1 Cycle Sequencing Kit (Life Technologies). To be specific, this procedure can be performed according to the Japanese-version protocol for said kit (e.g., "Cycle Sequencing of Single- and Double-Stranded DNA" on page 22, "Cycle Sequencing on the GeneAmp PCR System 9700, 9600, 2700, or 2400" on page 25, and "Spin Column (Spin Plate) Purification" on pages 38-40). Additionally, the nucleotide sequences of the primers to be used in cycle sequencing can be the same as those of the primers used in the PCR amplification of the DNA fragments of interest. More specifically, to each of the purified PCR product solutions, which have been optionally diluted with sterile distilled water, specified substances are added to thereby prepare a cycle sequencing reaction solution. The prepared solution is put in PCR microtubes, and the tubes are placed in a PCR system. After preliminary denaturation (e.g., at 96° C. for 1 min) is performed, the reaction cycle of denaturation (e.g., at 96° C. for 10 sec), annealing (e.g., at 50° C. for 5 sec), and strand extension (e.g., at 60° C. for 4 min) is repeated, for example, 25 times. If samples cannot be taken out immediately after completion of the reaction, they may be retained while the temperature of the sample block is lowered.

Thereafter, sequencing products, i.e., single-stranded DNA mixtures, are purified from the thus-obtained reaction solutions to prepare samples to be subsequently sequenced with a sequencer. This purification is conducted, for example, by a procedure using the CENTRISEP Spin Column (Life Technologies), in which the column is used according to the attached protocol to prepare samples of interest.

(7) Sequencing DNA Fragments

The sequencing products thus obtained by the dye terminator method are sequenced. A common procedure for this sequencing is electrophoresis, and one example is a procedure in which sequencing products are subjected to electrophoresis using the ABI PRISM 310 Genetic Analyzer and successively determined for their nucleotide sequences by a laser fluorescence detector through the utilization of the fact that the fluorescent substances used for labeling are varied for each base.

(8) Analyzing Nucleotide Sequences

The determined nucleotide sequences are analyzed to obtain sequence data. The sequence data obtained for the respective products are checked against each other to determine exact nucleotide sequences.

(9) Aligning Nucleotide Sequences

The thus-obtained sequence data for varieties to be identified are aligned.

(10) Excluding Nucleotides Conserved in the Nucleotide Sequences of all Varieties to be Identified After the alignment is done, these sites composed of one or more nucleotides, which are conserved in the nucleotide sequences of all the varieties to be identified, are excluded from said sequences. Excluding the nucleotide sites conserved in all of the nucleotide sequences in such a way makes it possible to clearly detect the presence of a single nucleotide polymorphism(s) and also to easily determine an identification marker based on the single nucleotide polymorphism(s) at a subsequent step.

To be specific, such sites with a nucleotide(s) conserved in the nucleotide sequences of all the varieties to be identified are extracted from the data obtained by the alignment. The term "nucleotide(s) conserved" refers to a nucleotide(s) whose column in the resulting alignment data is identical among the nucleotide sequences of all the varieties to be identified. The extracted sites are all excluded. The reason why the conserved sites are all excluded is explained below.

In a case where the nucleotide sequences of hop varieties are compared, it is assumed that most nucleotides are present in common in all varieties to be identified. However, the present invention is characterized by focusing on single nucleotide polymorphisms remaining after those common portions shared by all the varieties to be identified are excluded and by preparing an identification marker based on the correlation which said single nucleotide polymorphisms have with varieties. This is why the conserved sites are all excluded.

The extraction can be performed using any method such as visual inspection or mechanical manipulation as long as the method enables extraction of those nucleotides conserved in the nucleotide sequences of all the varieties to be identified.

(11) Determining an Identification Marker

On the basis of the SNP(s) remaining after the exclusion described above, an identification marker is determined. As described above, the identification marker of the present invention is determined so as to ensure that no overlap exists among varieties to be identified, and that each of the varieties and the identification marker correspond to each other on a one-to-one basis. In the process of determining the inventive identification marker, a SNP(s) constituting the identification marker is(are) determined every time depending on the purpose of use, namely depending on the varieties of hops to be identified and the number of said varieties. For example, in a case where two particular varieties alone are to be identified, one SNP that enables identification of these two varieties can be selected and used as an identification marker. In a case where many varieties are to be identified, an identification marker can be determined so as to ensure that no overlap is produced between said varieties when two or more SNPs (or, in some cases, two or more SNPs in two or more identification regions) are combined.

For example, in a case where 14 varieties of hops as listed below in Table 4 given in Example 1 are to be identified, these 14 varieties can be classified into 9 types based on 24 SNPs present in region A1 (SEQ ID NO: 9), classified into 7 types based on 10 SNPs present in region B1 (SEQ ID NO: 10), and classified into 3 types based on 29 SNPs present in region C1 (SEQ ID NO: 11) (6 of these 29 SNPs corresponding to nucleotide positions 129-134 in SEQ ID NO: 11 constitute an insertion-deletion portion); and further these 14 varieties can be classified into 13 types based on a combination of the SNPs present in these three regions. In other words, as to 12 of the 14 varieties, an identification marker and each variety can be made to correspond to each other on a one-to-one basis, based on the SNPs alone present in regions A1, B1 and C1. Furthermore, since one other remaining type consists of two similar varieties, any of 21 SNPs present in region A1-2-L (SEQ ID NO: 12) (10 of these 21 SNPs constitute an insertion-deletion portion) and 67 SNPs present in region A1-2-R (SEQ ID NO: 14) (4 of these 67 SNPs constitute an insertion-deletion portion) is selected as an additional region that enables identification of these two similar varieties, whereby an identification marker and each of these two varieties can be made to correspond to each other. As such, in the case of identifying the 14 varieties mentioned above, a total of 64 SNPs, which consist of 24 SNPs in region A1, 10 SNPs in region B1, and 29 SNPs in region C1 (6 of these 29 SNPs constitute an insertion-deletion portion), as well as any one of the SNPs present in regions A1-2-L and A1-2-R, can be determined as an identification marker. In another exemplary case, where some of the above-mentioned 14 varieties are selected as varieties to be identified, some of the above-mentioned 64

SNPs which are required for identification of said some varieties may be selected and determined as an identification marker.

In yet another exemplary case, where just the two similar varieties mentioned above are to be identified, any one of the SNPs present in regions A1-2-L and A1-2-R can be determined as an identification marker. In further another exemplary case, where among 14 varieties of hops as listed below in Table 4 given in Example 1, the following five varieties consisting of Sladeck (Sládek), Spalter, Perle, Tettnang, and Northern Brewer are to be identified, 23 SNPs present in region A1-2-L (SEQ ID NO: 13) (11 of these 23 SNPs constitute an insertion-deletion portion) can be determined as an identification marker.

The above description is given by means of examples in which some or all of 14 varieties of hops native to Germany and Czech as listed in Table 4 in Example 1 are to be identified. As for another mode in which much more varieties even including those native to the U.S. are to be identified, reference should be made to Example 5. As shown in Table 20, 22 nucleotides (nucleotides positions 64-85) surrounded by box are observed in Premiant and Summit, but this insertion sequence is absent in Zeus. Thus, the presence or absence of an insertion sequence can also serve as a factor for variety identification. The length of an insertion sequence is not particularly limited, and may be, for example, 19-25 nucleotides long. In addition, SNPs are observed even in the insertion sequence mentioned above (i.e., nucleotide positions 64, 67 and 75); thus, a SNP(s) present in an insertion sequence can also be selected as an identification marker. Another identification factor is exemplified by the length of the repeat sequence CA or TA, which follows the above-mentioned insertion sequence and extends up to nucleotide position 141. For example, the repeat sequence in Summit is longer by 12 nucleotides than the sequences of Premiant and Zeus.

As described above, in a case where 14 varieties of hops as listed in Table 4 are to be identified, these varieties can be classified into 7 types based on 10 SNPs present in region B1 (SEQ ID NO: 10). However, in a case where not only these varieties but also any variety native to the U.S. (e.g., Galena) is to be identified, nucleotide positions 245-248 also serve as SNPs and constitute an identification marker.

Furthermore, as also described above, in a case where 14 varieties of hops as listed in Table 4 are to be identified, these varieties can be classified into 3 types based on 29 SNPs present in region C1 (SEQ ID NO: 11). However, in a case where not only these varieties but also any variety native to the U.S. (e.g., Galena) is to be identified, nucleotide positions 76-80, 93, 136, 138, 163, 165, 245, 313, 321, 373, 376, 435 and 438 also serve as SNPs and constitute an identification marker.

In another mode, the identification marker of the present invention may also be prepared using a genomic DNA, a mitochondrial DNA, or a chloroplast DNA which are derived from two or more different varieties of hops, with preference given to using a genomic DNA derived from two or more different varieties of hops.

The method for preparing an identification marker for use in identifying the varieties of hops, using a genomic DNA, a mitochondrial DNA, or a chloroplast DNA may comprise the steps of:

(a-1) extracting a genomic DNA, a mitochondrial DNA, or a chloroplast DNA from a tissue of each of the two or more different varieties of hops;

(a-2) randomly cleaving DNAs obtained as the result of step (a-1) and screening for DNA fragments of an appropriate size;

(a-3) determining the nucleotide sequences of the DNA fragments obtained at step (a-2);

(b) performing assembling for each of the varieties on the basis of the nucleotide sequences of the DNA fragments determined as the result of step (a-3);

(c) searching for a single nucleotide polymorphism (SNP) that differs among the varieties by making comparison among the varieties in terms of the contigs and/or singlets obtained as the result of step (b);

(d) selecting an identification region comprising the SNP detected as the result of the SNP search at step (c) and designing primers for use in amplifying said region;

(f) determining the nucleotide sequence of the identification region by amplifying the identification region using the primers designed at step (d), with each of the DNAs extracted from the hops of the varieties to be identified being used as a template; and (g) determining an identification marker composed of a combination of SNPs, which is required for identification of the varieties to be identified, by making comparison among the varieties in terms of the nucleotide sequence of the identification region determined at step (f).

Steps (a-1) to (a-3) can be performed by techniques known to those skilled in the art. In particular, since DNA fragments are obtained in a large amount, it is preferred to use an ultrafast DNA nucleotide sequence analyzer in determining the nucleotide sequences of the DNA fragments.

Steps (b) to (d) and (f) to (g) can be performed by such techniques as described in the section regarding the transcriptome analysis-based method of the previously discussed mode.

According to the transcriptome analysis-based method, a SNP(s) is(are) searched for in cording regions or 5'- or 3'-untranslated regions based on mRNAs which do not contain an intron, whereas in this mode which uses a genomic DNA, a mitochondrial DNA, or a chloroplast DNA, a SNP(s) is searched for in all DNA regions including introns. For this reason, in the case of using a genomic DNA, a mitochondrial DNA, or a chloroplast DNA, it is possible to omit step (e) of the identification marker preparation method based on transcriptome analysis, at which it is confirmed that a SNP-containing region can be amplified using primers designed to amplify said region.

In the transcription analysis-based mode described above as well as in this mode using a genomic DNA (nuclear genome), a mitochondrial DNA, or a chloroplast DNA, an identification marker is prepared by a two-stage process in which a SNP(s) is(are) first searched for using two or more different varieties of hops, to thereby determine an identification region and primers, whereafter all varieties to be identified are compared in terms of the nucleotide sequence of the identification region to determine a SNP(s) suited as an identification marker. However, it is also acceptable that, while all varieties to be identified are used from the beginning, a SNP(s) is(are) searched for to determine an identification region and primers, whereafter comparison is made in terms of the nucleotide sequence of the identification region to determine a SNP(s) suited as an identification marker. Namely, in a case where all varieties to be identified are used from the beginning in any of the two modes described above, step (f) of determining the nucleotide sequence of an identification region for verities to be identified becomes unnecessary.

<Method for Identifying the Varieties of Hops>

The present invention also provides a method for identifying the varieties of hops. To be specific, the inventive method for identifying the varieties of hops may comprise the steps of:

(i) amplifying fragments of DNAs derived from hops to be tested, the fragments which each comprise a variety identification region, wherein the variety identification region comprises an identification marker composed of at least one single nucleotide polymorphism (SNP) that differs among hop varieties;

(ii) identifying the genotype of the single nucleotide polymorphism in each of the DNA fragments amplified at step (i);

(iii) comparing the genotype of the single nucleotide polymorphism in the variety identification region in each of the DNAs from the hops to be tested, as identified at step (ii), with the genotype of a single nucleotide polymorphism in a corresponding region in a DNA from a known hop variety, to thereby analyze whether the hop varieties to be tested and the known hop variety are concordant or discordant for the genotype of the single nucleotide polymorphism in the region in question; and (iv) identifying the varieties of the hops to be tested, on the basis of the analysis results obtained at step (iii).

The hops to be tested are not particularly limited as long as they are plants classified under the scientific name of *Humulus lupulus*. Examples include, but are not limited to, hops native to Europe and the U.S. as listed above in the section regarding the inventive method for preparing an identification marker.

In one mode, the hops to be tested are 14 varieties of hops as listed in Table 4 in Example 1.

Steps (i) to (iv) mentioned above are described below.

(i) Amplifying DNA Fragments Comprising a Variety Identification Region

The DNA fragments comprising a variety identification region are amplified using variety identification primers capable of amplifying a reference region having an identification marker, with each of genomic DNAs extracted from hops to be tested for variety identification being used as a template. Extraction of genomic DNAs and amplification of DNA fragments may be done, for example, according to or in line with the techniques described above in the headings of "(1) Obtaining hops" to "(3) Amplifying DNA fragments" in the subsection titled "(f) Determining the nucleotide sequence of an identification region, and (g) determining an identification marker for varieties to be identified" of the section titled "<Method for preparing an identification marker>".

The variety identification region is a region comprising an identification marker prepared by the identification marker preparation method described above. In a case where single nucleotide polymorphisms constituting an identification marker are present in two or more regions, the variety identification region may be composed of two or more regions. In another case where there are two or more single nucleotide polymorphisms constituting an identification marker, the variety identification region may be composed of one region having all of these single nucleotide polymorphisms, or two or more regions each having at least one single nucleotide polymorphism. Specific examples of the variety identification region include regions comprising at least one of the single nucleotide polymorphisms or indel portions indicated by the symbol "n" at the following nucleotide positions:

nucleotide positions 74, 77, 87, 103, 116, 118, 121, 125, 134, 135, 148, 192, 195, 197, 199, 203, 204, 226, 230, 235, 306, 316, 330 and 532 in the nucleotide sequence of SEQ ID NO: 9 (region A1);

nucleotide positions 178, 204, 227, 234, 370, 426, 439, 547, 562 and 624 in the nucleotide sequence of SEQ ID NO: 10 (region B1);

nucleotide positions 3, 13, 17, 87, 88, 129, 130, 131, 132, 133, 134, 254, 331, 356, 375, 380, 396, 398, 399, 421, 460, 474, 475, 476, 477, 480, 481, 500 and 547 (positions 129-134 constitute an indel portion) in the nucleotide sequence of SEQ ID NO: 11 (region C1);

nucleotide positions 34, 101, 118, 124, 164, 168, 171, 186, 187, 188, 189, 190, 191, 192, 193, 194, 392, 398, 399, 459 and 502 (positions 186-194 and position 399 each constitute an indel portion) in the nucleotide sequence of SEQ ID NO: 12 (region A1-2-L);

nucleotide positions 2, 12, 31, 98, 115, 121, 161, 165, 168, 183, 184, 185, 186, 187, 188, 189, 190, 191, 389, 395, 396, 456 and 499 (position 12, positions 183-191, and position 396 each constitute an indel portion) in the nucleotide sequence of SEQ ID NO: 13 (region A1-2-L);

nucleotide positions 1, 2, 3, 5, 8, 9, 10, 11, 12, 13, 14, 15, 16, 17, 20, 21, 25, 26, 27, 28, 29, 30, 31, 33, 35, 36, 37, 38, 41, 42, 43, 44, 46, 47, 48, 50, 51, 56, 57, 58, 59, 63, 65, 68, 72, 78, 79, 84, 86, 88, 90, 92, 118, 153, 154, 191, 205, 206, 226, 228, 233, 254, 289, 315, 350, 392 and 405 (positions 57-59 and position 65 each constitute an indel portion) in the nucleotide sequence of SEQ ID NO: 14 (region A1-2-R); and nucleotide positions 2, 6, 12, 13, 18, 20, 22, 24, 26, 36, 52, 87, 88, 125, 139, 140, 160, 162, 167, 188, 223, 249, 273, 284, 326, 339, 421 and 437 (position 437 constitutes an indel portion) in the nucleotide sequence of SEQ ID NO: 15 (region A1-2-R).

In one mode, the variety identification region may be a region that is composed of part or all of the nucleotide sequence of SEQ ID NO: 9 (region A1) and which comprises at least one of the single nucleotide polymorphisms indicated by the symbol n, or may be a region comprising the nucleotide sequence of SEQ ID NO: 9. Alternatively, the variety identification region may be a region that is composed of part or all of the nucleotide sequence of SEQ ID NO: 10 (region B1) and which comprises at least one of the single nucleotide polymorphisms indicated by the symbol n, or may be a region comprising the nucleotide sequence of SEQ ID NO: 10. Alternatively, the variety identification region may be a region that is composed of part or all of the nucleotide sequence of SEQ ID NO: 11 (region C1) and which comprises at least one of the single nucleotide polymorphisms or indel portion indicated by the symbol n, or may be a region comprising the nucleotide sequence of SEQ ID NO: 11. Alternatively, the variety identification region may be a region that is composed of part or all of the nucleotide sequence of SEQ ID NO: 12 or 13 (region A1-2-L) and which comprises at least one of the single nucleotide polymorphisms or indel portions indicated by the symbol n, or may be a region comprising the nucleotide sequence of SEQ ID NO: 12 or 13. Alternatively, the variety identification region may be a region that is composed of part or all of the nucleotide sequence of SEQ ID NO: 14 or 15 (region A1-2-R) and which comprises at least one of the single nucleotide polymorphisms or indel portions indicated by the symbol n, or may be a region comprising the nucleotide sequence of SEQ ID NO: 14 or 15.

In another mode, the variety identification region may be composed of two or more regions selected from the group consisting of: a region that is composed of part or all of the nucleotide sequence of SEQ ID NO: 9 (region A1) and which comprises at least one of the single nucleotide polymorphisms indicated by the symbol n; a region that is composed of part or all of the nucleotide sequence of SEQ ID NO: 10 (region B1) and which comprises at least one of the single nucleotide polymorphisms indicated by the symbol n; a region that is composed of part or all of the nucleotide sequence of SEQ ID NO: 11 (region C1) and which comprises at least one of the single nucleotide polymorphisms or indel portion indicated by the symbol n; a region that is composed of part or all of the nucleotide sequence of SEQ ID NO: 12 or 13 (region A1-2-L) and which comprises at least one of the single nucleotide polymorphisms or indel portions indicated by the symbol n; and a region that is composed of part or all of the nucleotide sequence of SEQ ID NO: 14 or 15 (region A1-2-R) and which comprises at least one of the single nucleotide polymorphisms or indel portions indicated by the symbol n. Alternatively, the variety identification region may be composed of two or more regions, three or more regions, or four or more regions selected from the group consisting the following regions, or composed of all five of the following regions: a region comprising the nucleotide sequence of SEQ ID NO: 9 (region A1), a region comprising the nucleotide sequence of SEQ ID NO: 10 (region B1), a region comprising the nucleotide sequence of SEQ ID NO: 11 (region C1), a region comprising the nucleotide sequence of SEQ ID NO: 12 or 13 (region A1-2-L), and a region comprising the nucleotide sequence of SEQ ID NO: 14 or 15 (region A1-2-R).

In yet another mode, the variety identification region may be composed of not only one or more regions selected from the group consisting of: a region that is composed of part or all of the nucleotide sequence of SEQ ID NO: 9 (region A1) and which comprises at least one of the single nucleotide polymorphisms indicated by the symbol n; a region that is composed of part or all of the nucleotide sequence of SEQ ID NO: 10 (region B1) and which comprises at least one of the single nucleotide polymorphisms indicated by the symbol n; and a region that is composed of part or all of the nucleotide sequence of SEQ ID NO: 11 (region C1) and which comprises at least one of the single nucleotide polymorphisms or indel portion indicated by the symbol n; but also a region that is composed of part or all of the nucleotide sequence of SEQ ID NO: 12 or 13 (region A1-2-L) and which comprises at least one of the single nucleotide polymorphisms or indel portions indicated by the symbol n, or a region that is composed of part or all of the nucleotide sequence of SEQ ID NO: 14 or 15 (region A1-2-R) and which comprises at least one of the single nucleotide polymorphisms or indel portions indicated by the symbol n. Alternatively, the variety identification region may be composed of not only one or more regions, preferably two or more regions, selected from the group consisting of the following regions, or more preferably all three of the following regions: a region comprising the nucleotide sequence of SEQ ID. NO: 9 (region A1), a region comprising the nucleotide sequence of SEQ ID NO: 10 (region B1), and a region comprising the nucleotide sequence of SEQ ID NO: 11 (region C1); but also a region that is composed of part or all of the nucleotide sequence of SEQ ID NO: 12 or 13 (region A1-2-L) and which comprises at least one of the single nucleotide polymorphisms or indel portions indicated by the symbol n, or a region that is composed of part or all of the nucleotide sequence of SEQ ID NO: 14 or 15 (region A1-2-R) and which comprises at least one of the single nucleotide polymorphisms or indel portions indicated by the symbol n. Alternatively, the variety identification region may be composed of not only one or more regions, preferably two or more regions, selected from the group consisting of the following regions, or more preferably all three of the following regions: a region comprising the nucleotide sequence of SEQ ID NO: 9 (region A1), a region comprising the nucleotide sequence of SEQ ID NO: 10 (region B1), and a region comprising the nucleotide sequence of SEQ ID NO: 11 (region C1); but also a region comprising the nucleotide sequence of SEQ ID NO: 12 or 13 (region A1-2-L), or a region comprising the nucleotide sequence of SEQ ID NO: 14 or 15 (region A1-2-R).

The variety identification primers may be primers capable of amplifying an identification region, which are determined in the process of preparing an identification marker, or primers separately designed to be capable of amplifying a region comprising an identification marker (i.e., variety identification region). In a case where single nucleotide polymorphisms constituting an identification marker are present in two or more regions, the variety identification primers may be sets of primers capable of amplifying the respective regions. In another case where there are two or more single nucleotide polymorphisms constituting an identification marker, the variety identification primers may be primers capable of amplifying one region having all of these single nucleotide polymorphisms, or two or more sets of primers capable of amplifying the respective two or more regions each having at least one of these single nucleotide polymorphisms.

Examples of the primers that can be used as variety identification primers include primers consisting of the nucleotide sequences of SEQ ID NOs: 1-8. Examples of the primer set to be used for amplifying DNA fragments at step (i) include primer sets consisting of one or more combinations of primers selected from the group consisting of a combination of primers consisting of the nucleotide sequences of SEQ ID NOs: 1 and 2, a combination of primers consisting of the nucleotide sequences of SEQ ID NOs: 3 and 4, a combination of primers consisting of the nucleotide sequences of SEQ ID NOs: 5 and 6, and a combination of primers consisting of the nucleotide sequences of SEQ ID NOs: 7 and 8.

In another mode, step (i) is performed by PCR using one or more primer sets, preferably two or more primer sets, selected from the group consisting of the following combinations of primers, or more preferably all three of the following combinations: a combination of primers consisting of the nucleotide sequences of SEQ ID NOs: 1 and 2, a combination of primers consisting of the nucleotide sequences of SEQ ID NOs: 3 and 4, and a combination of primers consisting of the nucleotide sequences of SEQ ID NOs: 5 and 6.

In another mode, step (i) is performed by PCR using not only the following three primer sets: a combination of primers consisting of the nucleotide sequences of SEQ ID NOs: 1 and 2, a combination of primers consisting of the nucleotide sequences of SEQ ID NOs: 3 and 4, and a combination of primers consisting of the nucleotide sequences of SEQ ID NOs: 5 and 6; but also a primer set consisting of a combination of primers consisting of the nucleotide sequences of SEQ ID NOs: 7 and 8.

(ii) Identifying the Genotype of a Single Nucleotide Polymorphism

For each of the DNA fragments amplified at step (i), the genotype of a single nucleotide polymorphism is identified.

In one mode, the identification of the genotype of a single nucleotide polymorphism is performed by identifying the nucleotide sequence of each of DNA fragments containing a variety identification region. Nucleotide sequence analysis may be made, for example, according to or in line with the techniques described above in the headings of "(5) Purifying PCR products" to "(8) Analyzing nucleotide sequences" in the subsection titled "(f) Determining the nucleotide sequence of an identification region, and (g) determining an identification marker for varieties to be identified" of the section titled "<Method for preparing an identification marker>".

In another mode, the identification of the genotype of a single nucleotide polymorphism may be performed by contacting each of amplified DNA fragments with probes and/or primers for use in detecting a single nucleotide polymorphism that constitutes an identification marker and which differs among hop varieties. The probes and/or primers for use in detecting a single nucleotide polymorphism can be designed and prepared according to a technique known to those skilled in the art. The identification of the genotype of a single nucleotide polymorphism using the thus-obtained probes can be performed using a technique known to those skilled in the art, such as DNA microarray method. The identification of the genotype of a single nucleotide polymorphism using primers can be performed according to a sequence analysis-based technique, or according to an identification technique using primers designed to produce amplification products of different lengths depending on the single nucleotide polymorphism to be detected, as exemplified by SNaPshot® method (Life Technologies). The identification of the genotype of a single nucleotide polymorphism using probes and primers can be performed, for example, by realtime PCR using a combination of the MGB (Minor Groove Binder) probes (Life Technologies) and primers designed to sandwich the same.

(iii) Making Comparison and Analysis in Terms of the Genotype of a Single Nucleotide Polymorphism in a Variety Identification Region At step (iii), the genotype of a single nucleotide polymorphism constituting an identification marker in a variety identification region in each of DNAs from hops to be tested is compared with the genotype of a single nucleotide polymorphism in a corresponding region in a DNA from a known hop variety. In this comparison, it is analyzed whether the hop varieties to be tested and the known hop variety are concordant or discordant for the genotype of the single nucleotide polymorphism constituting the identification marker.

This comparison can be made by visual inspection or mathematical computation. A computer program can also be used for comparison. Alternatively, this comparison may be made by comparing the nucleotide sequence of each of DNA fragments containing a variety identification region with the nucleotide sequence of a corresponding region in a DNA from a known hop variety. The comparison can be made by a technique generally adopted in an assay for a single nucleotide polymorphism found on the gene of a subject (e.g., SNP typing).

The specific example given below is a technique for directly comparing nucleotide sequences using an analysis computer program. An identification marker table for an identification marker obtained by the identification marker preparation method described above, which comprises data showing nucleotides and data showing the positions of said nucleotides in nucleotide sequence, is stored in advance on a computer on which an analysis computer program like SeqScape (Life Technologies) operates. The identification marker table to be stored may be composed of one table or two or more tables. Then, a list of the nucleotide sequence of a hop to be tested, including nucleotide data obtained from each of hops to be tested, is stored on the computer.

Thereafter, with reference being made to the data showing nucleotide positions in nucleotide sequence, which is contained in the identification marker table, comparison is made on the computer between the two data each showing nucleotides located at nucleotide sequence positions that correspond between the nucleotide sequence list of the hop to be tested and the identification marker table. The comparison can be made by aligning both of the two nucleotide sequences using the analysis computer program.

(iv) Identifying the Varieties of Hops to be Tested

At step (iv), the varieties of hops to be tested are identified on the basis of the analysis results obtained at step (iii).

To be specific, it is analyzed whether a nucleotide(s) at that site of the nucleotide sequence of a hop to be tested which corresponds to an identification marker is(are) perfectly concordant with a nucleotide(s) of the identification marker, and in the case of perfect concordance, the hop to be tested is identified to be of the variety for which the identification marker is designed.

Thus, the varieties of hops to be tested can be identified using the identification marker of the present invention. In a case where analysis is made using a computer, the varieties of hops to be tested can be identified easily and quickly by recording in advance the nucleotide sequences of regions having identification markers for two or more varieties and successively making comparison and analysis between the nucleotide sequence of each of the hops to be tested and that recorded for each of the varieties.

In addition, the above-mentioned comparison can be made easily by coloring a particular nucleotide(s) determined as an identification marker. More specifically, a nucleotide sequence having a colored control nucleotide(s) (identification marker) and the nucleotide sequence of a hop to be tested are first aligned, and then a table is generated by extracting and comparing the colored nucleotide(s) and a nucleotide(s) corresponding thereto. This facilitates determination of whether or not the hop to be tested and the identification marker are perfectly concordant in terms of the nucleotide type and position, and makes it possible to easily determine whether or not the hop to be tested is of the variety for which the identification marker is designed. This technique is preferred because it enables simultaneous analysis of two or more hops to be tested.

<Nucleic Acid Comprising an Identification Marker>

The present invention also provides a nucleic acid comprising at least part of an identification marker prepared by the identification marker preparation method described above.

As referred to herein, the "nucleic acid" refers to a deoxyribonucleic acid (DNA) or ribonucleic acid (RNA) composed of two or more nucleotides. It will be understood by those skilled in the art that, in a case where a RNA is meant as a nucleic acid described by the nucleotide sequence of a DNA, the nucleic acid should be understood by replacing a thymine(s) in the nucleotide sequence of the DNA with an uracil(s). The nucleic acid may be a single-stranded nucleic acid or a double-stranded nucleic acid formed by hybridization with a complementary strand.

To be specific, the nucleic acid comprising at least part of an identification marker can be a nucleic acid comprising part of a nucleotide sequence selected from the group consisting of SEQ ID NO: 9 (region A1), SEQ ID NO: 10

(region B1), SEQ ID NO: 11 (region C1), SEQ ID NO: 12 or 13 (region A1-2-L), and SEQ ID NO: 14 or 15 (region A1-2-R) and further comprising at least one of the single nucleotide polymorphisms or indel portions indicated by the symbol n in said nucleotide sequences. Preferably, the nucleic acid comprising at least part of an identification marker can be a nucleic acid comprising a nucleotide sequence selected from the group consisting of SEQ ID NO: 9 (region A1), SEQ ID NO: 10 (region B1), SEQ ID NO: 11 (region C1), SEQ ID NO: 12 or 13 (region A1-2-L), and SEQ ID NO: 14 or 15 (region A1-2-R).

<Primers>

The present invention also provides primers capable of amplifying the above-described nucleic acid comprising at least part of an identification marker.

The primers are not particularly limited as long as they are designed to be capable of amplifying the above-described nucleic acid comprising at least part of an identification marker.

<Probes>

The present invention also provides probes for use in detecting a single nucleotide polymorphism constituting an identification marker.

The probes are, for example, those which are capable of detecting at least one of the single nucleotide polymorphisms or indel portions indicated by the symbol n, in a nucleotide sequence selected from the group consisting of SEQ ID NO: 9 (region A1), SEQ ID NO: 10 (region B1), SEQ ID NO: 11 (region C1), SEQ ID NO: 12 or 13 (region A1-2-L), and SEQ ID NO: 14 or 15 (region A1-2-R).

<Method for Detecting Mixing of a Different Hop Variety>

In a case where it is concerned that a different hop variety may be mixed, the mixing of the different hop variety can be detected using the identification marker of the present invention, for example, according to the method described below.

A method for detecting mixing of a different hop variety in a hop sample, the method comprising the steps of:
(i) amplifying a fragment of a DNA extracted from a hop sample to be tested, the fragment which comprises a variety identification region, wherein the variety identification region comprises an identification marker composed of at least one single nucleotide polymorphism (SNP) that differs among hop varieties;
(ii) analyzing the nucleotide sequence of the variety identification region in the DNA fragment amplified at step (i) to obtain sequence data;
(iii) comparing the information on a single nucleotide polymorphic site constituting the identification marker, which is contained in the sequence data obtained at step (ii), with the information on a corresponding single nucleotide polymorphic site in a normal hop; and
(iv) determining the presence or absence of mixing of the different hop variety in the hop sample, wherein, in the case where the information on the single nucleotide polymorphic site in the sequence data obtained at step (ii) is concordant with the information on the corresponding single nucleotide polymorphic site in the normal hop, it is determined that no different hop variety is mixed, or in the case where the information on the single nucleotide polymorphic site in the sequence data obtained at step (ii) is discordant with the information on the corresponding single nucleotide polymorphic site in the normal hop, it is determined that a different hop variety is mixed.

Further, the variety of the hop mixed can be deduced or identified by performing, subsequently to step (iv), the steps of:

(v) identifying a nucleotide different from that of the normal hop, on the basis of an information derived from a hop other than the normal one, which appears in the single nucleotide polymorphic site in the sequence data obtained at step (ii), in the case where it is determined at step (iv) that the information on the single nucleotide polymorphic site in the sequence data obtained at step (ii) is discordant with the information on the corresponding single nucleotide polymorphic site in the normal hop; and
(vi) checking the nucleotide different from that of the normal hop, which is identified in the single nucleotide polymorphic site at step (v), against the identification marker to deduce or identify the variety of the hop mixed.

Furthermore, the proportion of the hop variety mixed can be analyzed by performing, subsequently to step (iv), the steps of:

(v) identifying a nucleotide different from that of the normal hop, and determining the mixing proportion thereof, on the basis of an information derived from a hop other than the normal one, which appears in the single nucleotide polymorphic site in the sequence data obtained at step (ii), in the case where it is determined at step (iv) that the information on the single nucleotide polymorphic site in the sequence data obtained at step (ii) is discordant with the information on the corresponding single nucleotide polymorphic site in the normal hop; and
(vi) checking the nucleotide different from that of the normal hop, which is identified in the single nucleotide polymorphic site at step (v), against the identification marker to deduce or identify the variety of the hop mixed and the proportion of the hop variety mixed.

As referred to herein, the information on a single nucleotide polymorphic site in sequence data refers to, for example, a shape or value of a single nucleotide polymorphic site, which are obtained as the result of sequencing. Specific examples include an electropherogram of a single nucleotide polymorphic site which is obtained as the result of sequencing (i.e., color-coded waveforms showing various nucleotides, which are obtained upon sequencing), and the proportion of a different nucleotide present in a single nucleotide polymorphic site, which is obtained by cloning an amplified fragment in *E. coli* or the like, sequencing the resulting two or more clones, and comparing the sequences thereof.

As referred to herein, the normal hop refers to a single variety of hop whose information on a single nucleotide polymorphic site constituting an identification marker has been established. In some cases, this term may refer to a sample composed exclusively of a single variety of hop whose information on a single nucleotide polymorphic site constituting an identification marker has been established.

In the case of detecting mixing of a different hop variety using an electropherogram, the presence of the different hop variety can be determined by observing superimposition of waveforms other than those of a normal hop on an electropherogram of a hop sample to be tested. And the variety of the hop mixed can be deduced or identified by identifying a nucleotide(s) different from that of the normal hop on the basis of other waveforms than those of the normal one, which appear in a single nucleotide polymorphic site, and checking the different nucleotide(s) against an identification marker. If a case where all nucleotide(s) characteristic of the variety of interest which are present in an identification marker (SNP) is(are) observed, the variety of the hop mixed can be identified. Further, the approximate proportion of the different hop variety mixed can be determined by comparing the overlapping degrees, heights and the like of the resulting waveforms with the analysis results separately obtained from a sample mixed with a different hop variety, whose mixing proportions of respective varieties have been known.

In the case of using sequence data of two or more clones obtained by cloning an amplified fragment in *E. coli* or the like, mixing of a different hop variety can be detected by aligning the sequences of the two or more clones and determining the proportion of a different nucleotide(s) contained in each single nucleotide polymorphic site. In other words, if no different hop variety is mixed, the proportion of the same nucleotides as those of the normal hop should be 100% in every site, but if any different hop variety is mixed, the proportion of the same nucleotides as those of the normal hop should not be 100%, and a more or less certain proportion of a different nucleotide(s) should be observed. By checking a different nucleotide(s) from that of a normal hop against an identification marker in this way, the variety of a hop mixed can be identified, and the proportion of the hop variety mixed can be determined. However, it should be noted that the technique based on cloning in *E. coli* requires an enormous amount of effort and time for analyzing a large number of clones.

Another technique for determining the proportion of a different nucleotide(s) contained in each single nucleotide polymorphic site is a technique in which DNA fragments containing a variety identification region which are obtained from a hop sample to be tested are amplified using specific primers with additional sequences which are required for the next step, the amplified fragments are sequenced in a large volume using a next-generation sequencer, and the resulting sequence data are aligned to determine the proportion of a different nucleotide(s) contained in each single nucleotide polymorphic site. This technique makes it possible to identify the variety of a hop mixed and determine the proportion of the hop variety mixed more accurately.

There is yet another technique in which a primer is placed immediately before a polymorphism (SNP) to extend only a single nucleotide, and the polymorphism is genotyped on the basis of the type of the single nucleotide incorporated. Examples include a technique designated as the SNaPshot® method (Life Technologies). There is further another technique that allows quantitative analysis of a different variety by realtime PCR using the MGB (Minor Groove Binder) probes (Life Technologies).

EXAMPLES

Hereunder, the present invention will be more specifically described by way of Examples. However, this invention is not limited to these examples.

Example 1: Preparing an Identification Marker (a) Transcriptome Analysis

In order to obtain intra-variety DNA polymorphic regions required for developing a hop variety identification technique, the present inventors contemplated widely searching for SNPs from large quantities of sequence data obtained using a next-generation sequencer (in the case of human genome, the frequency at which a SNP is detected is believed to be 1 SNP per 100-300 nucleotides; http://www.eubios.info/hmback.htm). Thus, the inventors focused on transcriptome. Transcriptome analysis only requires about 100 times less data processing than whole-genome analysis, thereby reducing lead time and cost. Besides, according to our calculation, there is available data for as much as 15000 SNPs in transcriptome analysis, though this number is smaller than that of the whole-genome analysis. Thus, we made an intra-variety SNP analysis using this technique on the assumption that SNPs required for identification of many varieties could be obtained thereby.

(1) Collecting and Storing Samples

From among the varieties to be identified which are listed in Table 4 given in a subsequent section, three varieties (referred to as varieties A, B and C for convenience) were selected, and fresh hop leaves of these varieties were collected. More specifically, the leaves were sampled and stored according to the procedure described below:

a. Tissue: As young (small, yellow-green, soft) leaves as possible were collected. However, those leaves with white foreign matters on the surface were excluded.

b. Methodology: In order to prevent RNase contamination, leaves were collected by hand with surgical gloves. Upon collection, the leaves were soaked in a reagent for preventing RNA degradation.

c. Storage: Though RNA is stable for at least one week even at room temperature, the leaves were kept stored in a refrigerator as much as possible until being subjected to transcriptome analysis and SNP sequence analysis.

(2) Transcriptome Analysis

The thus-collected samples were subjected to transcriptome analysis under a subcontract to Eurofins. To be specific, the samples were subjected to total RNA extraction, mRNA purification, cDNA library preparation, equalization of variations in expression amount, size control (500-700 bp), preparation of cDNA libraries for a GS FLX sequencer, and sequencing with the Roche/454 Genome Sequencer FLX using Titanium chemistry.

(b) Assembling (Preparing Contigs)

SNP Analysis Using Transcriptome Data

With the use of the sequence data obtained by the transcriptome analysis described above, contigs were prepared under a subcontract to Eurofins. To be specific, on the basis of the nucleotide sequences of DNA fragments, sequence clustering and assembling were performed for each of the varieties. As a result, the nucleotide sequences of about 42000-45000 contigs (part of cDNAs) were obtained from each of the varieties. Among these contigs, there were about 4500-6700 contigs with a length of 1000 bp or longer.

TABLE 1

| | Variety C | Variety A | Variety B |
| --- | --- | --- | --- |
| Total number of contigs | 45432 | 43638 | 42395 |
| (Contigs of ≥1000 bp) | (4563) | (6725) | (6157) |

(c) Searching for SNPs

Next, with the use of the sequence data of the contigs and singlets obtained by the assembling described above, SNPs were searched for under a subcontract to Eurofins. To be specific, with the nucleotide sequences of the contigs and singlets of variety C being used as reference sequences, single reads of varieties B and A were each applied and mapped to the reference sequences according to whether they share a common portion. Further, contigs constituted by the mapped single reads were identified from the assembling information deployed on an analysis software. The reference sequences as well as the contigs and/or singlets of the other varieties, as thus obtained, are aligned to search for SNPs (bioinformatics analysis). However, simply doing this was not sufficient; thus, with the nucleotide sequences of the contigs and singlets of variety B being used as reference sequences, single reads of varieties A and C were applied and mapped to the reference sequences to search for SNPs in the same way as mentioned above, and furthermore, with the nucleotide sequences of the contigs and singlets of variety A being used as reference sequences, single reads of varieties B and C were applied and mapped to the reference sequences to search for SNPs in the same way as mentioned above.

(d) Selecting SNP-Containing Regions and Designing Primers

With the use of the SNP data obtained by the SNP search described above, SNPs which are homozygous in two varieties other than the reference were extracted, and from among these SNPs, regions with the highest number of SNPs per contig were further extracted. The results are shown in the table given below.

TABLE 2

| Reference/ Variety supplied | Total number of contigs | Total number of SNPs detected | Number of SNPs homozygous in 2 varieties other than reference (per contig) | Contig size (bp) | Analysis region |
| --- | --- | --- | --- | --- | --- |
| Variety B | 42395 | 14408 | 9 | 1.0 k | B1 |
| Variety A | 43638 | 10472 | 6 | 1.4 k | A1 |
| Variety C | 45432 | 19330 | 24 | 2.8 k | C1 |
| Variety A | 43638 | 10472 | 6 | 719 | A1-2 |

The thus-selected analysis regions were designated as regions B1, A1, C1 and A1-2, respectively, and sets of primers capable of amplifying SNP-containing areas were designed and synthesized. The sequences of these primer sets are shown below.

TABLE 3

| Primer | Length | Tm (° C.) | GC % | Nucleotide sequence |
| --- | --- | --- | --- | --- |
| A1-3L | 20 | 60.3 | 50 | TAAGGTGTTGGGAGGGTTGA (SEQ ID NO: 1) |
| A1-3R | 20 | 60.4 | 55 | CCACCAATAACAGGCTCCAC (SEQ ID NO: 2) |
| Amplification product: 651 | | | | |
| B1-1L | 21 | 59.0 | 43 | CAGACTTGTGGCTGTCAAAAA (SEQ ID NO: 3) |
| B1-1R | 20 | 60.0 | 55 | CTTCTCCTTCGAACCTGTCG (SEQ ID NO: 4) |
| Amplification product: 729 (including introns) | | | | |
| C1-1L | 20 | 59.9 | 35 | CGGCGTTTTTCAATTTTCAT (SEQ ID NO: 5) |
| C1-1R | 20 | 60.3 | 55 | GTGATGACTCGGGCTTCAGT (SEQ ID NO: 6) |
| Amplification product: 646 | | | | |
| A1-2-1L | 23 | 56.9 | 45 | GAAATCTGCTTKGAGAAACCTGG (SEQ ID NO: 7) |
| A1-2-1R | 23 | 56.9 | 43 | GCAGGTATCTTTGTAGGTACATC (SEQ ID NO: 8) |
| Amplification product: ca. 1500 | | | | |

(e) Determining Identification Regions and Primers

DNAs were extracted from pellets or dried cones of the three hop varieties (varieties A, B and C) used in the transcriptome analysis described above, and were subjected to amplification of respective regions A1, B1, C1 and A1-2 using the primer sets shown in Table 3 and to direct sequencing by the Sanger's method. To be specific, the same procedures as described below in (2) to (8) under (f) were followed. As a result, it was confirmed that the regions can be amplified. Also, comparison was made with the data obtained using the next-generation sequencer, to confirm that identification of the three varieties A, B and C is possible.

(f) Sequencing of Identification Regions Using Varieties to be Identified

It was determined that the analysis of regions A1, B1, C1 and A1-2 (and SNPs contained therein) is also applicable to identification of other varieties than the above-mentioned three varieties; thus, analysis was made of an increased number of varieties.

(1) Varieties Subjected to Identification of Hop Varieties

As varieties to be identified, there were used 14 varieties listed below in Table 4.

TABLE 4

| Country of origin | Hop variety |
| --- | --- |
| Czech | Saaz |
|  | Sladeck |
|  | Premiant |
| Germany | Tradition |
|  | Spalter |
|  | Spalter Select |
|  | Perle |
|  | Tettnang |
|  | Brewer's Gold |
|  | Northern Brewer |
|  | Magnum |
|  | Herkules |
|  | German Nugget |
|  | Taurus |

(2) DNA Extraction a. Extraction from Hop Pellets

Hop pellets were ground in a mortar or finely crushed with a spatula or the like, and DNAs were extracted from 10-50 mg of the ground material using the CTAB method described below.

DNA extraction by the CTAB (cetyltrimethyl ammonium bromide) method was carried out as follows. There were prepared a CTAB solution composed of 2% (w/v) CTAB (Calbiochem), 100 mM Tris-HCl (pH 8.0), 20 mM EDTA (pH 8.0), 1.4 M NaCl, and 1% (w/v) PVP (polyvinylpyrrolidone). Next, 650 µL of the CTAB solution and 2 µL of a 1 mg/mL RNaseA solution, together with the previously ground material, were put in a 1.5 mL microtube and stirred well. This microtube containing the sample and the CTAB solution was submerged in a constant temperature bath held at 65° C. such that the content of the tube was completely underwater, and was incubated for one hour to disrupt hop cells. Then, an equivalent volume (650 µL) of chloroform/isoamyl alcohol (24:1) was added, and the mixture was manually mixed by inversion for 3 minutes. The mixture was centrifuged in a short time (using Beckman's Allegra 21R centrifuge and F2402H rotor at 15,000 rpm (ca. 15,000×g) for 1-5 minutes) and thereby fractionated into an organic solvent layer (lower) and an aqueous layer (upper), and the aqueous layer (ca. 400 µL) was removed to a new tube. After an equivalent volume of isopropyl alcohol was added, the mixture was mixed by inversion and then centrifuged in the same way as described above. The supernatant was discarded, and the remaining sediment was rinsed with about 500 µL of 70% ethanol and dried in a centrifugal evaporator for about 5 minutes. The resulting product was dissolved into 20-50 µL of a TE buffer to obtain a sample to be used as a DNA sample.

b. Extraction from Dried Hop Cones

About 1 g of dried hop cones were ground in a mortar in the presence of liquid nitrogen, and 10-50 mg of the ground material was used to prepare a DNA sample in the same way as described above.

(3) PCR

Amplification of DNA fragments of identification regions was performed using PCR reaction solutions (50 µL; 0.2 mL microtube) made with the DNA samples prepared above in (2) and PerfectShot Ex Taq (Loading dye mix) (Takara Bio Inc.) in line with the attached instructions. Regions A1, B1, C1 and A1-2 were selected as identification regions, and the DNA fragments of these regions were amplified. The following summarizes the names and nucleotide sequences of the primers for use in amplifying the DNA fragments of the respective identification regions, as well as the constitutions of the PCR reaction solutions and PCR reaction conditions.

```
Primer set for analyzing region A1
                                       (SEQ ID NO: 1)
A1-3L:          TAAGGTGTTGGGAGGGTTGA (SEQ ID NO: 2)
A1-3R:          CCACCAATAACAGGCTCCAC Primer set for analyzing region B1
                                       (SEQ ID NO: 3)
B1-1L:          CAGACTTGTGGCTGTCAAAAA (SEQ ID NO: 4)
B1-1R:          CTTCTCCTTCGAACCTGTCG Primer set for analyzing region C1
                                       (SEQ ID NO: 5)
C1-1L:          CGGCGTTTTCAATTTTCAT (SEQ ID NO: 6)
C1-1R:          GTGATGACTCGGGCTTCAGT Primer set for analyzing region A1-2
                                       (SEQ ID NO: 7)
A1-2-1L:        GAAATCTGCTTKGAGAAACCTGG (SEQ ID NO: 8)
A1-2-1R:        GCAGGTATCTTTGTAGGTACATC
```

TABLE 5

| PCR conditions for analysis in region A1 | | | | |
|---|---|---|---|---|
| Perfect Shot ExTaq | 25 µl | Temp (° C.) | Time (sec) | Number of repeat times |
| 100 µM A1-3L | 0.5 | | | |
| 100 µM A1-3R | 0.5 | 98 | 10 | |
| DNA | 0.5 | 60 | 30 | 30 |
| Sterile water | 23.5 | 72 | 60 | |
| Total | 50 µl | 4 | | Retained |
| PCR conditions for analysis in region B1 | | | | |
| Perfect Shot ExTaq | 25 µl | Temp (° C.) | Time (sec) | Number of repeat times |
| 100 µM B1-1L | 0.5 | | | |
| 100 µM B1-1R | 0.5 | 98 | 10 | |
| DNA | 0.5 | 60 | 30 | 30 |
| Sterile water | 23.5 | 72 | 60 | |
| Total | 50 µl | 4 | | Retained |

TABLE 5-continued

| PCR conditions for analysis in region C1 | | | | |
|---|---|---|---|---|
| Perfect Shot ExTaq | 25 µl | Temp (° C.) | Time (sec) | Number of repeat times |
| 100 µM C1-1L | 0.5 | | | |
| 100 µM C1-1R | 0.5 | 98 | 10 | |
| DNA | 0.5 | 60 | 30 | 30 |
| Sterile water | 23.5 | 72 | 60 | |
| Total | 50 µl | 4 | | Retained |
| PCR conditions for analysis in region A1-2 | | | | |
| Perfect Shot ExTaq | 25 µl | Temp (° C.) | Time (sec) | Number of repeat times |
| 100 µM A1-2-1L | 0.5 | | | |
| 100 µM A1-2-1R | 0.5 | 98 | 10 | |
| DNA | 0.5 | 60 | 30 | 30 |
| Sterile water | 23.5 | 72 | 60 | |
| Total | 50 µl | 4 | | Retained |

(4) Confirming Amplification by PCR

Five microliters each of the PCR reaction solutions prepared above was subjected to agarose gel electrophoresis. In this process, the electrophoresis was performed using the mini gel electrophoresis system Mupid (gel: 3% NuSieve 3:1 Agarose (FMC BioProducts or Cambrex Bio Science Rockland); electrophoresis conditions: 100 V, 30 minutes), and the amplification products were stained in a 2 µg/mL ethidium bromide solution for about 40 minutes, and photographed under UV light. As a result, it was confirmed that for each of the DNA samples, a DNA fragment of intended size was amplified. The sizes of DNA fragments amplified using the respective primer sets are summarized in the table given below.

TABLE 6

| Primer set | Amplified fragment size (bp) |
|---|---|
| A1-3L/A1-3R | 651 |
| B1-1L/B1-1R | 729 (including introns) |
| C1-1L/C1-1R | 646 |
| A1-2-1L/A1-2-1R | ca. 1500 |

(5) Purifying PCR Products

Purification of the resulting PCR products was performed using the QIAquick PCR Purification Kit (50) (Qiagen) according to the protocol by the following procedure. More specifically, 5 times the volume of a PBI buffer (225 µL) was added to the PCR reaction solution (remaining amount of about 45 µL), and the solution was mixed. The resulting solution was placed in the QIA quickspin and centrifuged at 13,000 rpm (ca. 11,000×g) for one minute. The filtrate was discarded, 750 µL of a PE buffer was added, and then the solution was centrifuged at 13,000 rpm for one minute. The filtrate was discarded, and the remaining solution was centrifuged again at 14,000 rpm (ca. 13,000×g) for one minute. The filtrate was discarded, the column was transferred to a new 1.5 mL Eppendorf tube, and 30 µL of an EB buffer was added. After being left to stand for one minute, the solution was centrifuged at 13,000 rpm for 2 minutes to recover the filtrate as a sample.

(6) Cycle Sequencing Reaction and Purifying Sequencing Products

Cycle sequencing was performed by the following procedure using the BigDye Terminator v1.1 Cycle Sequencing Kit (Life Technologies) according to the Japanese-version protocol for this kit (e.g., "Cycle Sequencing of Single- and Double-Stranded DNA" on page 22, "Cycle Sequencing on the GeneAmp PCR System 9700, 9600, 2700, or 2400" on page 25, and "Spin Column (Spin Plate) Purification" on pages 38-40). Additionally, the nucleotide sequences of the primers used for cycle sequencing were the same as those of the primers used in the PCR amplification of the DNA fragments of interest. The purified PCR product solution was diluted with sterile distilled water so as to give a concentration of 5-20 ng/μL. To 2 μL of the resulting solution, 8 μL of Sequence Premix (for BigDye) was added as well as 3.2 μL each of the primers diluted to 1 μM was added alone (either one of each set of primers was added), and the volume was adjusted with sterile distilled water to obtain a cycle sequencing reaction solution with a final volume of 20 μL. The reaction solution was put in a 0.2 mL microtube (for PCR), which was then placed in a PCR system (DNA Thermal Cycler GeneAmp PCR System 9600; formerly Perkin Elmer). After preliminary denaturation (e.g., at 96° C. for 1 min), the reaction cycle of denaturation (e.g., at 96° C. for 10 sec), annealing (e.g., at 50° C. for 5 sec), and strand extension (e.g., at 60° C. for 4 min) was repeated 25 times. In a case where it was not possible to take out the sample immediately after completion of the reaction, it was retained while the temperature of the sample block was lowered to 4° C.

Purification of the sequencing products was performed using the CENTRI-SEP Spin Column (Life Technologies). More specifically, to the center of the CENTRI-SEP Spin Column, which had been preliminarily treated by swelling the filler at room temperature for at least 2 hours, the resulting sequencing product (about 20 μL) was added in such a manner as if it were placed on top of the column. A 1.5 mL microtube was placed beneath the column, and centrifugation was performed at 2,700 rpm (ca. 500×g) for 2 minutes to recover a solution gathered in the microtube, as purified DNA. The resulting solution was dried under reduced pressure, 20 μL of TSR or Hi-Di formamide was added, and after being left to stand for about 10 minutes, the solution was mixed well. The solution was transferred to a 0.2 mL microtube (for PCR) and denatured (at 95° C. for 2 min) in the DNA Thermal Cycler GeneAmp PCR System 9600, and immediately thereafter the microtube was quenched in ice and left to stand as it was for at least 10 minutes.

(7) DNA Sequencing

DNA sequencing was performed using the ABI PRISM 310 Genetic Analyzer according to the "ABI PRISM 310 Genetic Analyzer User's Manual". More specifically, The sample obtained after the quenching described above was transferred in a sample tube, and the tube was capped with a septa cap and placed in a 48-well sample tray. Thereafter, sequencing was performed by the dye terminator method in line with the User's Manual. Additionally, there is a limit to the length of fragment that can be sequenced by an analyzer, though the length varies with the type of the analyzer. Therefore, since the fragment of region A1-2 has a length of about 1,500 bp, the sequencing data obtained for this region consisted of those for the following two regions: region A1-2-L of about 500 bp from the 5' end (primer L), and region A1-2-R of about 800 bp from the 3' end (primer R).

(8) Determining Nucleotide Sequences

The sequence data obtained from the 5' end (primer L) and the 3' end (primer R), respectively, were checked against each other to determine exact nucleotide sequences.

(g) Determining Identification Markers

The nucleotide sequences of 14 varieties which were determined above in (f) were aligned for each identification region to locate SNPs.

Fourteen varieties of hops selected as objects to be identified were determined for their nucleotide sequence of region A1. The sequence ID numbers to the nucleotide sequences of region A1 in these varieties are listed below in Table 7.

TABLE 7

| Variety | Sequence of region A1 |
|---|---|
| Saaz | SEQ ID NO: 16 |
| Sladeck | SEQ ID NO: 17 |
| Premiant | SEQ ID NO: 18 |
| Tradition | SEQ ID NO: 19 |
| Spalter | SEQ ID NO: 20 |
| Spalter Select | SEQ ID NO: 21 |
| Perle | SEQ ID NO: 22 |
| Tettnang | SEQ ID NO: 23 |
| Brewer's Gold | SEQ ID NO: 24 |
| Nothern Brewer | SEQ ID NO: 25 |
| Magnum | SEQ ID NO: 26 |
| Herkules | SEQ ID NO: 27 |
| German Nugget | SEQ ID NO: 28 |
| Taurus | SEQ ID NO: 29 |

These nucleotide sequences were aligned to determine the consensus sequence (SEQ ID NO: 9) in region A1. The nucleotide sequences determined in these varieties as listed in Table 7 were evaluated for 24 SNPs in region A1, i.e., SNPs corresponding to nucleotide positions 74, 77, 87, 103, 116, 118, 121, 125, 134, 135, 148, 192, 195, 197, 199, 203, 204, 226, 230, 235, 306, 316, 330 and 532 in SEQ ID NO: 9. The 14 varieties of hops to be identified showed 9 types (types 1 to 9) of combinations of 24 SNPs in region A1. The results are shown in FIG. 1.

Next, the 14 varieties of hops selected as objects to be identified were determined for their nucleotide sequence of region B1. The sequence ID numbers to the nucleotide sequences of region B1 in these varieties are listed below in Table 8.

TABLE 8

| Variety | Sequence of region B1 |
|---|---|
| Saaz | SEQ ID NO: 30 |
| Sladeck | SEQ ID NO: 31 |
| Premiant | SEQ ID NO: 32 |
| Tradition | SEQ ID NO: 33 |
| Spalter | SEQ ID NO: 34 |
| Spalter Select | SEQ ID NO: 35 |
| Perle | SEQ ID NO: 36 |
| Tettnang | SEQ ID NO: 37 |
| Brewer's Gold | SEQ ID NO: 38 |
| Nothern Brewer | SEQ ID NO: 39 |
| Magnum | SEQ ID NO: 40 |
| Herkules | SEQ ID NO: 41 |
| German Nugget | SEQ ID NO: 42 |
| Taurus | SEQ ID NO: 43 |

These nucleotide sequences were aligned to determine the consensus sequence (SEQ ID NO: 10) in region B1. The nucleotide sequences determined in these varieties as listed in Table 8 were evaluated for 10 SNPs in region B1, i.e., SNPs corresponding to nucleotide positions 178, 204, 227, 234, 370, 426, 439, ¶¶547, 562 and 624 in SEQ ID NO: 10. The 14 varieties of hops to be identified showed 7 types (types a to g) of combinations of 10 SNPs in region B1. The results are shown in FIG. 2.

Next, the 14 varieties of hops selected as objects to be identified were determined for their nucleotide sequence of region C1. The sequence ID numbers to the nucleotide sequences of region C1 in these varieties are listed below in Table 9.

TABLE 9

| Variety | Sequence of region C1 |
|---|---|
| Saaz | SEQ ID NO: 44 |
| Sladeck | SEQ ID NO: 45 |
| Premiant | SEQ ID NO: 46 |
| Tradition | SEQ ID NO: 47 |
| Spalter | SEQ ID NO: 48 |
| Spalter Select | SEQ ID NO: 49 |
| Perle | SEQ ID NO: 50 |
| Tettnang | SEQ ID NO: 51 |
| Brewer's Gold | SEQ ID NO: 52 |
| Nothern Brewer | SEQ ID NO: 53 |
| Magnum | SEQ ID NO: 54 |
| Herkules | SEQ ID NO: 55 |
| German Nugget | SEQ ID NO: 56 |
| Taurus | SEQ ID NO: 57 |

These nucleotide sequences were aligned to determine the consensus sequence (SEQ ID NO: 11) in region C1. The nucleotide sequences determined in these varieties as listed in Table 9 were evaluated for 29 SNPs in region C1 (6 of these 29 SNPs constitute an insertion-deletion portion), i.e., SNPs corresponding to nucleotide positions 3, 13, 17, 87, 88, 129, 130, 131, 132, 133, 134, 254, 331, 356, 375, 380, 396, 398, 399, 421, 460, 474, 475, 476, 477, 480, 481, 500 and 547 (positions 129-134 constitute an indel portion) in SEQ ID NO: 11. The 14 varieties of hops to be identified showed 3 types (types i to iii) of combinations of 29 SNPs or an indel portion in region C1. The results are shown in FIG. 3.

The analyses of 24 SNPs in region A1, 10 SNPs in region B1, and 29 SNPs or an indel portion in region C1 made it possible to classify 12 of 14 varieties, excluding Perle and Northern Brewer, into respective different types (FIG. 5).

For the purpose of identifying Perle and Northern Brewer, these varieties were further analyzed for their nucleotide sequence of region A1-2. The nucleotide sequences of regions A1-2-L and A1-2-R in a DNA sample derived from Perle are shown in SEQ ID NOs: 58 and 60, respectively, and those sequences in a DNA sample derived from Northern Brewer are shown in SEQ ID NOs: 59 and 61, respectively. These sequences were aligned to determine the consensus sequences (SEQ ID NOs: 12 and 14) in regions A1-2-L and A1-2-R, respectively. The nucleotide sequences determined in Perle and Northern Brewer were evaluated for SNPs corresponding to those nucleotide positions in SEQ ID NOs: 12 and 14 which are identified in FIG. 4. As a result, there was observed a difference in multiple SNPs as shown in FIG. 4.

Accordingly, an identification marker capable of identifying all of the 14 varieties listed in Table 4 was successfully prepared by combining not only the SNPs in regions A1, B1 and C1 but also at least one of the SNPs in regions A1-2-L and A1-2-R (FIG. 5).

Further, for the following 5 varieties Sladeck (Sládek), Spalter, Perle, Tettnang and Northern Brewer, identification markers of regions A1-2-L and A1-2-R were determined.

The above-mentioned 5 varieties of hops were determined for their nucleotide sequence of region A1-2-L. The sequence ID numbers to the nucleotide sequences of region A1-2-L in these varieties are listed below in Table 10.

TABLE 10

| Variety | Sequence of region A1-2-L |
|---|---|
| Sladeck | SEQ ID NO: 62 |
| Spalter | SEQ ID NO: 63 |
| Perle | SEQ ID NO: 64 |
| Tettnang | SEQ ID NO: 65 |
| Nothern Brewer | SEQ ID NO: 66 |

These nucleotide sequences were aligned to determine the consensus sequence (SEQ ID NO: 13) in region A1-2-L. The nucleotide sequences determined in these varieties as listed in Table 10 were evaluated for 23 SNPs in region A1-2-L (11 of these 23 SNPs constitute insertion-deletion portions), i.e., SNPs corresponding to nucleotide positions 2, 12, 31, 98, 115, 121, 161, 165, 168, 183, 184, 185, 186, 187, 188, 189, 190, 191, 389, 395, 396, 456 and 499 (position 12, positions 183-191, and position 396 each constitute an indel portion) in SEQ ID NO: 13. The 5 varieties of hops to be identified showed 5 types (types (1) to (5)) of combinations of 23 SNPs or indel portions in region A1-2-L. The results are shown in FIG. 6.

An identification marker capable of identifying the 5 varieties listed in Table 10 was successfully prepared by combining the SNPs or indel portions in region A1-2-L.

Furthermore, the above-mentioned 5 varieties of hops were determined for their nucleotide sequence of region A1-2-R. The sequence ID numbers to the nucleotide sequences of region A1-2-R in these varieties are listed below in Table 11.

TABLE 11

| Variety | Sequence of region A1-2-R |
|---|---|
| Sladeck | SEQ ID NO: 67 |
| Spalter | SEQ ID NO: 68 |
| Perle | SEQ ID NO: 69 |
| Tettnang | SEQ ID NO: 70 |
| Nothern Brewer | SEQ ID NO: 71 |

These nucleotide sequences were aligned to determine the consensus sequence (SEQ ID NO: 15) in region A1-2-R. The nucleotide sequences determined in these varieties as listed in Table 11 were evaluated for 28 SNPs in region A1-2-R (1 of these 28 SNPs constitutes an insertion-deletion portion), i.e., SNPs corresponding to nucleotide positions 2, 6, 12, 13, 18, 20, 22, 24, 26, 36, 52, 87, 88, 125, 139, 140, 160, 162, 167, 188, 223, 249, 273, 284, 326, 339, 421 and 437 (position 437 constitutes an indel portion) in SEQ ID NO: 15. The 5 varieties of hops to be identified showed 4 types (types (a) to (d)) of combinations of 28 SNPs or an indel portion in region A1-2-R. The results are shown in FIG. 6.

An identification marker capable of identifying 4 of the 5 varieties listed in Table 10 (i.e., 3 varieties and 1 group of 2 varieties) was successfully prepared by combining the SNPs or indel portion in region A1-2-R.

Example 2: Comparison Between the Two Procedures for Preparing a DNA Sample

Comparison was made between the results obtained in the two cases where DNA samples were extracted from hop pellets or dried hop cones, respectively, as described in (2) "DNA extraction" under (f) of Example 1.

As a result, it was confirmed that DNA extraction and sequencing are possible with both types of DNA samples prepared using hop pellets as a starting material or using dried hop cones as a starting material. Also confirmed was that the DNA analyses of both types of samples yield the same results.

Accordingly, it was demonstrated that even in the case of using dried hop cones, DNA analysis is possible as in the case of using pellets, and that inspection at a processing step (e.g., contamination inspection at a pelletization step) is technically possible.

Example 3: Comparison Between Clones

About 1 g each of dried cones of three Saaz clones (Osvald's clones 31, 72 and 114) were ground in a mortar in the presence of liquid nitrogen, and DNAs were extracted from about 50 mg each of the ground materials by the CTAB method according to the same procedure as described in (2) under (f) of Example 1. Each of the extracted DNA samples was subjected to amplification of the DNA fragments of regions A1, B1 and C1 and sequencing of the amplified DNA fragments, according to the same procedures as described in (3) to (7) under (f) of Example 1. For each region, the nucleotide sequences of the three clone varieties were aligned and compared with each other.

As a result, it was confirmed that there is no difference between three Saaz clone varieties in terms of the nucleotide sequences of the analyzed regions. In other words, it was found that any of Saaz clones, if used, is identified as Saaz through the above-described analysis using the inventive variety identification regions. These results demonstrated that the analysis using regions A1, B1 and C1 as variety identification regions requires no determination by clone.

Example 4: Model Testing for Mixing of a Different Hop Variety

The mixed samples of Saaz and Premiant hops were analyzed (for region A1). Pellets of these respective varieties were ground as per Example 1, and then the respective ground materials were mixed in the relative proportions by weight as shown in Table 12 to prepare different samples.

TABLE 12

| <Analyzed samples (prepared by mixing pellets of two varieties in specified proportions by weight)> | | | | | |
|---|---|---|---|---|---|
| Proportion of Saaz | (1) 100% | (2) 95% | (3) 90% | (4) 50% | (5) 0% |
| Saaz | 30 mg | 28.5 mg | 27 mg | 15 mg | — |
| Premiant | — | 1.5 mg | 3 mg | 15 mg | 30 mg |

Samples (1) to (5) were each subjected to DNA extraction, amplification of region A1 by PCR, sequencing, and data analysis by following the same procedures as in Example 1. As a result, the lower detection limit in mixing proportion was successfully determined to be approximately 5% by investigating how the relative proportions of these varieties reflect their electropherogram (waveforms) as shown in FIG. 8. For example, it is evident that, at the SNP position corresponding to nucleotide position 199 in SEQ ID NO: 9, the nucleotide of the Saaz variety is T while that of the Premiant variety is C, and the shapes (heights) of the peaks for the respective nucleotides of these varieties vary with the mixing proportions of said varieties. In other words, in the case where the relative proportion of Saaz is 100%, the electropherogram does not show any other waveform than that of T, while in cases where Premiant is mixed in different proportions, the waveform of C is superimposed on that of T. Also, in the case where Premiant is mixed in a proportion of 5%, the electropherogram shows the waveform of C, though only a slight one, as compared to the case of no mixing.

Example 5: Identification of U.S. Varieties

This example tested whether the analysis of regions A1, B1, C1 and A1-2 (and SNPs contained therein) is also applicable to identification of U.S. hop varieties.
A. Methodology
1. Varieties to be Tested
As varieties to be identified, there were used 8 U.S. hop varieties listed below in Table 13 (Cascade, Zeus, Summit, Galena, Super Galena, Nugget, Columbus, and Tomahawk).

TABLE 13

| No. | US. varieties to be identified |
|---|---|
| 1 | Cascade |
| 2 | Zeus |
| 3 | Summit |
| 4 | Galena |
| 5 | Super Galena |
| 6 | Nugget |
| 7 | Columbus |
| 8 | Tomahawk |

2. DNA Extraction
In line with the procedure described in b. "Extraction from dried hop cones" in Example 1, about 1 g each of dried hop cones of these varieties were ground in a mortar in the presence of liquid nitrogen, and a DNA sample was prepared from 10-50 mg each of the ground materials.
3. Confirming PCR and Amplification, and Purifying Amplification products
Following the procedures described in (3) "PCR" to (5) "Purifying PCR products" in Example 1, and using respective primer sets for regions A1, B1, C1 and A1-2, PCR was performed, amplification was confirmed, and then amplification products were purified.
4. DNA Sequencing
Each purified PCR product, a primer for each region (one primer of each primer pair, which defines one single strand to be sequenced), and pure water were mixed to give a volume of 14 µL, and the prepared samples were sequenced under a subcontract to Operon Biotechnologies to obtain sequencing results (raw data, electropherograms, and sequencing data processed by PC from the electropherograms).
5. Analyzing Sequencing Results
The data obtained from the 5' end (primer L) and the 3' end (primer R), respectively, at the above step 4 were checked against each other to determine exact nucleotide sequences.
B. Results
The results are shown below.
1. Testing Using a Marker for Region A1
PCR amplification using the primers for region A1 was possible for all of the 8 hop varieties. These varieties were successfully classified into 4 types through sequencing (Table 14).
The sequence ID numbers to the nucleotide sequences of region A1 in these varieties are listed below in Table 15.

TABLE 14

SNP analysis results in region A1

| Variety to be identified | 74 | 77 | 87 | 103 | 116 | 118 | 121 | 125 | 134 | 135 | 148 | 192 | 195 | 197 | 199 | 203 | 204 | 226 | 230 | 235 | 306 | 316 | 330 | 532 | type |
|---|---|---|---|---|---|---|---|---|---|---|---|---|---|---|---|---|---|---|---|---|---|---|---|---|---|
| European variety ||||||||||||||||||||||||||
| Saaz | W | T | K | A | W | Y | W | W | K | R | Y | G | K | W | T | R | S | M | Y | Y | Y | M | T | G | 1 |
| Sladeck | A | C | T | G | T | T | T | A | T | G | T | A | G | T | C | G | C | A | C | T | C | C | A | C | 2 |
| Premiant | A | C | T | G | T | T | T | A | T | G | T | A | G | T | C | G | C | A | C | T | C | C | A | C | 2 |
| Tradition | W | T | K | A | W | Y | W | W | K | R | Y | G | K | W | T | R | S | M | Y | Y | Y | C | W | G | 3 |
| Spalter | W | T | K | A | W | Y | W | W | K | R | Y | G | K | W | T | R | S | M | Y | Y | Y | M | W | G | 4 |
| Spalter Select | A | C | T | G | T | T | T | A | T | G | T | A | G | T | C | G | C | A | C | T | C | C | A | C | 2 |
| Perle | A | C | T | G | T | T | T | A | T | G | T | A | G | T | C | G | C | A | C | T | C | C | A | C | 2 |
| Tettnang | W | T | K | A | W | Y | W | W | K | R | T | G | K | W | T | R | S | C | Y | Y | Y | M | W | G | 5 |
| Brewer's Gold | A | T | K | A | T | W | W | W | K | R | T | G | G | T | T | R | S | M | Y | T | Y | M | W | S | 7 |
| Northern Brewer | A | C | T | G | T | T | T | A | T | G | T | A | G | T | C | G | C | A | C | T | C | C | A | C | 2 |
| Magnum | A | C | T | G | T | T | T | A | T | G | T | A | G | T | C | G | C | A | C | T | C | C | A | C | 2 |
| Herkules | A | C | T | G | T | T | T | A | T | G | T | R | G | T | Y | G | C | A | C | T | C | C | A | S | 6 |
| German Nympt | A | C | T | G | T | T | T | A | T | G | T | A | G | T | C | G | C | A | C | T | C | C | A | S | 9 |
| Taurus | A | T | K | A | T | Y | D | W | K | R | T | G | G | T | T | R | S | M | Y | Y | Y | M | W | S | 8 |
| U.S. variety ||||||||||||||||||||||||||
| Cascade | A | C | T | G | T | T | T | A | T | G | T | A | G | T | C | G | C | A | C | T | C | C | A | C | 2 |
| Zeus | A | C | T | G | T | T | T | A | T | G | T | A | G | T | C | G | C | A | C | T | C | C | A | C | 2 |
| Summit | A | C | T | G | T | T | T | A | T | G | T | A | G | T | C | G | C | A | C | T | C | C | A | C | 2 |
| Galena | A | C | T | G | T | T | T | A | T | G | T | A | G | T | C | G | C | A | C | T | C | C | A | C | 2 |
| Super Galena | A | T | K | A | W | T | W | W | K | R | T | G | G | T | T | R | S | M | Y | Y | Y | M | W | S | 5b |
| Nugget | A | Y | K | R | T | T | T | A | K | R | T | R | G | T | Y | G | C | A | C | T | C | C | A | C | 10 |
| Columbus | A | Y | T | R | T | T | T | A | T | G | T | R | G | T | Y | G | C | A | C | T | C | C | A | C | 6b |
| Tomahawk | A | Y | T | R | T | T | T | A | T | G | T | R | G | T | Y | G | C | A | C | T | C | C | A | C | 6b |

Nucleotide code table

| | | |
|---|---|---|
| A, C, G, or T | N | |
| C, G, or T (not A) | B | A or G (purine) R |
| A, G, or T (not C) | D | C or T (pyrimidine) Y |
| A, C, or T (not G) | H | G or T (keto) K |
| A, C, or G (not T) | V | A or C (amine) M |
| | | G or C (strong) S |
| | | A or T (weak) W |

TABLE 15

| Variety | Sequence of region A1 |
|---|---|
| Cascade | SEQ ID NO: 78 |
| Zeus | SEQ ID NO: 79 |
| Summit | SEQ ID NO: 80 |
| Galena | SEQ ID NO: 81 |
| Super Galena | SEQ ID NO: 82 |
| Nugget | SEQ ID NO: 83 |
| Columbus | SEQ ID NO: 84 |
| Tomahawk | SEQ ID NO: 85 |

2. Testing Using a Marker for Region B1

PCR amplification using the primers for region B1 was possible for all of the 8 hop varieties. These 8 varieties were successfully classified into 4 types through sequencing (Table 16).

The sequence ID numbers to the nucleotide sequences of region B1 in these varieties are listed below in Table 17. Since Galena has two types of sequences, identification based on the difference in sequence (nucleotide positions 245-248) may also be made possible.

The consensus sequence (represented by the characters A, G, C and T) and the SNP positions (represented by the character N) in region B1 as observed in the case of identification of different varieties including U.S. ones are shown in the sequence listing as SEQ ID NO: 105.

TABLE 16

SNP analysis results in region B1

| Variety to be identified | 178 | 204 | 227 | 234 | 245 | 246 | 247 | 248 | 370 | 426 | 439 | 547 | 562 | 624 | type |
|---|---|---|---|---|---|---|---|---|---|---|---|---|---|---|---|
| Saaz | R | A | R | A | T | G | A | T | R | M | R | Y | Y | S | a |
| Sladeck | R | A | G | A | T | G | A | T | R | M | R | Y | Y | S | b |
| Premiant | A | A | G | A | T | G | A | T | A | C | A | T | T | C | c |

TABLE 16-continued

SNP analysis results in region B1

| Variety to be identified | 178 | 204 | 227 | 234 | 245 | 246 | 247 | 248 | 370 | 426 | 439 | 547 | 562 | 624 | type |
|---|---|---|---|---|---|---|---|---|---|---|---|---|---|---|---|
| Tradition | A | A | G | A | T | G | A | T | A | C | A | Y | T | C | d |
| Spalter | R | A | G | A | T | G | A | T | R | M | A | T | Y | S | e |
| Spalter Select | R | A | G | A | T | G | A | T | R | M | R | T | Y | S | f |
| Perle | A | A | G | A | T | G | A | T | A | C | A | Y | T | C | d |
| Tettnang | R | M | R | R | T | G | A | T | R | M | A | T | Y | Y | g |
| Brewer's Gold | A | A | G | A | T | G | A | T | A | C | A | T | T | C | c |
| Northern Brewer | A | A | G | A | T | G | A | T | A | C | A | Y | T | C | d |
| Magnum | A | A | G | A | T | G | A | T | A | C | A | Y | T | C | d |
| Herkules | A | A | G | A | T | G | A | T | A | C | A | Y | T | C | d |
| German Nugget | A | A | G | A | T | G | A | T | A | C | A | T | T | C | c |
| Taurus | A | A | G | A | T | G | A | T | A | C | A | Y | T | C | d |
| Cascade | A | A | G | A | T | G | A | T | A | C | A | Y | T | C | d |
| Zeus | A | A | G | A | T | G | A | T | A | M | A | T | T | C | c1 |
| Summit | A | A | G | A | T | G | A | T | A | M | A | T | T | C | c2 |
| Galena | R | M | R | R | T | G | A | T | A | C | G | T | T | S | h |
|  | R | M | R | R |  |  |  |  | A | A | G | T | C | S | i |
| Super Galena | A | A | G | A | T | G | A | T | A | C | A | T | T | C | c |
| Nugget | A | A | G | A | T | G | A | T | A | C | A | T | T | C | c |
| Columbus | A | A | G | A | T | G | A | T | A | C | A | T | T | C | c |
| Tomahawk | A | A | G | A | T | G | A | T | A | C | A | T | T | C | c |

TABLE 17

| Variety | Sequence of region B1 |
|---|---|
| Cascade | SEQ ID NO: 86 |
| Zeus | SEQ ID NO: 87 |
| Summit | SEQ ID NO: 88 |
| Galena | SEQ ID NO: 89, SEQ ID NO: 90 |
| Super Galena | SEQ ID NO: 91 |
| Nugget | SEQ ID NO: 92 |
| Columbus | SEQ ID NO: 93 |
| Tomahawk | SEQ ID NO: 94 |

3. Testing Using a Marker for Region C1

PCR amplification using the primers for region C1 was possible for all of the 8 hop varieties. As the result of sequencing, these varieties 8 were successfully classified into 3 types through sequencing (Table 18).

The sequence ID numbers to the nucleotide sequences of region C1 in these varieties are listed below in Table 19. Since Cascade and Super Galena each have two types of sequences, identification based on the difference in sequence may also be made possible.

The consensus sequence (represented by the characters A, G, C and T) and the SNP positions (represented by the character N) in region C1 as observed in the case of identification of different varieties including U.S. ones are shown in the sequence listing as SEQ ID NO: 106.

TABLE 18

SNP analysis results in region C1

| Variety to be identified | 3 | 13 | 17 | 76 | 77 | 80 | 87 | 88 | 93 | 129 | 130 | 131 | 132 | 133 | 134 | 136 | 138 | 163 | 165 | 245 | 254 | 313 | 321 | 331 | 356 |
|---|---|---|---|---|---|---|---|---|---|---|---|---|---|---|---|---|---|---|---|---|---|---|---|---|---|
| European Variety | | | | | | | | | | | | | | | | | | | | | | | | | |
| Saaz | T | C | G | G | G | A | A | G | A | − | − | − | − | − | − | T | G | A | C | G | T | A | T | A | G |
| Sladeck | T | C | G | G | G | A | A | G | A | − | − | − | − | − | − | T | G | A | C | G | T | A | T | A | G |
| Premiant | T | C | G | G | G | A | A | G | A | − | − | − | − | − | − | T | G | A | C | G | T | A | T | A | G |
| Tradition | C | G | T | G | G | A | T | T | A | C | A | T | G | A | C | T | G | A | C | G | C | A | T | A | G |
| Spalter | T | C | G | G | G | A | A | G | A | − | − | − | − | − | − | T | G | A | C | G | T | A | T | A | G |
| Spalter Select | C | G | T | G | G | A | T | T | A | C | A | T | G | A | C | T | G | A | C | G | C | A | T | A | G |
| Perle | T | C | G | G | G | A | A | G | A | − | − | − | − | − | − | T | G | A | C | G | T | A | T | A | G |
| Tettnang | T | C | G | G | G | A | A | G | A | − | − | − | − | − | − | T | G | A | C | G | T | A | T | A | G |
| Brew Gold | T | C | G | G | G | A | A | G | A | − | − | − | − | − | − | T | G | A | C | G | T | A | T | A | G |
| Northern Brewer | T | C | G | G | G | A | A | G | A | − | − | − | − | − | − | T | G | A | C | G | T | A | T | A | G |
| Magnum | T | C | G | G | G | A | A | G | A | − | − | − | − | − | − | T | G | A | C | G | T | A | T | R | R |
| Herkules | C | G | T | G | G | A | T | T | A | C | A | T | G | A | C | T | G | A | C | G | C | A | T | A | G |
| German Nugget | T | C | G | G | G | A | A | G | A | − | − | − | − | − | − | T | G | A | C | G | T | A | T | A | G |
| Taurus | T | C | G | G | G | A | A | G | A | − | − | − | − | − | − | T | G | A | C | G | T | A | T | A | G |
| U.S. Variety | | | | | | | | | | | | | | | | | | | | | | | | | |
| Cascade | T | G | G | G | G | A | T | T | A | C | A | T | G | A | C | T | G | A | C | G | C | A | T | A | G |
|  | T | G | G | G | G | A | A | G | A | − | − | − | − | − | − | T | G | A | C | G | C | A | T | A | G |
| Zeus | T | C | G | G | G | A | A | G | A | − | − | − | − | − | − | T | G | A | C | G | T | A | T | A | G |
| Summit | T | C | G | G | G | A | A | G | A | − | − | − | − | − | − | T | G | A | C | G | T | A | T | A | G |
| Galena | T | C | G | G | G | A | A | G | A | − | − | − | − | − | − | T | G | A | C | G | T | A | T | A | G |

TABLE 18-continued

SNP analysis results in region C1

| Variety to be identified | SNP position | | | | | | | | | | | | | | | | | | | | | | | | |
|---|---|---|---|---|---|---|---|---|---|---|---|---|---|---|---|---|---|---|---|---|---|---|---|---|---|
| | 3 | 13 | 17 | 76 | 77 | 80 | 87 | 88 | 93 | 129 | 130 | 131 | 132 | 133 | 134 | 136 | 138 | 163 | 165 | 245 | 254 | 313 | 321 | 331 | 356 |
| Super Galena | T | C | G | G | G | A | A | G | A | – | – | – | – | – | – | T | G | A | C | G | T | A | T | A | G |
| | T | C | G | A | A | A | A | G | C | G | A | T | G | A | C | C | C | G | G | A | T | T | C | A | G |
| Nugget | T | C | G | G | G | A | A | G | A | – | – | – | – | – | – | T | G | A | C | G | T | A | T | A | G |
| Columbus | T | C | G | G | G | A | A | G | A | – | – | – | – | – | – | T | G | A | C | G | T | A | T | A | G |
| Tomahawk | T | C | G | G | G | A | A | G | A | – | – | – | – | – | – | T | G | A | C | G | T | A | T | A | G |

TABLE 19

| Variety | Sequence of region C1 |
|---|---|
| Cascade | SEQ ID NO: 95, SEQ ID NO: 96 |
| Zeus | SEQ ID NO: 97 |
| Summit | SEQ ID NO: 98 |
| Galena | SEQ ID NO: 99 |
| Super Galena | SEQ ID NO: 100, SEQ ID NO: 101 |
| Nugget | SEQ ID NO: 102 |
| Columbus | SEQ ID NO: 103 |
| Tomahawk | SEQ ID NO: 104 |

Putting all the analysis results for the three regions together, PCR amplification using primers was possible for all of the varieties. Also, as the result of sequencing, the DNA types obtained from 6 of the 8 varieties differ from each other and are all those types which are not found in European varieties; thus, identification among these 6 varieties was found to be possible. However, the remaining two varieties Zeus and Summit show the DNA type C which is the same as that of Premiant native to Czech (Tables 14, 16 and 18).

4. Analysis Using a Marker for Region A1-2

Zeus and Summit, whose DNA had been classified as type C, identical to Premiant native Czech, through the analyses for respective regions A1, B1 and C1, were subjected to further analysis for region A1-2-R. As a result, indel portions, SSRs, and SNPs were observed to be present among the above-mentioned three similar varieties. In particular, they differ significantly from each other in terms of indel portions and SSRs (Table 20). Table 20 is prepared based on the nucleotide numbers given in SEQ ID NO: 14. In this table, the sequences of Premiant, Zeus and Summit are placed in this order from the top in alignment with each other, and below them are shown the consensus sequence (represented by the characters A, G, C and T) and the SNP positions (represented by the character N) as observed in the case of identification of Perle and Northern Brewer. The consensus sequence (represented by the characters A, G, C and T) and the SNP positions (represented by the character N) in region A1-2 as observed in the case of identification of U.S. varieties are shown in the sequence listing as SEQ ID NO: 107.

As is evident from Table 20, the insertion of 22 nucleotides at nucleotide positions 64-85 was observed in Premiant and Summit but not in Zeus. Besides, as the result of more detailed observation, 3 SNPs (at nucleotide positions 64, 67 and 75) between Premiant and Summit were found even in the above-mentioned insertion sequence of 22 nucleotides. Even in this region alone, there was found a difference among these three varieties, but another more significant difference which was observed among them is that, in terms of the repeat sequence CA or TA which follows this insertion sequence and extends up to nucleotide position 141, only Summit is longer by 12 nucleotides than the other two varieties. Thus, identification among these three varieties became possible by combining these results.

TABLE 20

SNP analysis results in region A1-2-R

```
                           10         20         30         40         50         60
Premiant-A1-2_R-RC  AGCACGATGC TTTGCCCGAT TTATTGCTGA GCTTGAGAAT TTGCAAGGAA AGCACAGGTA
Zeus-A1-2_R-RC      AGTACGATGC TTTGCCCGAT TTATTGTCGA GCTTGAGAAT TTGCAAAGAA AGCACAGGTA
Summit-A1-2_R-RC    AGCACGAGGC TTTGCCCGCG TTATTGCTGA GCTTGAGAAA ATGCACGGAA AGCACACGTA
A1-2-R 2VER cons.   NNNANGANNN NNNNNNNGAN NTATNNNNNN NCNTNNNNAT NNNNANNNAN N-CACANNNN 70         80         90        100        110        120
Premiant-A1-2_R-RC  ACA|TATCTAT AGACCTATAC ATGCA|TATAT ACACACACAC ACACACACAC ACACACACA-
Zeus-A1-2_R-RC      ACA------ ---------- -----TATAC ACACACACAC ACACACACAC ATACATATA-
Summit-A1-2_R-RC    ACA|CATATAT AGACATATAC ATGCA|TATAT ACACACACAC ACACACACAC ACACACACAC
A1-2-R 2VER cons.   ACA------ ---------- --------NA NCANACANAC ACANNCACAN ANANANANA- 130        140        150        160        170        180
Premiant-A1-2_R-RC  ---------- -TATACATAT AATGTAAATG TTGATACTCT ATTGTGATGA TTTGCTTCTG
Zeus-A1-2_R-RC      ---------- -TATACATAG AATGTAAATG TTGATTCTCT ATTGTGATGA TTTGCTTTTG
Summit-A1-2_R-RC    ACACACACAC ATATACATAC AATGTAAATG TTGATACTCT ATTGTGATGA TTTGCTTCTG
A1-2-R 2VER cons.   ---------- -TATACATAT AATGTAAATG TTGATNCTCT ATTGTGATGA TTTGCTTCTG
```

In Table 20, Premiant-A1-2_R-RC corresponds to SEQ ID NO: 108; Zeus-A1-2_R-RC corresponds to SEQ ID NO: 109; Summit-A1-2_R-RC corresponds to SEQ ID NO: 110; and A1-2-R 2VER cons. corresponds to nt 1-152 of SEQ ID NO: 14.

5. Conclusion

Putting together the results given above so far, identification of the 8 U.S. hop varieties was found to be possible as the result of the analyses for respective regions A1, B1, C1 and A1-2. It also became possible to identify a total of 22 hop varieties which consist of not only 8 U.S. varieties but also 3 Czech varieties and 11 German varieties (Table 21).

TABLE 21

Identification results for a total 22 of European and U.S. hop varieties

| Country of origin | Variety to be identified | Diplotype | | | | A1 + B1 + C1 + (A1 − 2) | Possibility/ impossibility of identification |
|---|---|---|---|---|---|---|---|
| | | A1 | B1 | C1 | A1-2 | | |
| Czech | Saaz | 1 | a | i | | A | ○ |
| | Sladeck | 2 | b | i | | B | ○ |
| | Premiant | 2 | c | i | γ | C | ○ |
| Germany | Tradition | 3 | d | ii | | D | ○ |
| | Spalter | 4 | e | i | | E | ○ |
| | Spalter Select | 2 | f | ii | | F | ○ |
| | Perle | 2 | d | i | α | G | ○ |
| | Tettnang | 5 | g | i | | H | ○ |
| | Brewer's Gold | 7 | c | i | | I | ○ |
| | Northern Brewer | 2 | d | i | β | N | ○ |
| | Magnum | 2 | d | iii | | J | ○ |
| | Herkules | 6 | d | ii | | K | ○ |
| | German Nugget | 9 | c | i | | L | ○ |
| | Taurus | 8 | d | i | | M | ○ |
| U.S. | Cascade | 2 | d | iv | | O | ○ |
| | Zeus | 2 | c | i | δ | U | ○ |
| | Summit | 2 | c | i | θ | V | ○ |
| | Galena | 2 | h | i | | P | ○ |
| | Super Galena | 5b | c | v | | Q | ○ |
| | Nugget | 10 | i | i | | R | ○ |
| | Columbus | 6b | i | i | | S | ○ |
| | Tomahawk | 6b | c | i | | T | ○ |

SEQUENCE LISTING FREE TEXT

SEQ ID NO: 1: Primer A1-3L
SEQ ID NO: 2: Primer A1-3R
SEQ ID NO: 3: Primer B1-1L
SEQ ID NO: 4: Primer B1-1R
SEQ ID NO: 5: Primer C1-1L
SEQ ID NO: 6: Primer C1-1R
SEQ ID NO: 7: Primer A1-2-1L
SEQ ID NO: 8: Primer A1-2-1R

The invention claimed is:

1. A method for brewing a beer, the method comprising identifying varieties of hops, selecting an identified hop variety, and brewing the beer, wherein identifying the varieties of hops comprises the steps of:
   (i) amplifying fragments of DNAs derived from hops to be tested with PCR using a primer set of the combination of SEQ ID NOs: 5 and 6, the fragments which each comprise a variety identification region comprising SEQ ID NO: 11, and wherein the variety identification region comprises an identification marker composed of at least one single nucleotide polymorphism (SNP) that differs among hop varieties;
   (ii) identifying the genotype of the single nucleotide polymorphism in each of the DNA fragments amplified at step (i);
   (iii) comparing the genotype of the single nucleotide polymorphism in the variety identification region in each of the DNAs from the hops to be tested, as identified at step (ii), with the genotype of a single nucleotide polymorphism in a corresponding region in a DNA from a known hop variety, to thereby analyze whether the hop varieties to be tested and the known hop variety are concordant or discordant for the genotype of the single nucleotide polymorphism in the region in question; and
   (iv) identifying the varieties of the hops to be tested, on the basis of the analysis results obtained at step (iii), wherein the varieties of the hops comprise Magnum, Cascade, and Super Galena.

2. The method as set forth in claim 1, wherein step (ii) is performed by identifying the nucleotide sequence of the variety identification region in each of the DNA fragments amplified at step (i); and
   wherein step (iii) is performed by comparing the nucleotide sequence of the variety identification region in each of the DNAs from the hops to be tested, as identified at step (ii), with the nucleotide sequence of a corresponding region in a DNA from a known hop variety, to thereby analyze whether the hop varieties to be tested and the known hop variety are concordant or discordant for an identification marker in the region in question.

3. The method as set forth in claim 1, wherein step (ii) is a step at which the genotype of the single nucleotide polymorphism in each of the DNA fragments amplified at step (i) is identified by contacting each of said DNA fragments with probes and/or primers for use in detecting the single nucleotide polymorphism that differs among hop varieties.

4. A method for analyzing a hop sample, the method comprising the steps of:
  (i) amplifying a fragment of a DNA extracted from a hop sample to be tested with PCR using a primer set of the combination of SEQ ID NOs: 5 and 6, the fragment which comprises a variety identification region comprising SEQ ID NO: 11, wherein the variety identification region comprises an identification marker composed of at least one single nucleotide polymorphism (SNP) that differs among hop varieties;
  (ii) analyzing the nucleotide sequence of the variety identification region in the DNA fragment amplified at step (i) to obtain sequence data;
  (iii) comparing the information on a single nucleotide polymorphic site constituting the identification marker, which is contained in the sequence data obtained at step (ii), with the information on a corresponding single nucleotide polymorphic site in a normal hop; and
  (iv) determining the presence or absence of mixing of a different hop variety in the hop sample, wherein, in the case where the information on the single nucleotide polymorphic site in the sequence data obtained at step (ii) is concordant with the information on the corresponding single nucleotide polymorphic site in the normal hop, it is determined that no different hop variety is mixed, or in the case where the information on the single nucleotide polymorphic site in the sequence data obtained at step (ii) is discordant with the information on the corresponding single nucleotide polymorphic site in the normal hop, it is determined that a different hop variety is mixed, wherein the varieties of the hops comprise Magnum, Cascade, and Super Galena.

5. The method as set forth in claim 4, further comprising, subsequently to step (iv), the steps of:
  (v) identifying a nucleotide different from that of the normal hop on the basis of an information derived from a hop other than the normal one, which appears in the single nucleotide polymorphic site in the sequence data obtained at step (ii), in the case where it is determined at step (iv) that the information on the single nucleotide polymorphic site in the sequence data obtained at step (ii) is discordant with the information on the corresponding single nucleotide polymorphic site in the normal hop; and
  (vi) checking the nucleotide different from that of the normal hop, which is identified in the single nucleotide polymorphic site at step (v), against the identification marker to deduce or identify the variety of the hop mixed.

6. The method as set forth in claim 4, further comprising, subsequently to step (iv), the steps of:
  (v) identifying a nucleotide different from that of the normal hop, and determining the mixing proportion thereof, on the basis of an information derived from a hop other than the normal one, which appears in the single nucleotide polymorphic site in the sequence data obtained at step (ii), in the case where it is determined at step (iv) that the information on the single nucleotide polymorphic site in the sequence data obtained at step (ii) is discordant with the information on the corresponding single nucleotide polymorphic site in the normal hop; and
  (vi) checking the nucleotide different from that of the normal hop, which is identified in the single nucleotide polymorphic site at step (v), against the identification marker to deduce or identify the variety of the hop mixed and the proportion of the hop variety mixed.

* * * * *